United States Patent [19]

Ono et al.

[11] Patent Number: 4,904,575
[45] Date of Patent: Feb. 27, 1990

[54] SILVER HALIDE COLOR PHOTOGRAPHIC MATERIAL WITH HETEROCYLIC FUSED PHENOL COUPLER

[75] Inventors: Michio Ono; Minoru Sakai; Kozo Aoki, all of Kanagawa, Japan

[73] Assignee: Fuji Photo Film Co., Ltd., Kanagawa, Japan

[21] Appl. No.: 216,573

[22] Filed: Jul. 8, 1988

[30] Foreign Application Priority Data

Jul. 9, 1987 [JP] Japan ................................. 62-171793
Nov. 24, 1987 [JP] Japan ................................. 62-295736

[51] Int. Cl.$^4$ ................................................. G03C 7/34
[52] U.S. Cl. .................................... 430/385; 430/384; 430/505; 430/512; 430/548; 430/549; 430/551; 430/552; 430/553
[58] Field of Search ............... 430/552, 553, 558, 384, 430/385, 512, 548, 549, 551, 505

[56] References Cited

U.S. PATENT DOCUMENTS 4,327,173 4/1982 Aoki et al. ......................... 430/558
4,430,423 2/1984 Aoki et al. ......................... 430/558
4,564,586 1/1986 Aoki et al. ......................... 430/553
4,746,602 5/1988 Ono et al. ......................... 430/553

Primary Examiner—Richard L. Schilling
Attorney, Agent, or Firm—Sughrue, Mion, Zinn, Macpeak & Seas

[57] ABSTRACT

A silver halide color photographic material comprising a support having coated thereon at least one silver halide emulsion layer, the silver halide color photographic material containing a photographic cyan dye forming coupler represented by the following general formula (I):

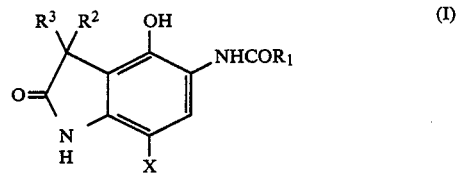

wherein $R_1$ represents an aliphatic group, an aromatic group, heterocyclic group or a substituted amino group; $R_2$ and $R_3$, which may be the same or different, each represents an aliphatic group, an aromatic group or a heterocyclic group, or $R_2$ and $R_3$ may combine with each other to form a ring; and X represents a group capable of beiing released upon an oxidative coupling with a developing agent (including a hydrogen atom).

The photographic cyan dye forming coupler has a high color forming rate and provides a high maximum color density even when a color developing solution which does not contain benzyl alcohol is used, and exhibits substantially no reduction in color density in the case of processing in a bleaching solution having a weak oxidation power or an exhausted bleaching solution.

The silver halide color photographic material containing the photographic cyan dye forming coupler can provide color images having excellent fastness and color reproducibility and less stain in white background area.

32 Claims, No Drawings

SILVER HALIDE COLOR PHOTOGRAPHIC MATERIAL WITH HETEROCYLIC FUSED PHENOL COUPLER

FIELD OF THE INVENTION

The present invention relates to a novel photographic cyan dye forming coupler, and more particularly, to a silver halide color photographic material containing a novel photographic cyan dye forming coupler.

BACKGROUND OF THE INVENTION

When color development processing is carried out after a silver halide photographic light-sensitive material is exposed to light, an oxidized aromatic primary amine developing agent reacts with a dye forming coupler to form a color image. In this process, color reproduction by a substractive process is generally utilized. In accordance with this process, color images of yellow, magenta and cyan, which are complement colors of blue, green and red, respectively, are formed in order to reproduce images of blue, green and red.

Phenol derivatives or naphthol derivatives are mainly used as cyan color image forming couplers. However, the color images formed from conventionally employed phenol derivatives or naphthol derivatives have some problems with respect to preservability. For example, color images formed from the 2-acylaminophenol cyan couplers as described in U.S. Pat. Nos. 2,367,531, 3,369,929, 2,423,730 and 2,801,171 generally have inferior fastness to heat. Color images formed from the 2,5-diacylaminophenol cyan couplers as described in U.S. Pat. Nos. 2,772,162 and 2,895,826 generally have inferior fastness to light, and color images formed from 1-hydroxy-2-naphthamide cyan couplers generally have inferior fastness to both light and heat (particularly humidity and heat).

Further, 5-hydroxy-6-acylaminocarbostyryl cyan couplers as described in U.S. Pat. Nos. 4,327,173 and 4,564,586 and 4-hydroxy-5-acylaminooxyindole cyan couplers and 4-hydroxy-5-acylamino-2,3-dihydro-1,3-benzimidazol-2-one cyan couplers as described in U.S. Pat. No. 4,430,423 are apt to form yellow stain in unexposed white background areas due to light and heat although color images formed therefrom have good fastness to light and heat. Thus, it has been desired to solve such problems.

SUMMARY OF THE INVENTION

It is an object of the present invention to provide a silver halide color photographic material containing a cyan dye forming coupler in which the abovedescribed defects are eliminated, and specifically which provides color images having excellent fastness and color reproducibility and less stain in white background areas.

Another object of the present invention is to provide a cyan dye forming coupler which has a high dye forming rate and provides a high maximum color density in a color developing solution, particularly even in a color developing solution which does not contain benzyl alcohol.

A further object of the present invention is to provide a cyan dye forming coupler which exhibits substantially no reduction in color density in the case of processing in a bleaching solution having a weak oxidation power, for example, a bleaching solution containing sodium salt of EDTA iron (III) or ammonium salt of EDTA iron (III), or an exhausted bleaching solution.

Other objects of the present invention will become apparent from the following detailed description and examples.

The above described objects of the present invention can be accomplished by using a 4-hydroxy-5-acylaminooxyindole coupler having two substituents at the 3-position thereof represented by the following general formula (I):

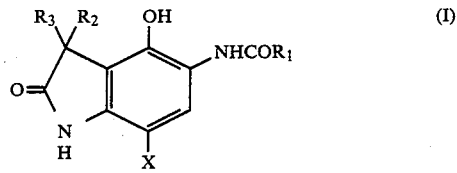

wherein $R_1$ represents an aliphatic group, an aromatic group, heterocyclic group or a substituted amino group; $R_2$ and $R_3$, which may be the same or different, each represents an aliphatic group, an aromatic group or a heterocyclic group, or $R_2$ and $R_3$ may combine with each other to form a ring; and X represents a group capable of being released upon an oxidative coupling with a developing agent (including a hydrogen atom).

DETAILED DESCRIPTION OF THE INVENTION $R_1$, $R_2$, $R_3$, and Z in the above general formula (I) will now be described in greater detail below.

In the general formula (I), $R_1$ represents a straight chain, branched chain or cyclic aliphatic group, preferably having from 1 to 32 carbon atoms (for example, a methyl group, a butyl group, a pentadecyl group, a cyclohexyl group, an allyl group, etc.), an aromatic group (for example, a phenyl group, a naphthyl group, etc.), or a heterocyclic group (for example, a 2-pyridyl group, a 3-pyridyl group, a 4-pyridyl group, a 2-furyl group, a 2-oxazolyl group, etc.), or a substituted amino group. These groups can be substituted with one or more substituents selected from an alkyl group, an aryl group for example, a phenyl group, a naphthyl group, etc.) an alkoxy group (for example, a methoxy group, a myristyloxy group, a methoxyethoxy group, etc.), an aryloxy group (for example, a phenoxy group, a 2,4-di-tert-amylphenoxy group, a 3-tert-butyl-4-hydroxy phenoxy group, a naphthyloxy group, etc.), a carboxy group, an alkyl carbonyl group (for example, an acetyl group, a tetradecanoyl group, etc.), an arylcarbonyl group (for example, a benzoyl group, etc.), an alkoxycarbonyl group (for example, a methoxycarbonyl group, a benzyloxycarbonyl group, etc.), an aryloxycarbonyl group (for example, a phenoxycarbonyl group, a p-tolyloxycarbonyl group, etc.), an acyloxy group (for example, an acetoxy group, a benzoyloxy group, a phenylaminocarbonyloxy group, etc.), a sulfamoyl group (for example, an N-ethylsulfamoyl group, an N-octadecylsulfamoyl group, etc.), a carbamoyl group (for example, an N-ethylcarbamoyl group, an N-methyldodecyl carbamoyl group, etc.), a sulfonamido group (for example, a methanesulfonamido group, a benzenesulfonamido group, an ethylaminosulfonamido group, etc.), an acylamino group (for example, an acetylamino group, a benzamido group, an ethoxycarbonylamino group, a phenylaminocarbonylamino group, etc.), a diacylamino group (for example, a succinimido group, a hydantoinyl group, etc.), a sulfonyl group, (for example, a methanesulfonyl group, etc.), a hydroxy group, a cyano group, a nitro group, and a halogen atom. When an alkyl group is substituted with fluorine atoms, it may be a so-called poly-fluoroalkyl group.

In the general formula (I), $R_2$ and $R_3$ each preferably represents a straight chain, branched chain or cyclic alkyl group preferably having from 1 to 22 carbon atoms (for example, a methyl group, an ethyl group, a butyl group, a heptyl group, a nonyl group, a heptadecyl group, a cyclohexyl group, etc.), an alkenyl group (for example, an allyl group, etc.), an aryl group (for example, a phenyl group, a naphthyl group, etc.) or a heterocyclic group (for example, a 2-pyridyl group, a 2-imidazolyl group, a 2-furyl group, a 6-quinolyl group, etc.). The alkyl group, alkenyl group, aryl group or heterocyclic group contained these groups for $R_2$ or $R_3$ may be substituted with one or more substituents as described for $R_1$ above.

Further, $R_2$ and $R_3$ may combine with each other to form a ring (for example, a saturated or unsaturated hydrocarbon ring or hetero ring), preferably a 5-membered to 7-membered ring. Specific examples of the ring include a cyclohexane ring.

In the general formula (I), specific examples for the group represented by X include a hydrogen atom, a halogen atom (for example, a fluorine atom, a chlorine atom, a bromine atom, etc.), an alkoxy group (for example, an ethoxy group, a dodecyloxy group, a methoxyethylcarbamoylmethoxy group, a carboxypropoxy group, a methylsulfonylethoxy group, etc.), an aryloxy group (for example, a 4-chlorophenoxy group, a 4-methoxyphenoxy group, a 4-carboxyphenoxy group, 4-methylphenoxy, etc.), an acyloxy group (for example, an acetoxy group, a tetradecanoyloxy group, a benzoyloxy group, etc.), a sulfonyloxy group (for example, a methanesulfonyloxy group, a toluenesulfonyloxy group, etc.), an amido group (for example, a dichloroacetylamino group, a heptafluorobutyrylamino group, a methanesulfonylamino group, a toluenesulfonylamino group, etc.), an alkoxycarbonyloxy group (for example, an ethoxycarbonyloxy group, a benzyloxycarbonyloxy group, etc.), an aryloxycarbonyloxy group (for example, a phenoxycarbonyloxy group, etc.), an aliphatic or aromatic thio group (for example, an ethylthio group, a phenylthio group, a tetrazolylthio group, etc.), an imido group (for example, a succinimido group, a hydantoinyl group, etc.), an aromatic azo group (for example, a phenylazo group, etc.) and the like. These releasing groups may contain a photographically useful group.

In the general formula (I), X is preferably a hydrogen atom, a halogen atom, an aryloxy group, an arylthio group, an alkoxy group or a sulfonamido group. Among them, a hydrogen atom, a fluorine atom, a chlorine atom and an aryloxy group are particularly preferred.

$R_1$ in the general formula (I) may be a divalent group to form a bis coupler or a polymer coupler.

In the general formula (I), $R_1$ is more preferably an alkyl group having from 3 to 22 carbon atoms or an aryl group. $R_2$ and $R_3$ each is more preferably an alkyl group having from 1 to 16 carbon atoms, and an alkylene group having from 4 to 11 carbon atoms when $R_2$ and $R_3$ are combined with each other to form a ring. The alkyl group or aryl group may be substituted with one or more substituents as described for $R_1$ above. X is more preferably a hydrogen atom, a chlorine atom, or an aryloxy group.

In the general formula (I), further more preferred $R_1$ is an aryl group, further more preferred $R_2$ and $R_3$ are each an alkyl group having from 1 to 9 carbon atoms, and an alkylene group having from 4 to 7 carbon atoms when $R_2$ and $R_3$ are combined with each other to form a ring, and further more preferred X is a chlorine atom and a substituted phenoxy group.

In the general formula (I), particularly preferred $R_1$ is a substituted phenyl group. As a substituent for the phenyl group, a sulfonamido group and a carbonamido group are preferred, and a sulfonamido group substituted at the metha-position thereof and a carbonamido group substituted at the ortho-position thereof are particularly preferred.

Particularly preferred $R_2$ and $R_3$ are each an alkyl group having from 1 to 4 carbon atoms, and a tetramethylene group or a pentamethylene group when $R_2$ and $R_3$ are combined with each other to form a ring, and a methyl group and a pentamethylene group are further preferred for $R_2$ or $R_3$.

With respect to 4-hydroxy-5-acylaminooxyindole couplers, a 3-position monoalkyl substituted compound (Compound No. 3) and a 3-position unsubstituted compound (Compound No. 4) are described in U.S. Pat. No. 4,430,423 as mentioned above. However, these couplers tend to form yellow stain in unexposed white background areas due to light and heat, although color images formed therefrom have good fastness to light and heat.

As the result of intensive investigations for eliminating such a problem, it has been found that stability of coupler to light and heat is improved and the stain in unexposed white background areas is remarkably reduced by using the cyan dye forming coupler represented by the general formula (I) described above. Since such an effect is neither disclosed nor suggested in U.S. Pat. No. 4,430,423, the present invention is novel and surprising.

Specific examples of the representative cyan dye forming couplers according to the present invention are set forth below, but the present invention should not be construed as being limited thereto.

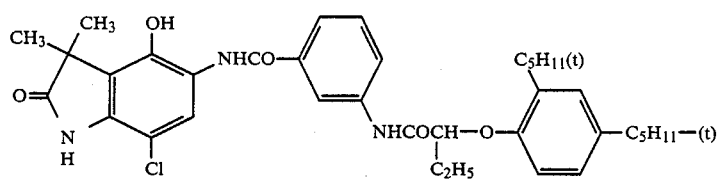

(1)

-continued
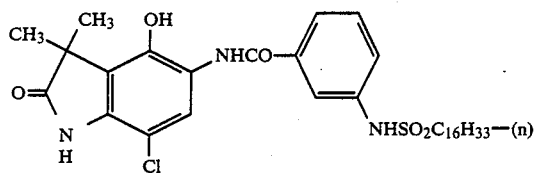 (2)
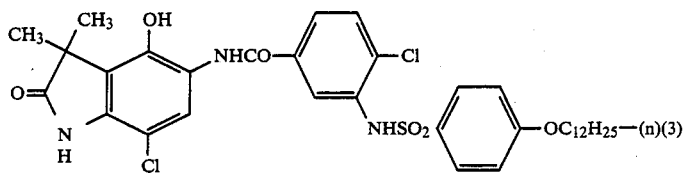 (3)
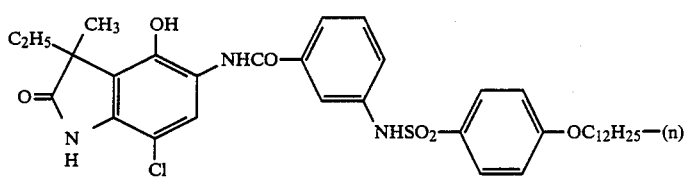 (4)
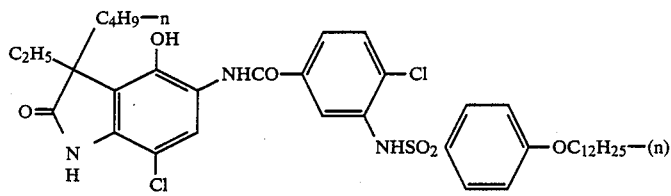 (5)
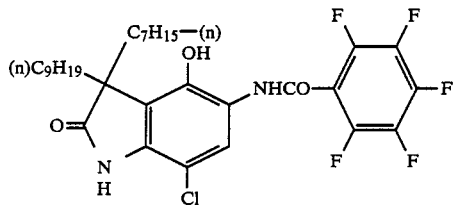 (6)
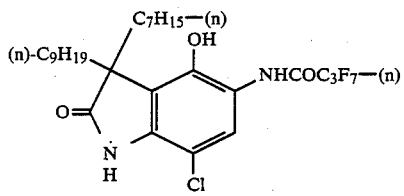 (7)
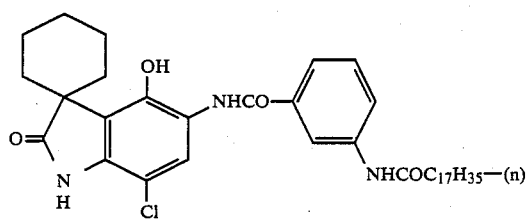 (8)
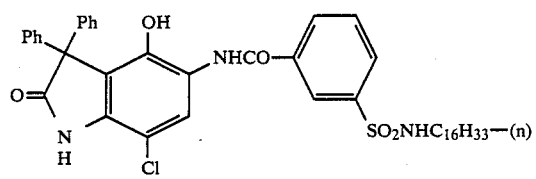 (9)

-continued
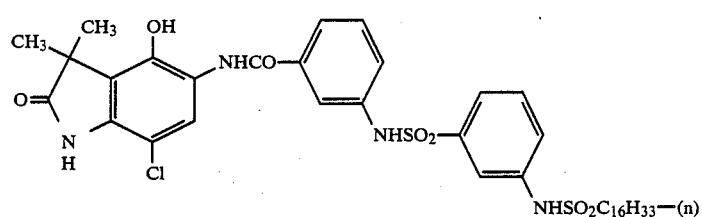
(10)
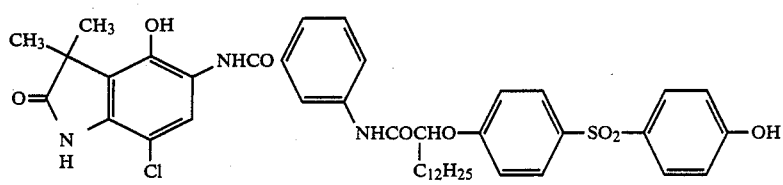
(11)
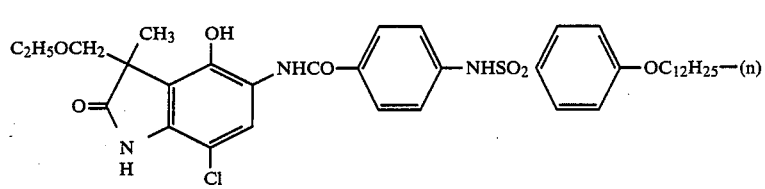
(12)
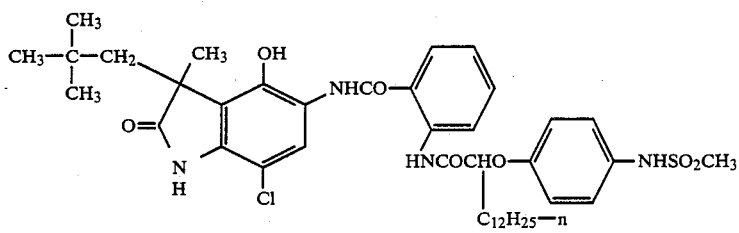
(13)
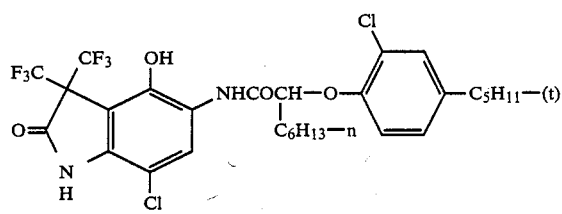
(14)
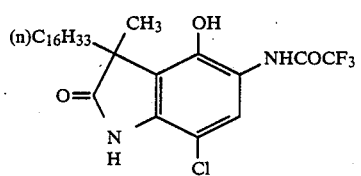
(15)
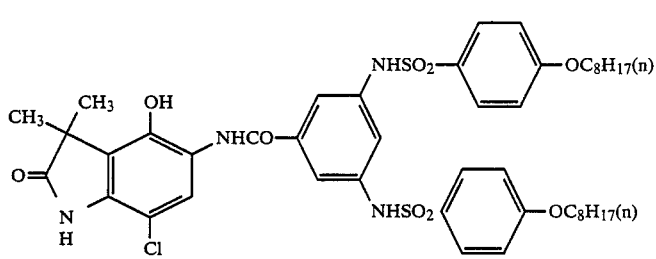
(16)

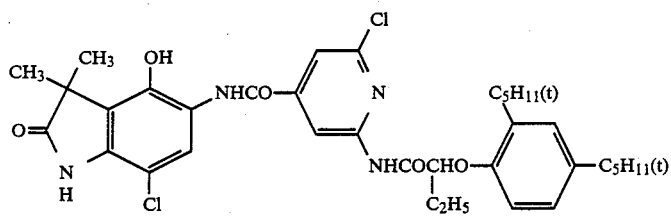 (17)
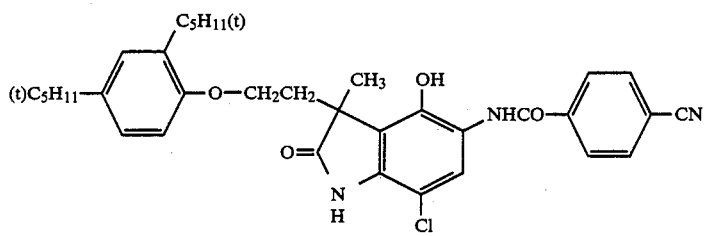 (18)
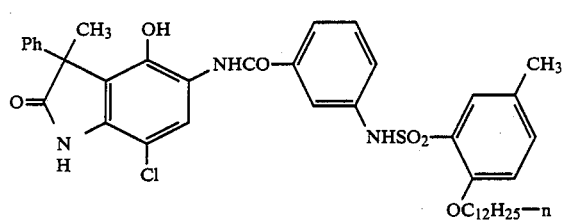 (19)
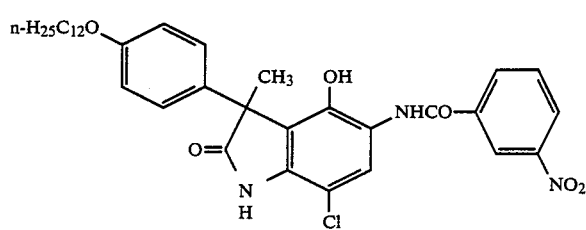 (20)
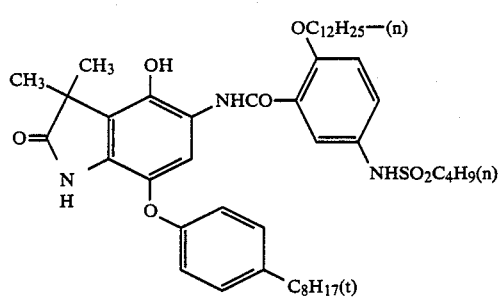 (21)
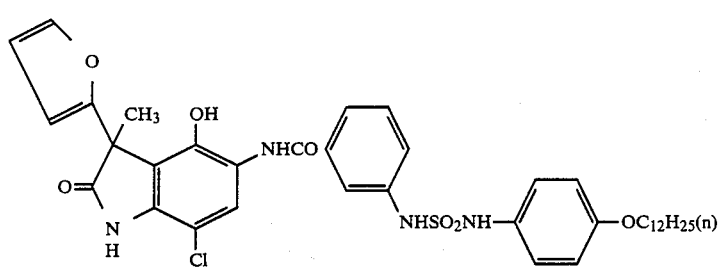 (22)

-continued
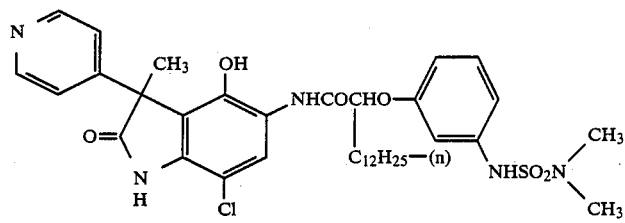
(23)
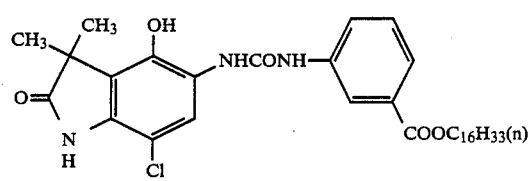
(24)
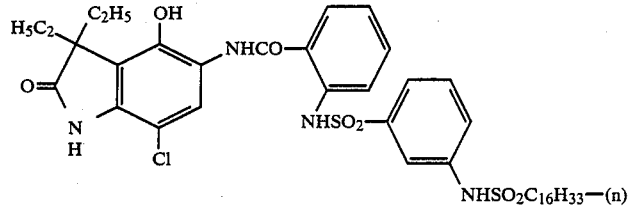
(25)
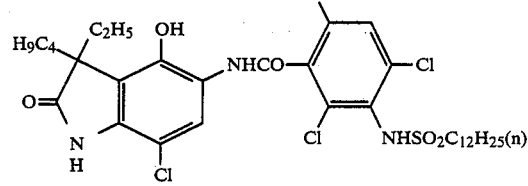
(26)
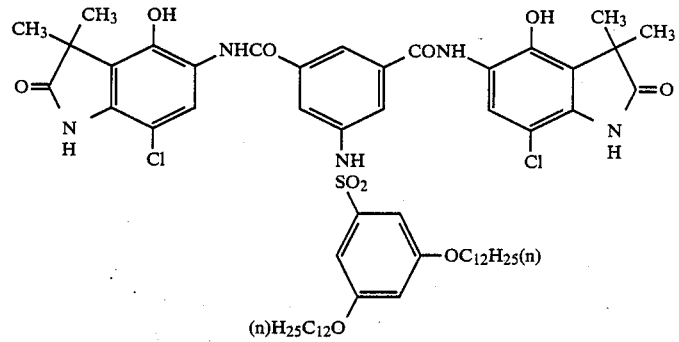
(27)
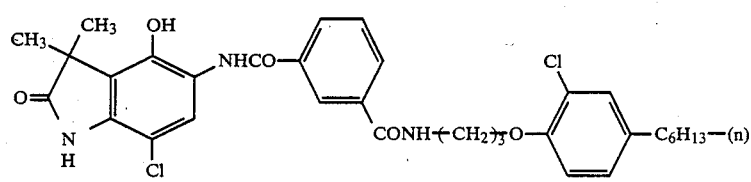
(28)
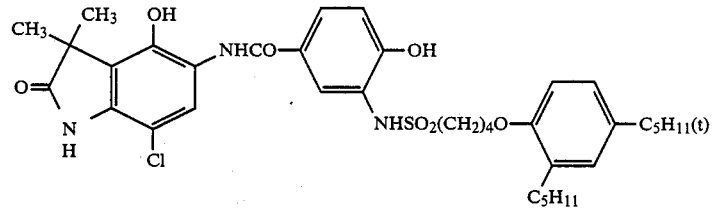
(29)

-continued
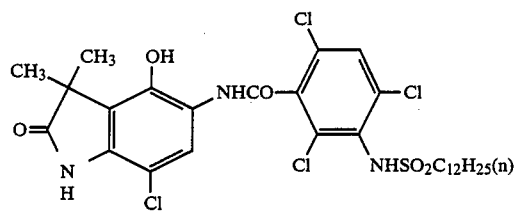 (30)
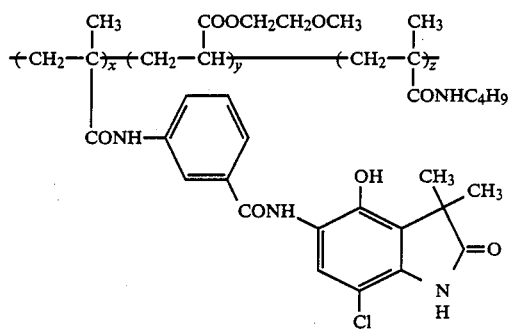 (31)
x:y:z = 60:30:10 (weight ratio)
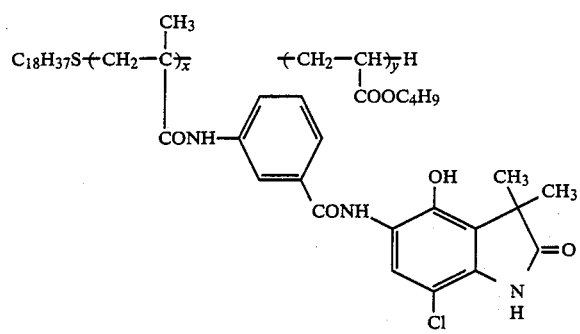 (32)
C$_{18}$H$_{37}$SH:x:y: = 1:3:10 (molar ratio)
Number average molecular weight = 2,000
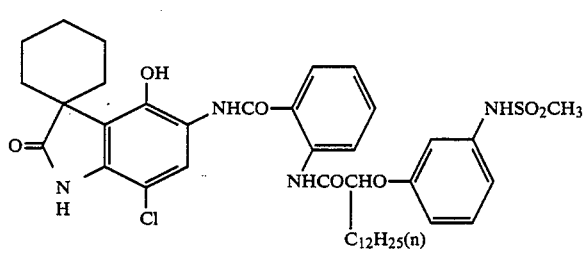 (33)
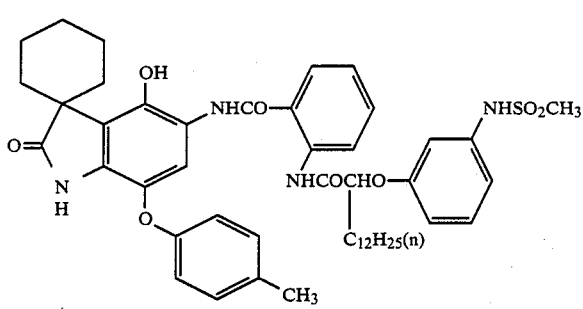 (34)

-continued
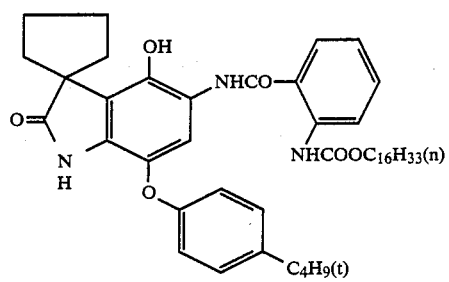
(35)
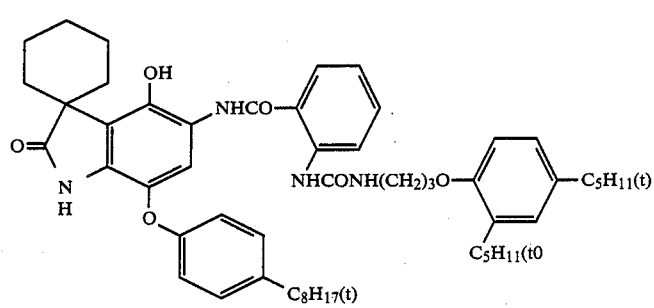
(36)
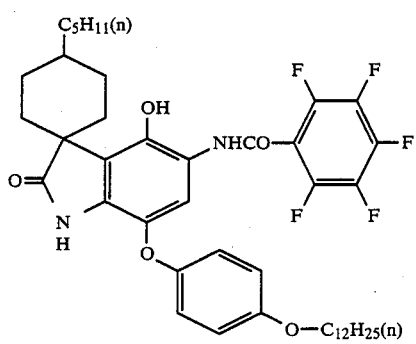
(37)
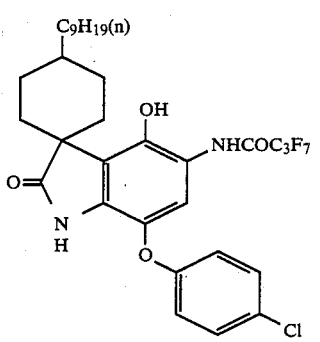
(38)
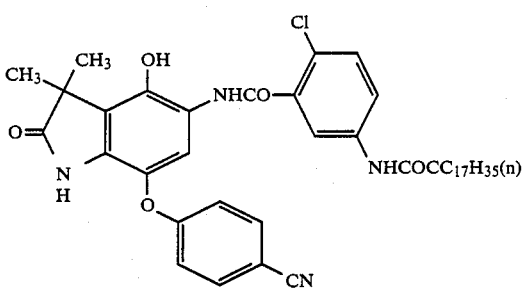
(39)

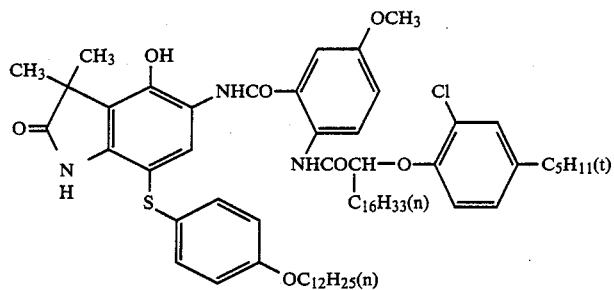
(40)
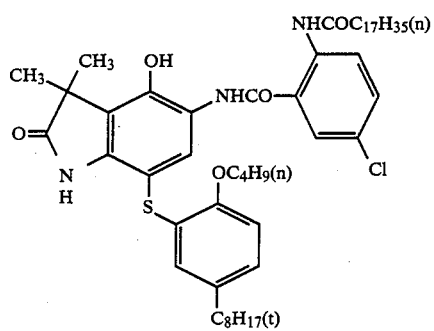
(41)
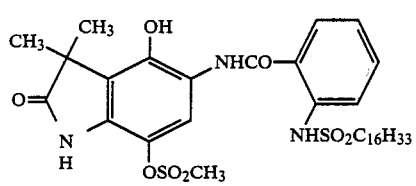
(42)
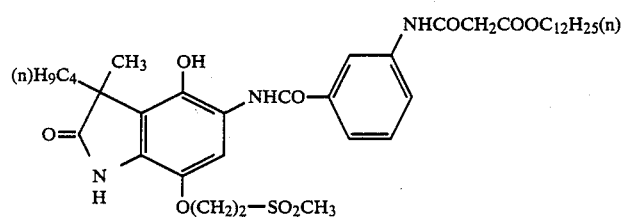
(43)
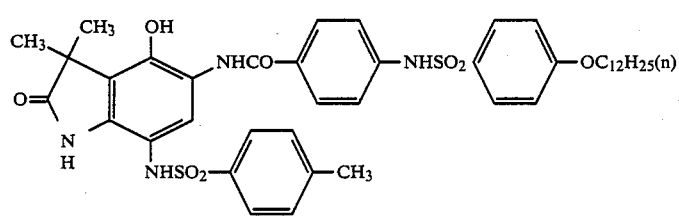
(44)
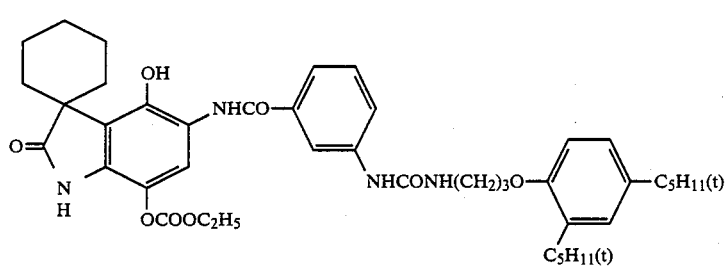
(45)

-continued
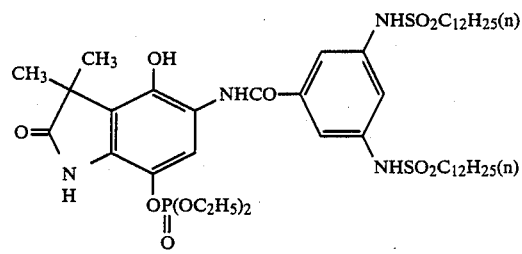 (46)
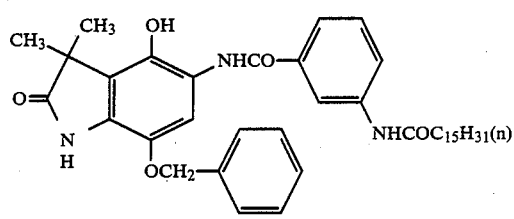 (47)
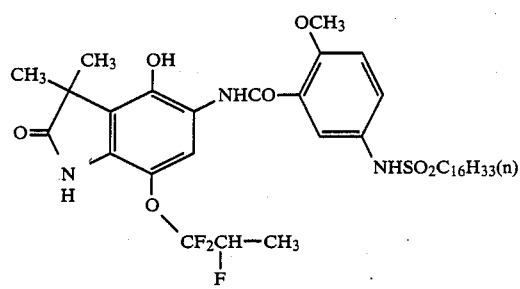 (48)
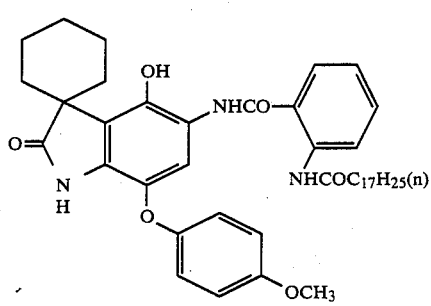 (49)
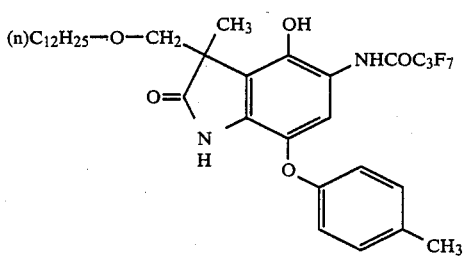 (50)
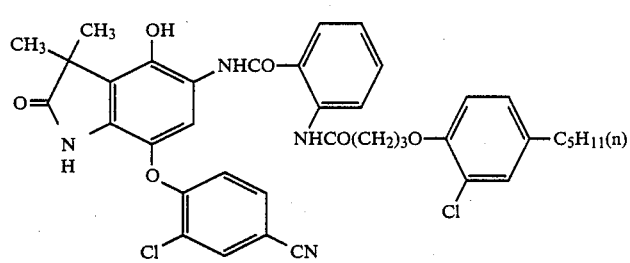 (51)

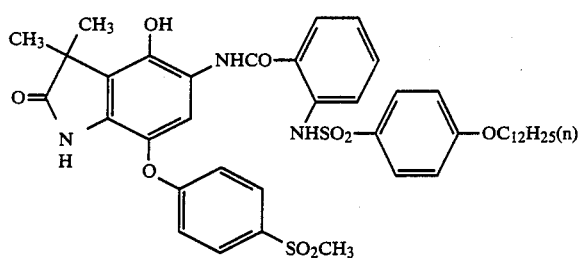
(52)
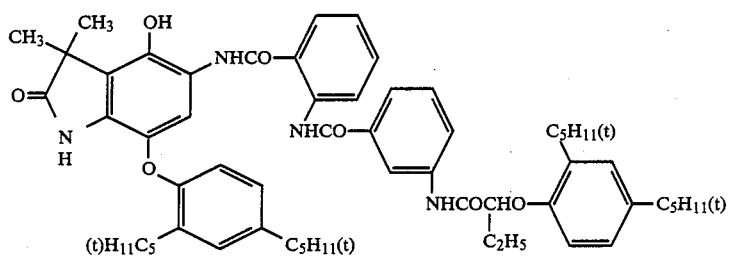
(53)
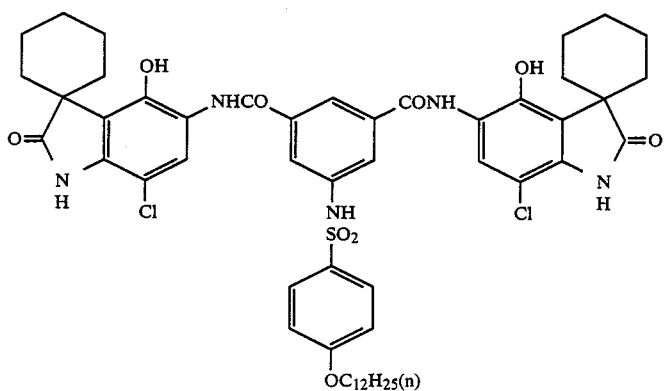
(54)
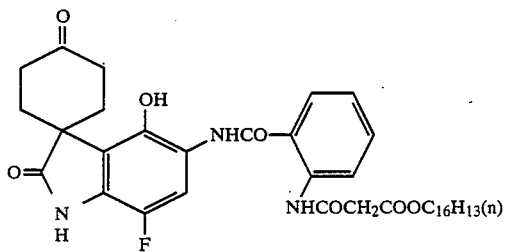
(55)
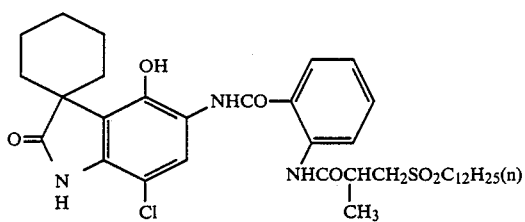
(56)

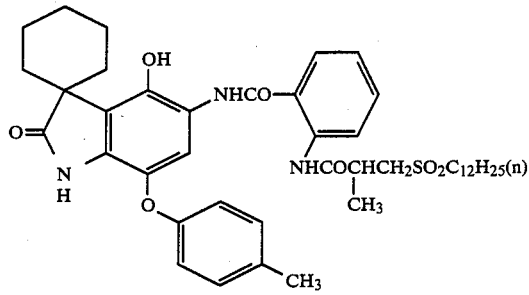

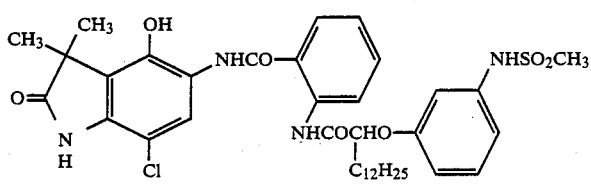

Typical synthesis method and synthesis example of the coupler according to the present invention are illustrated below.

A 5-amino-4-hydroxyoxyindole derivative which is a mother skeleton of the coupler can be synthesized according to a route schematically shown below.

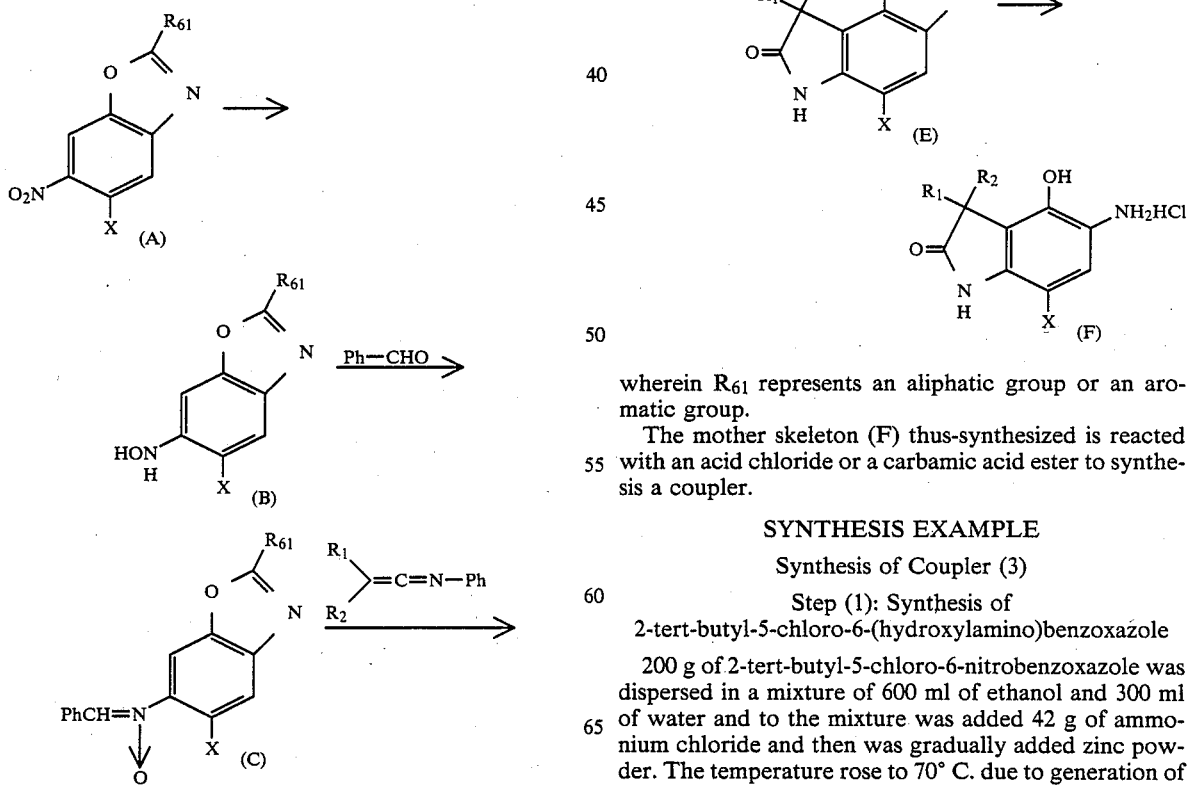

wherein $R_{61}$ represents an aliphatic group or an aromatic group.

The mother skeleton (F) thus-synthesized is reacted with an acid chloride or a carbamic acid ester to synthesis a coupler.

SYNTHESIS EXAMPLE

Synthesis of Coupler (3)

Step (1): Synthesis of 2-tert-butyl-5-chloro-6-(hydroxylamino)benzoxazole 200 g of 2-tert-butyl-5-chloro-6-nitrobenzoxazole was dispersed in a mixture of 600 ml of ethanol and 300 ml of water and to the mixture was added 42 g of ammonium chloride and then was gradually added zinc powder. The temperature rose to 70° C. due to generation of heat. The mixture was stirred for one hour and then, the inorganic substances were removed by filtration. To the filtrate was added 1.8 liters of water, and the crystals thus deposited were collected by filtration. The crystals were dried to obtain 153 g of the desired compound.

Step (2): Synthesis of N-benzylidene-6-(2-tert-butyl-5-chlorobenzoxazolyl-)amino N-oxide 30 g of the crystals obtained in Step (1) and 13 g of benzaldehyde were dispersed in 120 ml of toluene and to the mixture were added 26 g of phosphorus pentaoxide and then 0.7 ml of water. After stirring for 2 hours at room temperature, the reaction solution was poured into ice water containing 26 g of sodium carbonate, extracted with ethyl acetate, washed with water, and the solvent was distilled off under a reduced pressure. To the residue was added hexane, and the crystals deposited were collected by filtration and dried to obtain 32 g of the desired compound as light yellow crystals.

Step (3): Synthesis of 2-tert-butyl-5-chloro-8,8-dimethyl-7-oxopyrolino[2,3-g]benzoxazole 31 g of the crystals obtained in Step (2) was dissolved in 120 ml of toluene, and to the solution was added dropwise 13.8 g of N-phenyl-dimethylketeneimine. After the dropwise addition, the mixture was stirred by heating at 80° C. for 1 hour and the toluene was distilled off under a reduced pressure. The residue was dissolved in 150 ml of ethanol and to the solution was added 15 ml of concentrated hydrochloric acid at room temperature. After stirring the mixture for 30 minutes, the crystals deposited were collected by filtration. The crystals were dried to obtain 18.5 g of the desired compound as light yellow crystals.

Step (4): Synthesis of 5-amino-7-chloro-3,3-dimethyl-4-hydroxyoxyindole hydrochloride 14 g of the crystals obtained in Step (3) was dispersed in a mixture of 15 ml of ethanol, 15 ml of sulforane and 30 ml of concentrated hydrochloric acid, and the mixture was stirred by heating at a range from 80° C. to 90° C. for 15 hours under a nitrogen atmosphere. After the completion of the reaction, the reaction mixture was cooled to room temperature, to which was added 50 ml of acetonitrile. The crystals thus-deposited were collected by filtration and dried to obtain 8.0 g of the desired hydrochloride.

Step (5): Synthesis of Coupler (3)

8.0 g of the hydrochloride obtained in step (4) was dispersed in a mixture of 40 ml of acetonitrile and 20 ml of dimethylacetamide, and to the mixture was added 15.6 g of 4-chloro-3-(4'-dodecyloxyphenylsulfonamido)benzoyl chloride at 80° C. After stirring by heating at 80° C. for 30 minutes, the reaction mixture was cooled to room temperature, to which was added water and extracted with ethyl acetate. The extract was washed with water and concentrated under a reduced pressure. To the residue were added 40 ml of acetonitrile and 10 ml of ethyl acetate to crystalize, whereby 15.0 g of the desired Coupler (3) was obtained.

| Melting Point: 168 to 170° C. | | | |
|---|---|---|---|
| Elemental analysis: | H (%) | C (%) | N (%) |
| Calculated | 6.12 | 59.59 | 5.93 |
| Found | 6.15 | 59.65 | 5.96 |

The couplers can be synthesized in a manner similar to the above.

Two or more kinds of the couplers according to the present invention can be used in combination or the coupler according to the present invention can be used together with a coupler other than the present invention in the same layer or one and other layers which are sensitive to substantially the same region of light. Cyan couplers which can be preferably used in combination with the coupler according to the present invention can be represented by the following general formula (V):

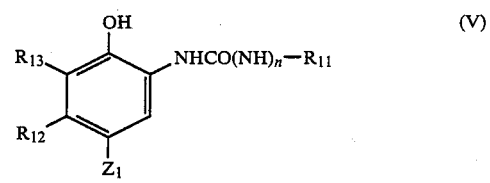

wherein $R_{11}$ represents a substituted or unsubstituted aliphatic group, a substituted or unsubstituted aryl group or a substituted or unsubstituted heterocyclic group; $R_{12}$ represents a substituted or unsubstituted aliphatic group, a substituted or unsubstituted aryl group or a substituted or unsubstituted acylamino group; $R_{13}$ represents a hydrogen atom, a halogen atom, a substituted or unsubstituted aliphatic group, a substituted or unsubstituted aryl group, a substituted or unsubstituted alkoxy group, a substituted or unsubstituted acylamino group, or $R_{12}$ and $R_{13}$ may be combined with each other to form a nitrogen-containing 5-membered to 7-membered ring. Specific examples of the substituents for the above-described groups include those as described for $R_1$ in the general formula (I) above. $Z_1$ has the same meaning as X defined in the general formula (I); and n represents 0 or 1.

Representative examples of the cyan couplers represented by the general formula (V) are set forth below.

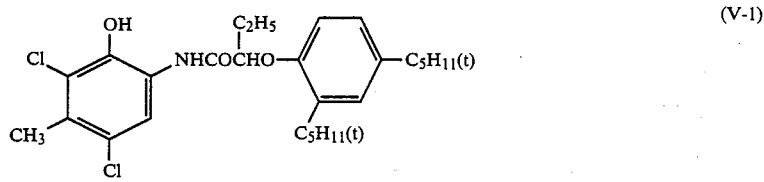

-continued
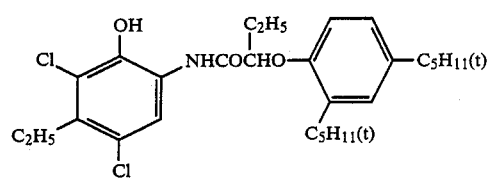 (V-2)
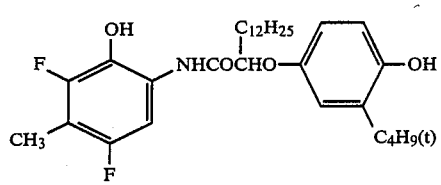 (V-3)
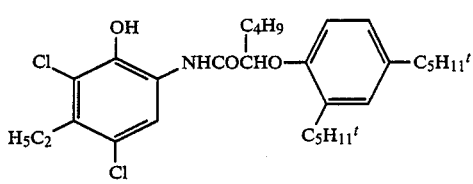 (V-4)
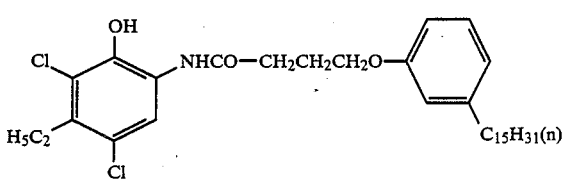 (V-5)
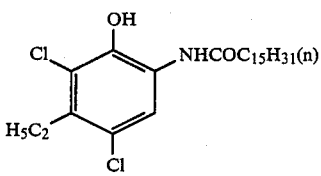 (V-6)
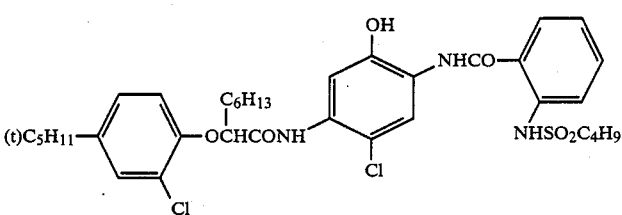 (V-7)
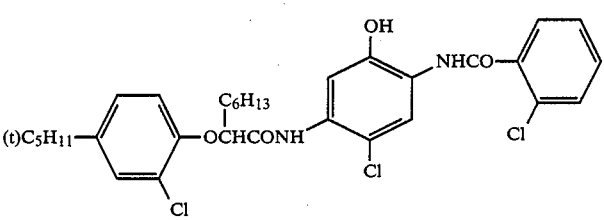 (V-8)
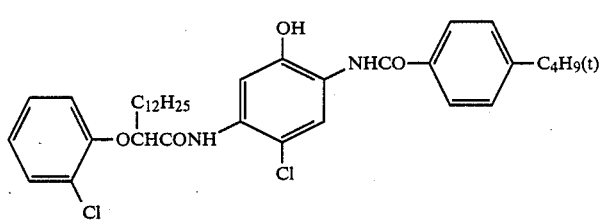 (V-9)

-continued
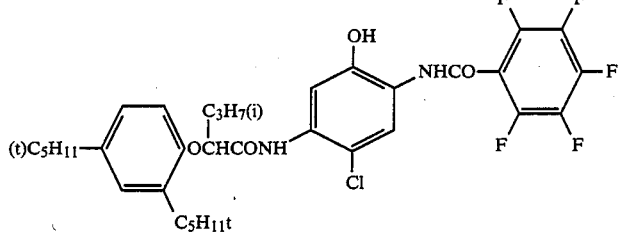 (V-10)
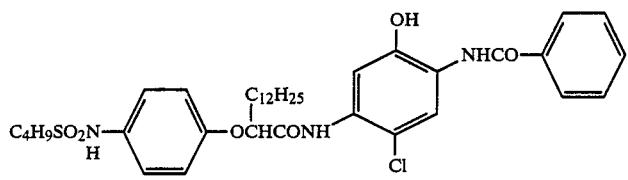 (V-11)
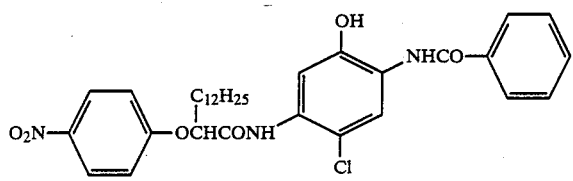 (V-12)
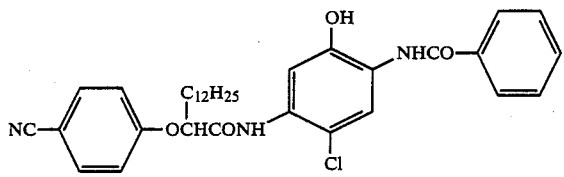 (V-13)
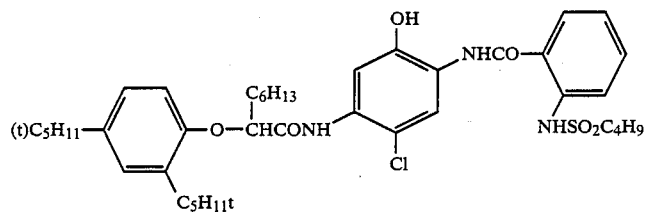 (V-14)
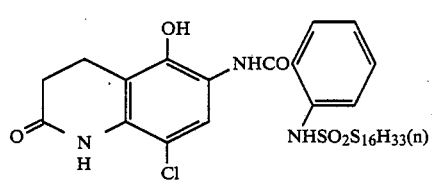 (V-15)
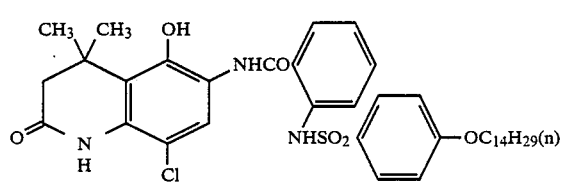 (V-16)
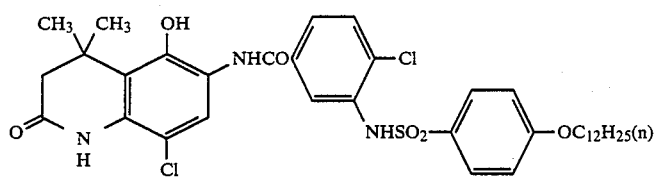 (V-17)

-continued

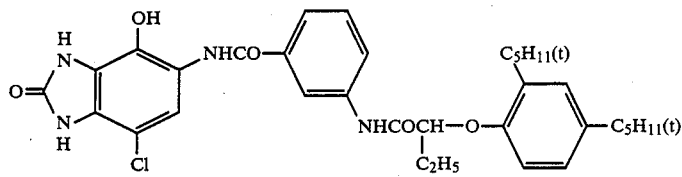
(V-18)

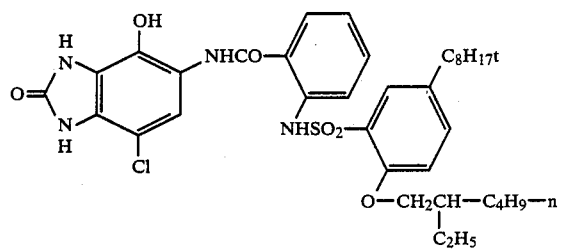
(V-19)

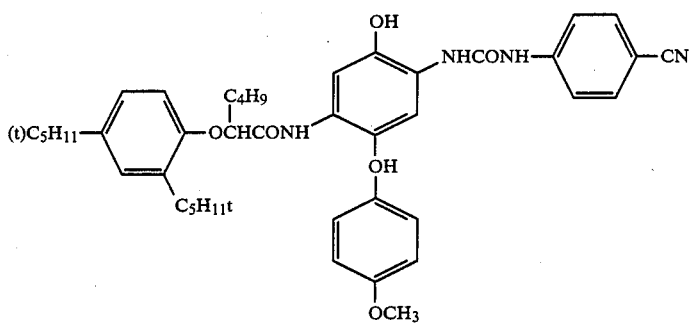
(V-20)

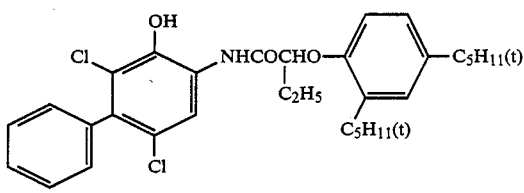
(V-21)

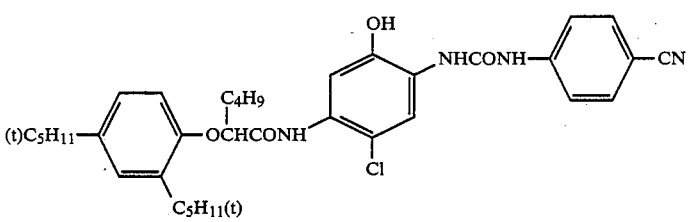
(V-21)

The coupler according to the present invention and other couplers can be introduced into a silver halide emulsion layer by a known method. In this case, with respect to an additive, for example, a coupler solvent, an ultraviolet light absorbing agent, a protective colloid, a binder, an antifogging agent, a color mixing preventing agent, a color fading preventing agent, a sensitizing dye, a dye, a whitening agent, etc., a method for forming a silver halide photographic light-sensitive material, (for example, a method for preparation of photographic emulsion, a method for introduction of coupler, etc., a support, a layer composition of each light-sensitive layer, etc.) and a method of photographic processing, substances and methods as described in Research Disclosure, No. 17643 (Dec., 1978), Industrial Opportunies Ltd., UK, Japanese patent application Ser. (OPI) Nos. 65134/81 and 104333/81 (the term "OPI" as used herein means an "unexamined published application") or the literatures cited therein can be employed.

The amount of the coupler added according to the present invention is usually from 0.1 mol to 1.0 mol, preferably from 0.1 mol to 0.5 mol per mol of silver halide to a silver halide emulsion layer which constitutes a light-sensitive layer.

In the present invention, known magenta couplers and yellow couplers can be introduced into a color photographic light-sensitive material in combination with at least one of the cyan couplers represented by the general formula (I).

Of yellow couplers, acylacetamido derivatives such as benzoylacetanilides or pivaloylacetanilide are preferred.

Among them, those represented by the general formula (VI) or (VII) shown below are more preferred as yellow couplers.

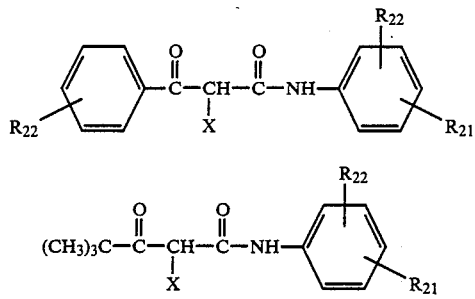

wherein X has the same meaning as defined in the general formula (I); $R_{21}$ represents a diffusion resistant group having from 8 to 32 carbon atoms in total; and $R_{22}$ represents a hydrogen atom, one or more of halogen atoms, lower alkyl groups, lower alkoxy groups or diffusion resistant groups having from 8 to 32 carbon atoms in total, when two or more $R_{22}$'s are present, they may be the same or different.

The pivaloylacetanilide type yellow couplers are described in detail in U.S. Pat. No. 4,622,287, column 3, line 15 to column 8, line 39 and U.S. Pat. No. 4,623,616, column 14, line 50 to column 19, line 41.

The benzoylacetanilide type yellow couplers are described in detail in U.S. Pat. Nos. 3,408,194, 3,933,501, 4,046,575, 4,133,958 and 4,401,752, etc.

More specifically, Compounds (Y-1) to (Y-39) as described in the above mentioned U.S. Pat. No. 4,622,287, column 37 to column 54 are suitable. Of the compounds, Compounds (Y-1), (Y-4), (Y-6), (Y-7), (Y-15), (Y-21), (Y-22), (Y-23), (Y-26), (Y-35), (Y-36), (Y-37), (Y-38) and (Y-39) are preferred.

Further, Compounds (Y-1) to (Y-33) as described in the above mentioned U.S. Pat. No. 4,623,616, column 19 to column 24 are suitable. Of these compounds, Compounds (Y-2), (Y-7), (Y-8), (Y-12), (Y-20), (Y-21), (Y-23) and (Y-29) are preferred.

Moreover, Compound (34) as described in U.S. Pat. No. 3,408,194, column 6; Compound (16) and (19) as described in U.S. Pat. No. 3,933,501, column 8 ; Compound (9) as described in U.S. Pat. No. 4,046,575, column 7 to column 8; Compound (1) as described in U.S. Pat. No. 4,133,958, column 5 to column 6; Compound (1) as described in U.S. Pat. No. 4,401,752, column 5, and Compounds (a) to (g) described below are also preferred.

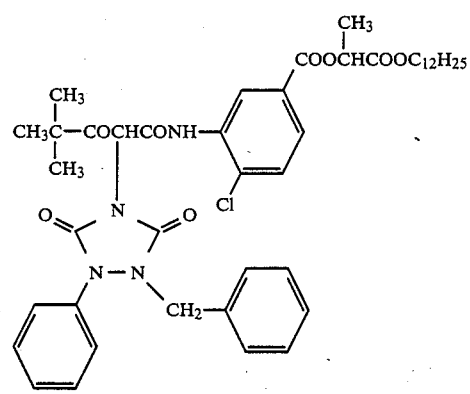

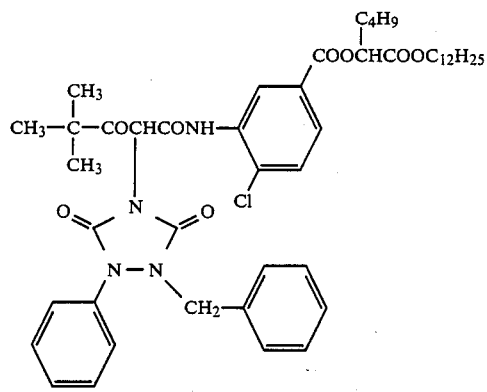

-continued
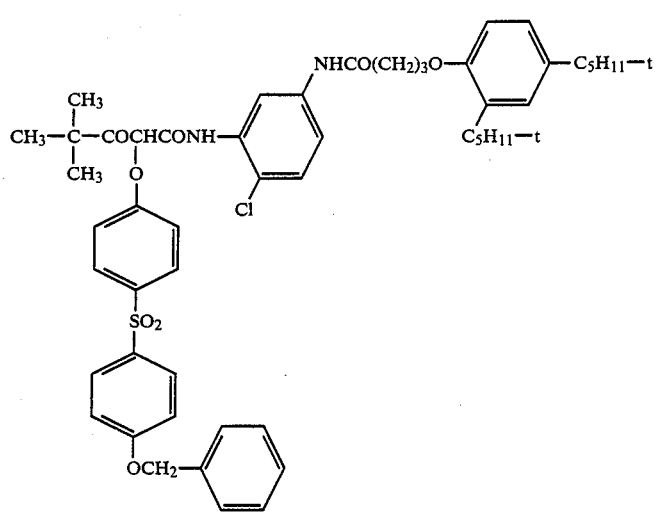
(c)
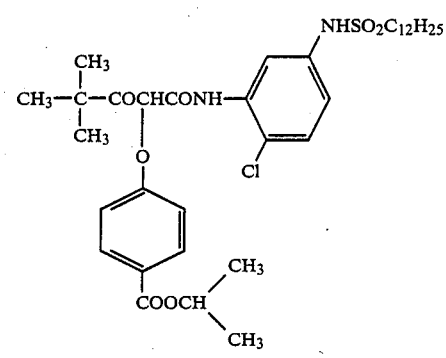
(d)
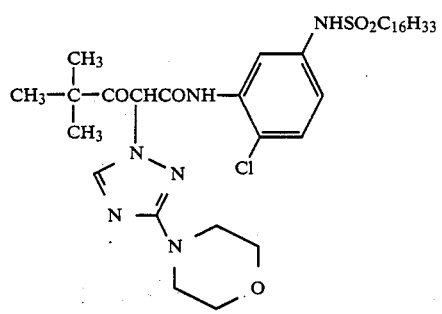
(e)
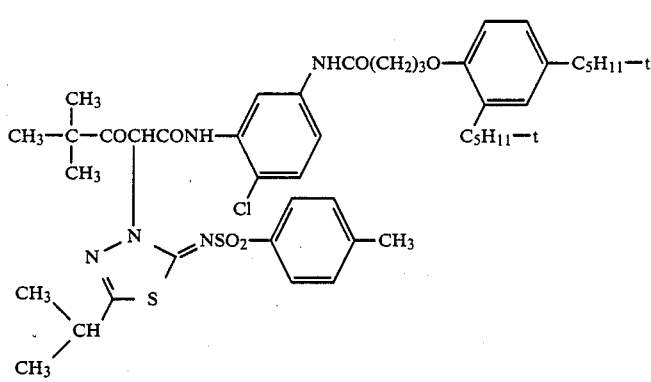
(f)

-continued

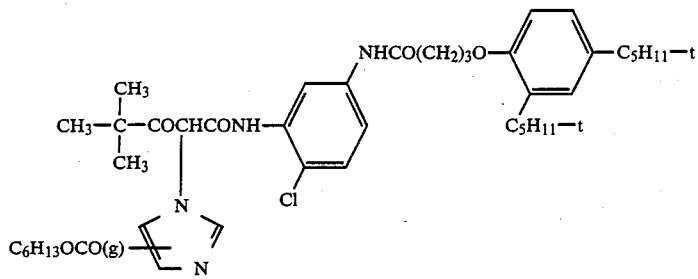

As magenta couplers, 3-anilino-5-pyrazolones, 3-acylamino-5-pyrazolones and pyrazoloazoles (for example, pyrazolopyrazoles, pyrazoloimidazoles, pyrazolotriazoles, pyrazolotetrazoles, etc.) are preferred.

Among them, those represented by the general formula (VIII), (IX) or (X) shown below are more preferred.

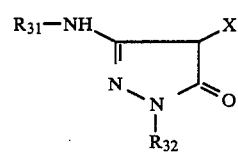 (VIII)

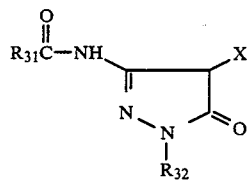 (IX)

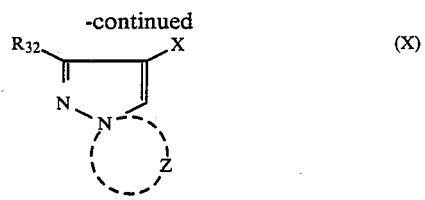 (X)

wherein $R_{31}$ represents a diffusion resistant group having from 8 to 32 carbon atoms in total; $R_{32}$ represents a halogen atom, a substituted or unsubstituted lower alkyl group or lower alkoxy group or a substituted or unsubstituted phenyl group or phenoxy group; and Z represents a non-metallic atomic group necessary to form a 5-membered azole ring containing two to four nitrogen atoms, which azole ring may have one or more substituents (including a condensed ring).

The substituents in the above described general formulae and polymer components are described in detail in U.S. Pat. No. 4,622,287, column 3 to column 6 and U.S. Pat. No. 4,540,654, column 2, line 41 to column 8, line 27.

Specific examples of pyrazoloazole type couplers include Compounds (M-16) to (M-39) as described in Japanese patent application No. 32462/86, pages 345 to 350 and Compounds (M-41) to (M-47) as described in ibid, pages 351 to 353. Of these compounds, those illustrated below are more preferred.

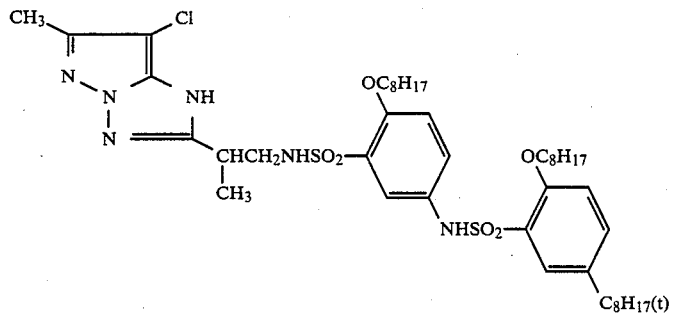

(M-1)

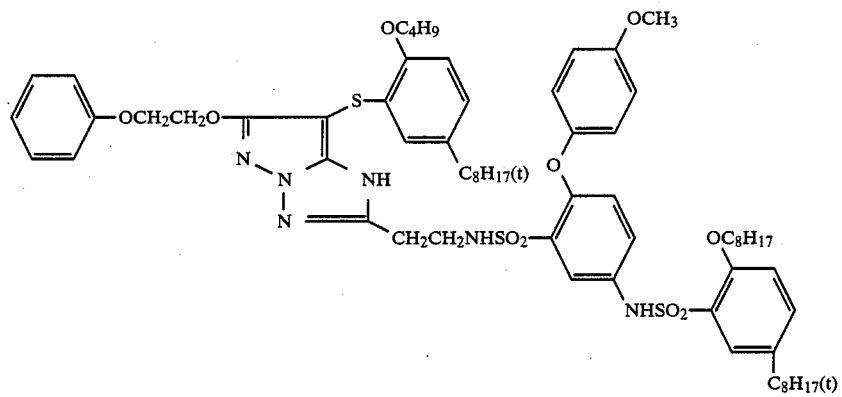
(M-2)
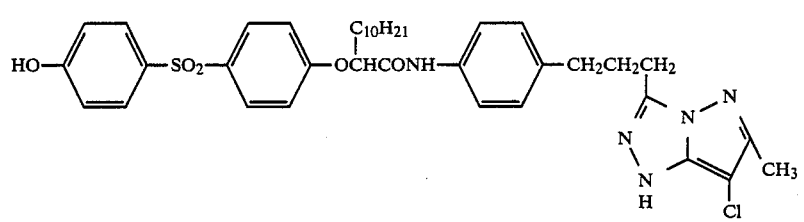
(M-3)
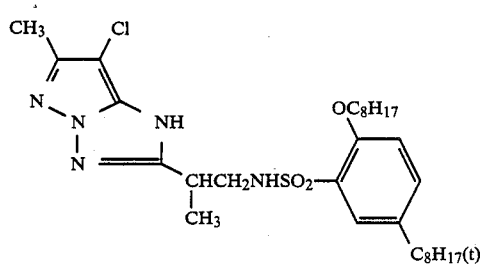
(M-4)
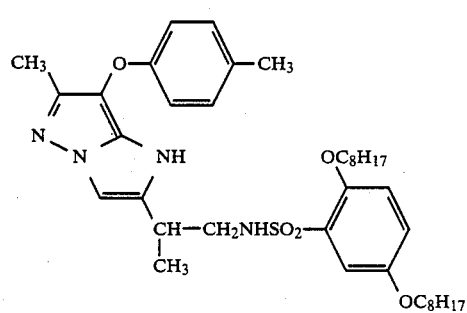
(M-5)
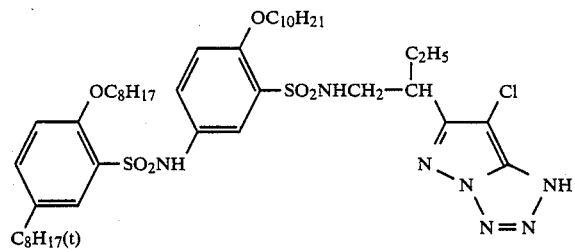
(M-6)

-continued
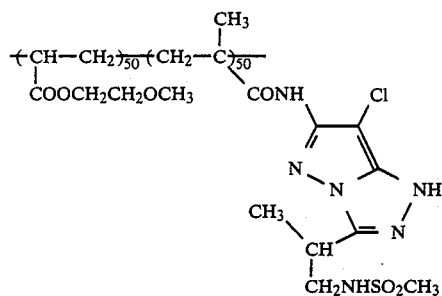 (M-7)
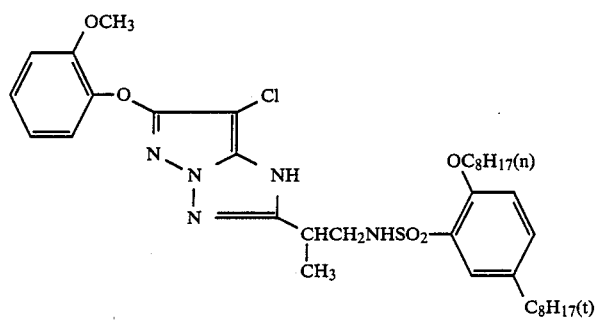 (M-8)
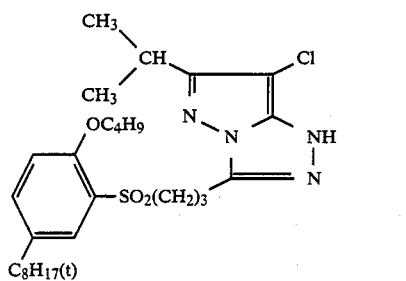 (M-9)
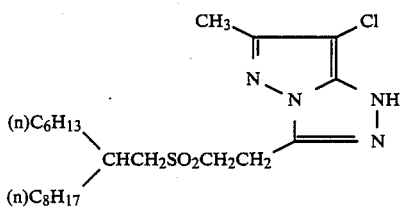 (M-10)
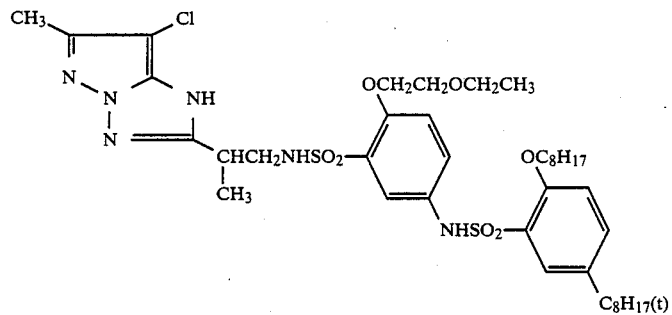 (M-11)

-continued

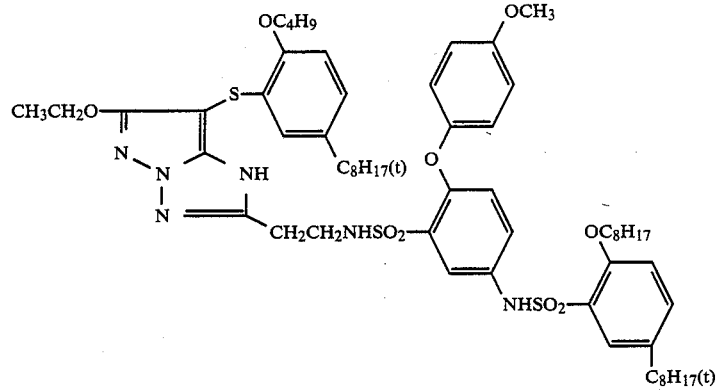
(M-12)

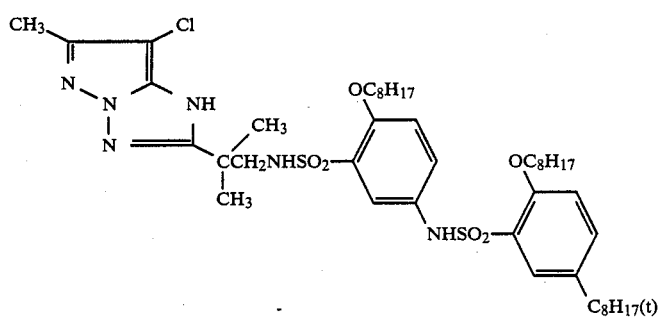
(M-13)

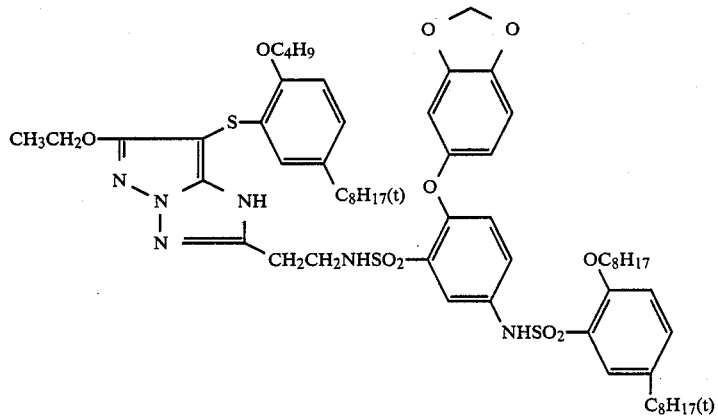
(M-14)

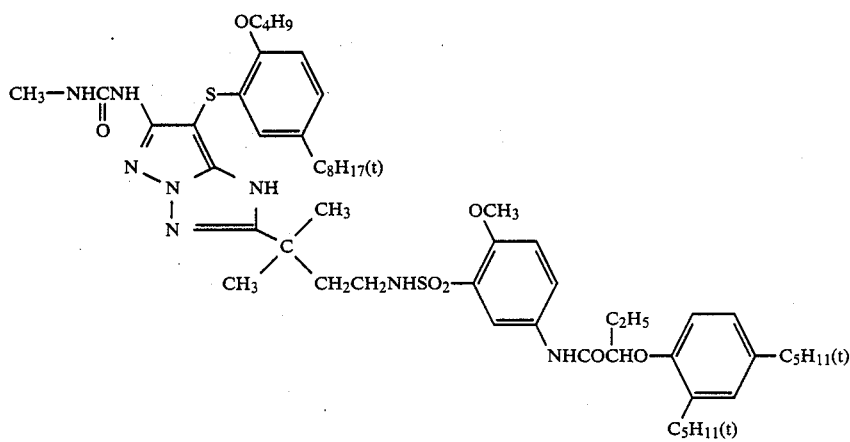
(M-15)

As high-boiling organic solvents which can be used in the present invention, those having a boiling point of about 160° C. or above at a normal pressure are preferred. For examples, esters (for example, phosphonic acid esters, phthalic acid esters, fatty acid esters, benzoic acid esters, etc.), phenols, aliphatic alcohols, carboxy acids, ethers, amides (for example, fatty acid amides, benzoic acid amides, sulfonic acid amides, cyclic imides, etc.), aliphatic hydrocarbons, halogenated compounds, sulfone derivatives, etc. are exemplified. In order to dissolve photographic additives such as couplers in the high-boiling organic solvent, a low-boiling organic solvent having a boiling point of from about 30° C. to about 160° C., such as a lower alkyl ester (for example, ethyl acetate, butyl acetate, ethyl propionate, etc.), secondary butyl alcohol, methyl isobutyl ketone, cyclohexanone, β-ethoxyethyl acetate, dimethylformamide, etc. may be added together, if desired. The mixture was emulsified and dispersed in an aqueous solution of hydrophilic colloid, and the emulsified dispersion is mixed with a photographic emulsion. It is possible to remove the low-boiling organic solvent along according to condensation under a reduced pressure or washing with water, etc.

When the cyan coupler of the present invention is added to a photographic emulsion, it is not always necessary to use the above-described high-boiling organic solvent. However, the use of such the high-boiling organic solvent is favorable. The amount of high-boiling organic solvent used is less than 20 parts, preferably from 0.2 part to 3 parts to a photographic additive such as a coupler.

Preferred specific examples of the high-boiling organic solvents are set forth below.

| Compound | | |
|---|---|---|
| | No. | $W_1$ |
| $O=P(W_1)_3$ | 0-1 | $-OCH_2\underset{\underset{C_2H_5}{\|}}{C}HC_4H_9$ |
| | 0-2 | $-OCH_2CH_2\underset{\underset{CH_3}{\|}}{C}HCH_2\underset{\underset{CH_3}{\|}}{\overset{\overset{CH_3}{\|}}{C}}-CH_3$ |
| | 0-3 | $-OC_{12}H_{25}$ |
| | 0-4 | $-OCH_2CH_2OC_4H_9$ |
| | 0-5 | $-O(CH_2)_3Cl$ |
| | 0-6 | $-O-\text{cyclohexyl (H)}$ |
| | 0-7 | $-O-\text{phenyl}$ |
| | 0-8 | $-O-\text{C}_6H_4-CH_3$ (m,p mixture) |
| | 0-9 | $O=P{-O-C_6H_4-i\text{-}C_3H_7}_n{-O-C_6H_5}_{3-n}$, $n = 1, 2, 3$ |

| | No. | $W_2$ | $W_3$ |
|---|---|---|---|
| ortho-disubstituted benzene with $W_2$, $W_3$ | 0-10 | $-COOC_4H_9$ | same as $W_2$ |
| | 0-11 | $-COO-\text{cyclohexyl (H)}$ | " |
| | 0-12 | $-COOC_2H_5$ | $-COOCH_2COOC_2H_5$ |

-continued

| | Compound | |
|---|---|---|
| O-13 | $-COO(CH_2)_9-CH\overset{O}{-}CH_2$ (epoxide) | same as $W_2$ |
| O-14 | $-COOCH_2CHC_4H_9$ with $C_2H_5$ branch | " |
| O-15 | $-COOC_{12}H_{25}$ | " |
| O-16 | $-COOCH_2CH_2OC_4H_9$ | " |
| (O-17) | 2,4-dichlorophenyl-$COOCH_2CHC_4H_9$ with $C_2H_5$ branch | |
| (O-18) | $HO-C_6H_4-SO_2-C_6H_4-OC_{16}H_{33}$ | |
| (O-19) | 4-hydroxy-2,5-di-t-amylphenyl ($HO-, C_5H_{11}(t), C_5H_{11}(t)$) | |
| (O-20) | $(t)C_5H_{11}$-phenyl(-$C_5H_{11}(t)$)-O-$\underset{C_2H_5}{CH}$-CONH-phenyl-COOH | |
| (O-21) | $HO$-phenyl-$COOCH_2CHC_4H_9$ with $C_2H_5$ branch | |
| (O-22) | $HO$-phenyl(Cl)-$SO_2$-phenyl(Cl)-$OC_{16}H_{33}$ | |
| (O-23) | $(t)C_5H_{11}$-phenyl(-$C_5H_{11}(t)$)-$O(CH_2)_3COOH$ | |
| (O-24) | $C_8H_{17}CH\overset{O}{-}CH(CH_2)_7COOC_4H_9$ | |
| (O-25) | cyclohexane with epoxide O, H, and two $COOCH_2CHC_4H_9$ with $C_2H_5$ branches | |

-continued
| | Compound |
|---|---|
| (0-26) | 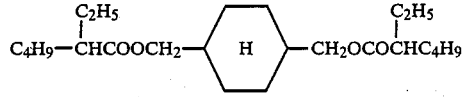 |
| (0-27) | 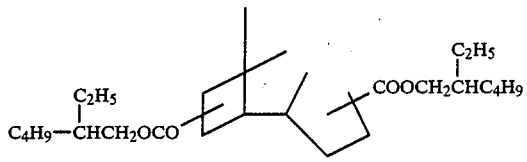 |
| (0-28) | 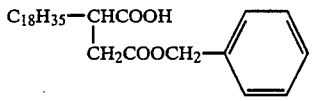 |
| (0-29) |  |
| (0-30) | $C_4H_9CHCH_2OCO(CH_2)_8COOCH_2CHC_4H_9$ with $C_2H_5$ substituents 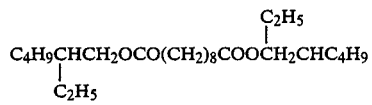 |
| (0-31) | 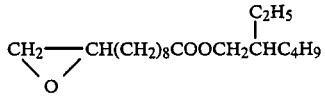 |
| (0-32) | 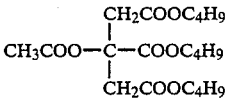 |
| (0-33) | 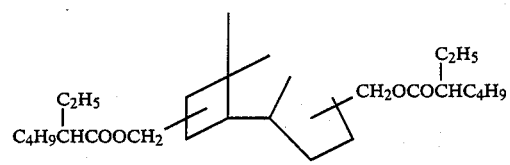 |
| (0-34) | $C_nH_{2n+2}$ (paraffin) n = 10 to 20 |
| (0-35) | $CH_3COCH_2COOC_{12}H_{25}$ |
| (0-36) | 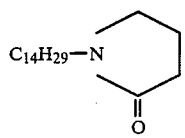 |
| (0-37) | 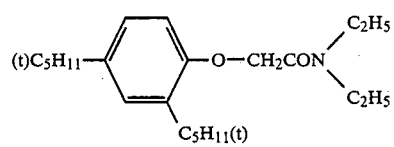 |

-continued

| Compound | |
|---|---|
| (O-38) | 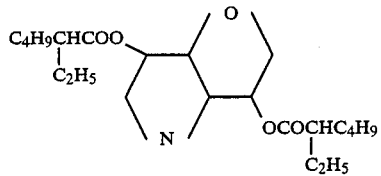 |
| (O-39) | C₁₂H₁₈Cl₈ (chlorinated paraffin) |
| (O-40) | 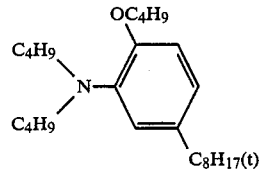<br>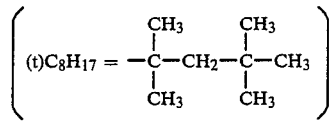 |
| (O-41) | 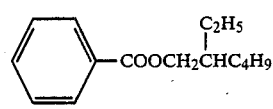 |

Further, couplers can be emulsified and dispersed by a polymer dispersion method as described below.

For instance, a method wherein a coupler and a water-insoluble and organic solvent soluble polymer (such as an alkyl acrylate type polymer) is dissolved in an auxiliary solvent and the solution is dispersed in a hydrophilic collid as described in U.S. Pat. No. 3,619,195; a loadable latex dispersion method wherein a coupler is dissolved in a water-miscible organic solvent and the solution is mixed with a polymer latex whereby the coupler is loaded in the polymer latex (the remaining solvent is removed for sufficient loading) as described in U.S. Pat. No. 4,203,716; other dispersing method using a latex as described in Japanese Patent Publication No. 39853/76; a method using a prepolymer composed of a conjugated diene or a vinyl monomer as a high-boiling organic solvent as described in West German patent application (OLS) No. 2,830,917; a polymer dispersing method as described in Japanese patent application (OPI) No. 25133/76; and a method wherein a monomer is polymerized in the presence of a coupler and dispersed in a hydrophilic binder; etc. are employed.

If desired, special couplers other than the couplers represented by the general formulae described above according to the present invention may be incorporated in the photographic light-sensitive material of the present invention containing the cyan coupler. For example, colored magenta couplers may be incorporated in a green-sensitive emulsion layer to impart a masking effect. Further, development inhibitor-releasing couplers (DIR couplers), development inhibitor-releasing hydroquinones, etc. may be used in emulsion layers of respective color sensitivities or in layers adjacent thereto. Development inhibitors to be released upon the development provide interlayer effects such as improvement of image sharpness, formation of fine-grained image, improvement of monochromatic saturation.

Couplers capable of releasing a development accelerator or a nucleating agent upon development of silver may be added to photographic emulsion layers of the photographic light-sensitive material according to the present invention or layers adjacent thereto to obtain effects of improving photographic sensitivity and graininess of color image, and making gradation contrast.

The cyan coupler according to the present invention can be employed in silver halide color photographic materials for example, color negative films, color paper, color positive films, color reversal films for slide, color reversal films for cinematography, color negative films for cinematography, color reversal paper, direct positive color paper (films), etc.

In the present invention, the effect according to the present invention can be highly achieved by using in combination with at least one ultraviolet light absorbing agent. The ultraviolet light absorbing agents may be added to any layer. Preferably, it is incorporated into a layer containing the cyan coupler according to the present invention or a layer adjacent thereto. Ultraviolet light absorbing agents to be used in the present invention are those compounds which are listed in *Research Disclosure*, No. 17643, VIII-C, and are preferably benzotriazole derivatives represented by the following general formula (XI):

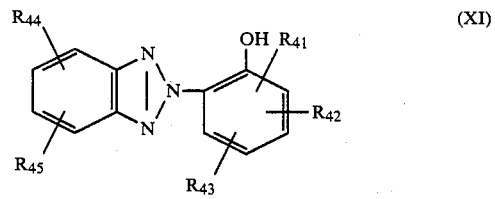

(XI)

wherein $R_{41}$, $R_{42}$, $R_{43}$, $R_{44}$, and $R_{45}$, which may be the same or different, each represents a hydrogen atom or a substituent acceptable for the aliphatic group or aromatic group represented by $R_1$ in the general formula (I), or $R_{44}$ and $R_{45}$ may combine with each other to form a 5-membered or 6-membered aromatic ring composed of carbon atoms. These groups and aromatic ring may further be substituted with one or more substituents.

The compound represented by the general formula (XI) may be used alone or in combination of two or more. Typical examples of the ultraviolet light absorbing agent used in the present invention are set forth below. In the following, the chemical structure of

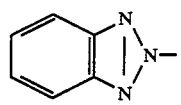

skeleton may form

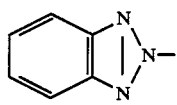

structure due to tautomerism.

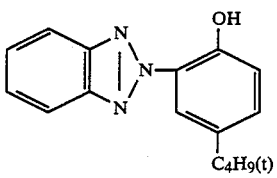 (UV-1)

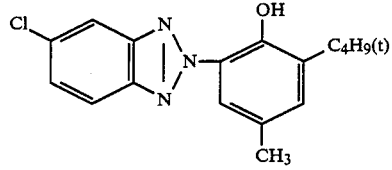 (UV-2)

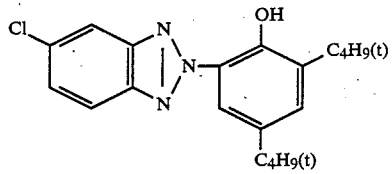 (UV-3)

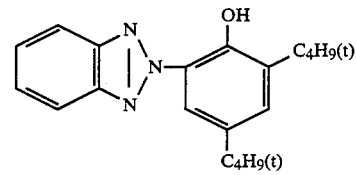 (UV-4)

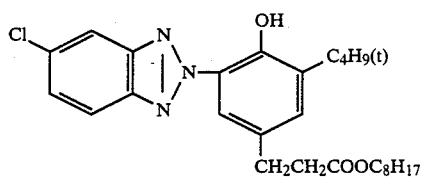 (UV-5)

-continued

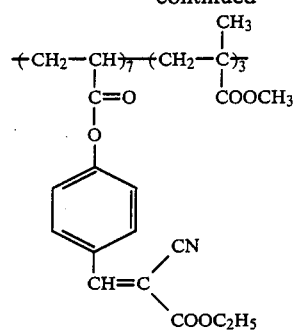 (UV-6)

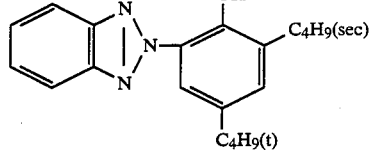 (UV-7)

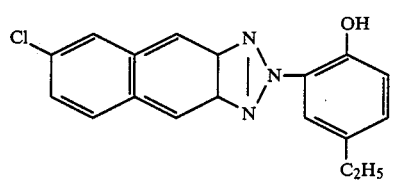 (UV-8)

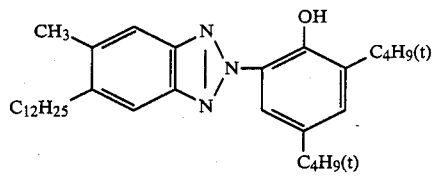 (UV-9)

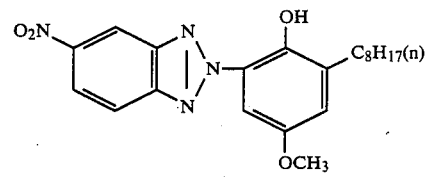 (UV-10)

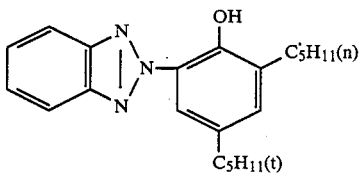 (UV-11)

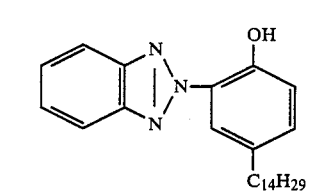 (UV-12)

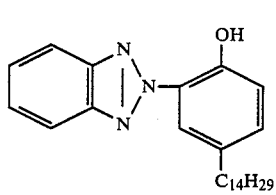 (UV-13)

-continued

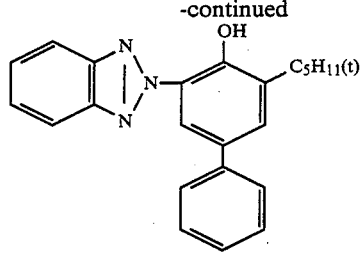 (UV-14)

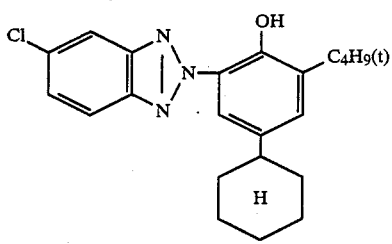 (UV-15)

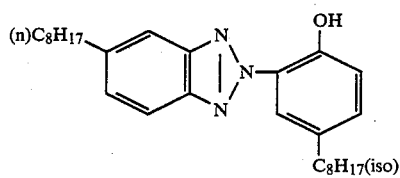 (UV-16)

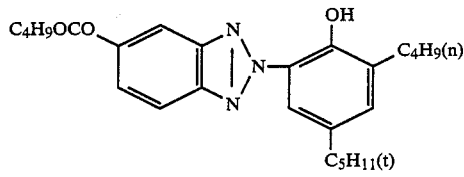 (UV-17)

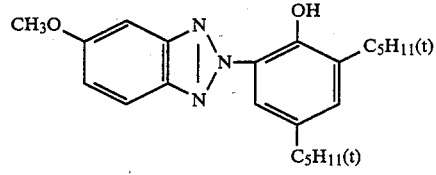 (UV-18)

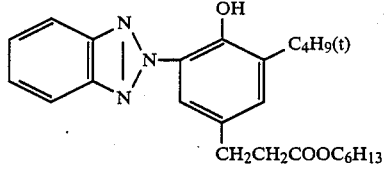 (UV-19)

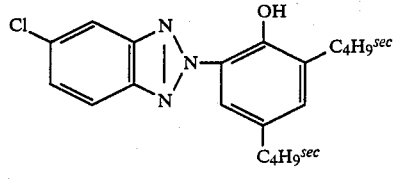 (UV-20)

Methods for synthesizing the compound represented by the general formula (XI) described above or examples of other compounds are dscribed in Japanese Patent Publication No. 29620/69, Japanese patent application (OPI) Nos. 151149/75 and 95233/79, U.S. Pat. No. 3,766,205, European Pat. No. 0057160, *Research Disclosure*, No. 22519 (1983), etc. In addition, high molecular weight ultraviolet light absorbing agents as described in Japanese patent application (OPI) Nos. 111942/83, and 178351/83 (British Pat. No. 2,118,315A), U.S. Pat. No. 4,455,368, Japanese patent application (OPI) Nos. 19945/84 and 23344/84 (British Pat. No. 2,127,569A) can be employed. A specific example thereof has been shown as UV-6. The low molecular weight ultraviolet light absorbing agent and the high molecular weight ultraviolet light absorbing agent may be used in combination.

The above-described ultraviolet light absorbing agent is emulsified and dispersed in a hydrophilic colloid in the same manner as described for the coupler above.

It is not always necessary to use the above-described high-boiling organic solvent, however, the use of such the light-boiling organic solvent is favorable.

The amounts of the high-boiling organic solvent and the ultraviolet light absorbing agent are not particularly limited, but the high-boiling organic solvent is usually used in an amount of less than 300% based on the weight of the ultraviolet light absorbing agent. Compounds which are liquid at an ordinary temperature are preferably used alone or in combination.

Combined use of the ultraviolet light absorbing agent represented by the above described general formula (XI) with the coupler of the present invention serves to improve preservability, particularly light fastness, of formed dye images, especially cyan images. The ultraviolet light absorbing agent may be co-emulsified with the cyan coupler.

As to the amount of the ultraviolet light absorbing agent, it suffices to add it in an enough amount to impart to the cyan dye image stability against light but, when used in a too excess amount, it sometimes causes yellowing of unexposed portions (white background) of the color photographic material. Therefore, the amount is usually selected between $1 \times 10^{-4}$ mole/m$^2$ and $2 \times 10^{-3}$ mole/m$^2$, particularly $5 \times 10^{-4}$ mole/m$^2$ to $1.5 \times 10^{-3}$ mole/m$^2$.

Suitable examples of color mixing preventing agents used in the present invention include hydroquinones and other various reducing agents. Most representative compounds are alkyl hydroquinones, and these are usually employed in an intermediate layer. Suitable examples of monoalkyl-substituted hydroquinones are described, for example, in U.S. Pat. Nos. 2,360,290, 2,419,613, 2,403,721, 3,960,570 and 3,700,453, Japanese patent application (OPI) Nos. 106329/74 and 156438/75, etc., and those of dialkylsubstituted hydroquinones are described, for example, in U.S. Pat. Nos. 2,728,659, 2,732,300, 3,243,294 and 3,700,453, Japanese patent application (OPI) Nos. 156438/75, 9528/78, 55121/78, 29637/79 and 55339/85, etc.

Alkyl hydroquinones preferably used as color mixing preventing agents in the present invention are those represented by the following general formula (XII):

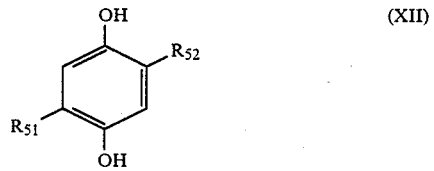 (XII)

wherein $R_{51}$ and $R_{52}$, which may be the same or different, each represents a hydrogen atom or a substituted or unsubstituted alkyl group, preferably containing from 1 to 20 carbon atoms (for example, a methyl group, a tert-butyl group, an N-octyl group, a sec-octyl group, a tert-octyl group, a sec-dodecyl group, a tert-pentadecyl group, a sec-octadecyl group, etc.), and at least one of $R_{51}$ and $R_{52}$ is an alkyl group.

Hydroquinone sulfonates are also preferably employed as color mixing preventing agents as described in U.S. Pat. No. 2,701,197, Japanese patent application (OPI) No. 172040/85, etc. Hydroquinone sulfonates preferably used as color mixing preventing agents in the present invention are those represented by the following general invention are those represented by the following general formula (XIII):

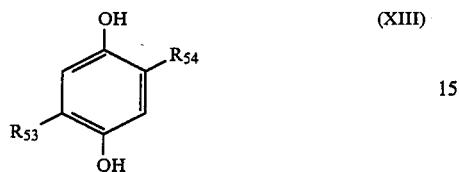
(XIII)

wherein $R_{53}$ represents a substituted or unsubstituted alkyl group, alkylthio group, amido group or alkoxy group; and $R_{54}$ represents a sulfo group or a sulfoalkyl group (for example, a sulfopropyl group).

Further, amidohydroquinones are preferably employed as color mixing preventing agents as described in Japanese patent application (OPI) No. 202465/84, Japanese patent application Nos. 165511/85 and 296088/85, etc. Amidohydroquinones preferably used as color mixing preventing agents in the present invention are those represented by the following general formula (XIV):

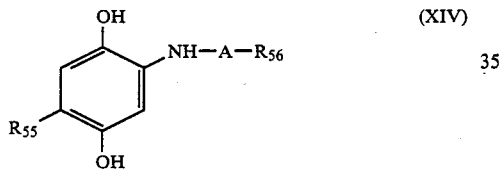
(XIV)

wherein $R_{55}$ represents a hydrogen atom, a halogen atom, a substituted or unsubstituted alkyl group; A represents

or $-SO_2-$; and $R_{56}$ represents a substituted or unsubstituted alkyl group or aryl group.

In addition to the above described alkyl hydroquinones, hydroquinone sulfonates and amidohydroquinones, hydroquinones having an electron withdrawing substituent as described, for example, in Japanese patent application (OPI) Nos. 43521/80, 109344/81 and 22237/82, etc. are preferably employed as color mixing preventing agents.

Specific examples of hydroquinones preferably employed as color mixing preventing agents are set forth below.

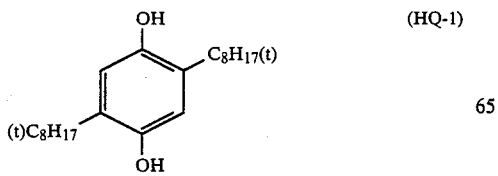
(HQ-1)

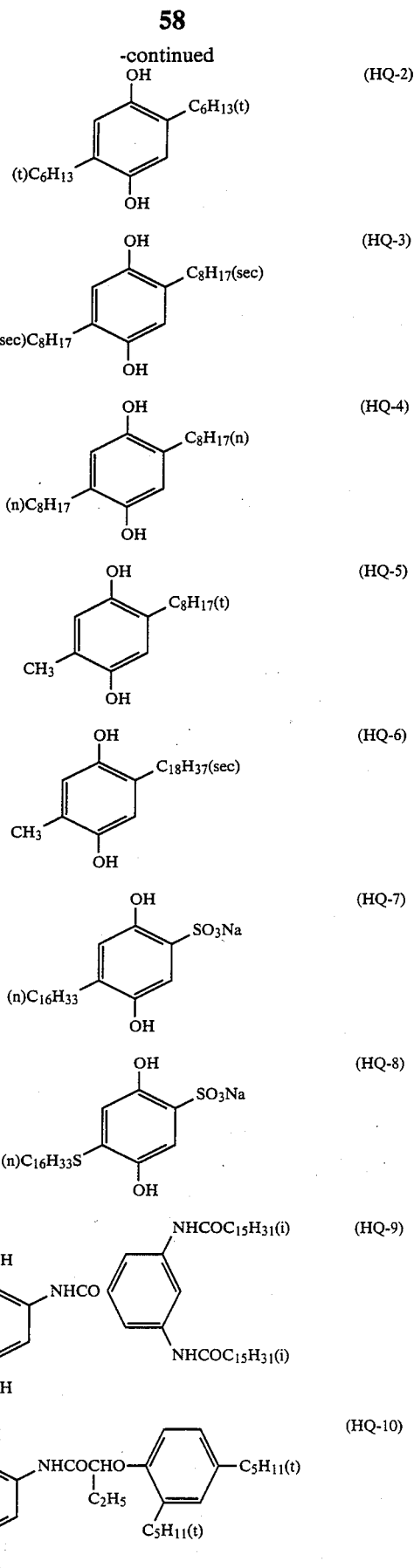

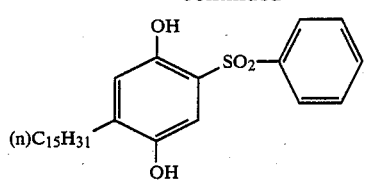
(HQ-11)

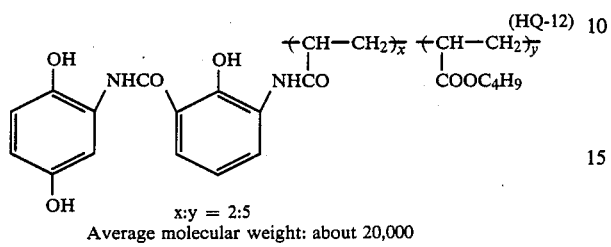
(HQ-12)

x:y = 2:5
Average molecular weight: about 20,000

Reducing agents having a skeleton other than a hydroquinone may also be employed as color mixing preventing agents. Suitable examples thereof include gallic acid amides as described in Japanese patent application (OPI) No. 156933/83, sulfonamido phenols as described in Japanese patent application (OPI) Nos. 5247/84 and 202465/84, etc.

Specific examples of such reducing agents are set forth below.

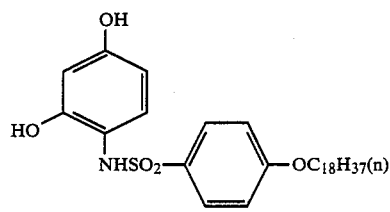
(RD-1)

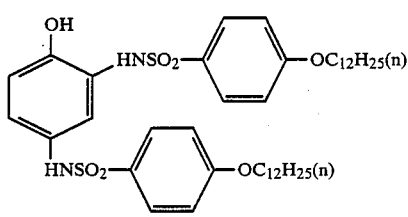
(RD-2)

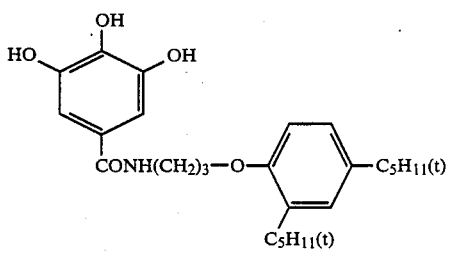
(RD-3)

Various silver halides may be used in the silver halide emulsion layer of the color photographic light-sensitive material according to the present invention. For example, there are illustrated silver chloride, silver bromide, silver chlorobromide, silver iodobromide, silver chloroiodobromide, etc. Silver iodobromide containing from 2 to 20 mole % silver iodide and silver chlorobromide containing from 10 to 50 mole % silver bromide are preferable. In photographic light-sensitive materials such as color paper, which are required to conduct a rapid processing, silver chlorobromide containing not more than 10 mole %, particularly not more than 5 mole % silver bromide is preferably used. Silver halide grains are not particularly limited as to crystal form, crystal structure, grain size, grain size distribution, etc., but crystals of silver halide used in color paper are preferably those having a regular crystal structure, particularly a cubic or tetradecahedral structure. With respect to grain size distribution, it is also preferred to use a mono-dispersed emulsion having a coefficient of variation of not more than 0.15, particularly not more than 0.10. Further, tabular grains having a thickness of 0.5 μ or less, a diameter of at least 0.6 μ, and an average aspect ratio of 5 or more, as described in Research Disclosure, No. 22534, may be used.

Crystal structure may be uniform or of a structure wherein the inner portion and the outer portion are different from each other in composition, or may be stratiform. Further, silver halide crystals different from each other in composition may be conjuncted by epitaxial conjunction or silver halide crystals may comprise a mixture of grains of various crystal forms. In addition, silver halide grains of the type forming a latent image mainly on the surface thereof and grains of the type forming a latent image mainly in the interior thereof may be used.

As to grain size of silver halide grains, fine grains having a grain size of not more than 0.1 μ and large-sized grains having a grain size of up to 3 μ in projected area diameter may be used. In a case of color paper, a grain size from 0.2 μ to 1.2 μ is preferred.

The above described silver halide emulsion may be sensitized by ordinarily employed chemical sensitization process, i.e., a sulfur sensitization process, a noble metal sensitization process, or a combination thereof. Further, the silver halide emulsion of the present invention may be provided with color sensitivity in desired light-sensitive wavelength region by using sensitizing dyes. Dyes to be advantageously used in the present invention include cyanine dyes, merocyanine dyes and complex merocyanine dyes, etc.

As supports to be used in the present invention, any of transparent supports such as polyethylene terephthalate and cellulose triacetate and reflective supports as described hereinafter may be used, with the latter reflective supports being preferable. As the reflective supports, there are illustrated, for example, baryta paper, polyethylene-coated paper, polypropylene synthetic paper, a vinyl chloride resin having coated thereon or containing therein a reflective substance such as $TiO_2$, etc., transparent supports having provided thereon a reflective layer or having a reflective substance, such as glass sheet, polyester films (e.g., polyethylene terephthalate, cellulose triacetate, or cellulose nitrate), polyamide films, polycarbonate films, polystyrene films, etc. These supports may appropriately be selected depending upon the purpose for use.

In the photographic light-sensitive material of the present invention, the photographic emulsion layers and other hydrophilic colloid layers may contain whitening agents such as stilbene type, diazine type, triazine type, oxazole type, or coumarine type whitening agents. They may be water-soluble, and water-insoluble whitening agents may be used in the form of a dispersion. Specific examples of suitable fluorescent whitening agents are described in U.S. Pat. Nos. 2,632,701, 3,269,840, and 3,359,102, British Pat. Nos. 852,075 and 1,319,763 and Research Disclosure, Vol. 176, No. 17643, page, 24, left column, line 9 to 36, "Brighteners" (Dec., 1978), etc.

Further, to silver halide emulsion layers or other hydrophilic colloid layers, substantially light-insensitive fine grain silver halide emulsion (for example, a silver chloride, silver bromide, or silver chlorobromide emulsion having an average particle size of 0.20 μ or less) may be added, if desired.

A color developing solution used in the present invention is preferably an alkaline aqueous solution containing an aromatic primary amine color developing agent as the main component. Typical examples of the color developing agents include 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4amino-N-ethyl-N-β-methanesulfonamidoethylaniline, 4-amino-3-methyl-N-ethyl-N-β-methoxyethylaniline, etc.

The color developing solution can further contain pH buffering agents such as sulfites, carbonates, borates, or phosphates of alkali metals, etc., development inhibitors or antifogging agents such as bromides, iodides, or organic antifogging agents, etc. In addition, if desired, the color developing solution can also contain water softeners; preservatives such as hydroxylamine, etc.; organic solvents such as benzyl alcohol, diethylene glycol, etc.; development accelerators such as polyethylene glycol, quaternary ammonium salts, amines, etc.; dye forming couplers; competing couplers; fogging agents such as sodium borohydride, etc.; auxiliary developing agents such as 1-phenyl-3-pyrazolidone, etc.; viscosity-imparting agents; polycarboxylic acid type chelating agents as described in U.S. Pat. No. 4,083,723; antioxidants as described in West German patent application (OLS) No. 2,622,950; and the like.

In case of adding benzyl alcohol to the color developing solution, the amount thereof is preferably not more than 2.0 ml, more preferably not more than 0.5 ml, per liter of the solution. No addition of benzyl alcohol is most preferred. Using the cyan coupler according to the present invention, sufficiently high color density can be obtained without benzyl alcohol in the color developing solution. The color developing time is preferably from 30 seconds to 2 minutes and 30 seconds, more preferably from 45 seconds to 2 minutes.

After color development, the photographic emulsion layer is usually subjected to a bleaching processing. The bleach processing may be performed simultaneously with a fixing processing, or they may be performed independently. For the purpose of a rapid processing, a bleach-fixing processing is preferred.

Bleaching agents which can be used include compounds of polyvalent metals, for example, iron (III), cobalt (III), chromium (VI), and copper (II), peracids, quinones and nitroso compounds. For example, ferricyanides; dichromates; organic complex salts of iron (III) or cobalt (III), for example, complex salts of aminopolycarboxylic acids (e.g., ethylenediaminetetraacetic acid, nitrilotriacetic acid, 1,3-diamino-2-propanoltetraacetic acid, etc.) or organic acids (e.g., citric acid, tartaric acid, malic acid, etc.); persulfates; permanganates; nitrosophenol; etc. can be used. Of these compounds, potassium ferricyanide, iron (III) sodim ethylenediaminetetraacetate, and iron (III) ammonium ethylenediaminetetraacetate are particularly useful. Ethylenediaminetetraacetic acid iron (III) complex salts are useful in both an independent bleaching solution and a mono-bath bleach-fixing solution.

After color development or bleach-fixing processing step, washing with water may or may not be conducted. In place of washing with water after the bleach-fixing processing, a so-called stabilizing processing can be performed.

Color development can be practiced at an appropriate temperature ranging from 18° to 55° C. Color development is conducted preferably at 30° C. or higher and particularly at 35° C. or higher. For continuous development processing, it is preferred to practice replenishing of processing solutions. Replenisher of about 330 ml or less per $m^2$ and, if desired, 100 ml or less per $m^2$ of the photographic materials to be processed may be preferably employed.

Bleach-fixing can be practiced at an appropriate temperature ranging from 18° to 50° C., and preferably at 30° C. or higher. When the bleach-fixing is conducted at 35° C. or higher, it is possible to shorten the processing time to a range of 1 minute or less and to reduce an amount of replenisher to be added. The time necessary for washing with water after color development or bleach-fixing is usually within 3 minutes.

Dyes formed are degraded not only with light, heat or temperature but also by mold during preservation. Since cyan color images are particularly degraded by mold, it is preferred to employ antimolds. Specific examples of antimolds include 2-thiazolylbenzimidazoles as described in Japanese patent application (OPI) No. 157244/82. Antimolds can be incorporated into the photographic light-sensitive material or may be added thereto from outside during development processing.

Now, a color developing solution according to the present invention is described in detail below.

The color developing solution used in the present invention contains a known aromatic primary amine color developing agent. Preferred examples thereof are p-phenylenediamine derivatives. Typical examples of the p-phenylenediamine derivative used are set forth below, but the present invention should not be construed as being limited thereto.

D-1: N,N-Diethyl-p-phenylenediamine
D-2: 2-Amino-5-diethylaminotoluene
D-3: 2-Amino-5-(N-ethyl-N-laurylamino)toluene
D-4: 4-[N-Ethyl-N-(β-hydroxyethyl)amino]aniline
D-5: 2-Methyl-4-[N-ethyl-N-(β-hydroxyethyl)amino]aniline
D-6: 4-Amino-3-methyl-N-ethyl-N-[β-(methanesulfonamido)ethyl]aniline
D-7: N-(2-Amino-5-diethylaminophenylethyl)methanesulfonamide
D-8: N,N-Dimethyl-p-phenylenediamine
D-9: 4-Amino-3-methyl-N-ethyl-N-methoxyethylaniline
D-10: 4-Amino-3-methyl-N-ethyl-N-β-ethoxyethylaniline
D-11: 4-Amino-3-methyl-N-ethyl-N-β-butoxyethylaniline Of these p-phenylenediamine derivatives, 4-amino-3-methyl-N-ehtyl-N-[β-(methanesulfonamido)ethyl]aniline is particularly preferred.

These p-phenylenediamine derivatives may be in the form of salts such as sulfates, hydrochlorides, sulfites, or p-toluenesulfonates.

The aromatic primary amine developing agent is used in an amount of from about 0.1 g to about 20 g and preferably from about 0.5 g to about 10 g per liter of the developing solution.

Also, the color developing solution used in the present invention may contain, if desired, sulfites such as sodium sulfite, potassium sulfite, sodium bisulfite, potassium bisulfite, sodium metasulfite, and potassium metasulfite, or carbonyl-sulfite adducts, as preservatives.

Further, it is preferred to add, as compounds capable of directly preservating the color developing agent, various hydroxylamines, hydroxamic acids as described in Japanese patent application No. 186559/86, hydrazines and hydrazides as described in Japanese patent application No. 170756/86, phenols as described in Japanese patent application Nos. 188742/86 and 203253/86, α-hydroxyketones and α-aminoketones as described in Japanese patent application No. 188741/86 and/or various saccharides as described in Japanese patent application No. 180616/86 to the color developing solution. Moreover, together with the above described compounds, monoamines as described in Japanese patent application Nos. 147823/86, 166674/86, 165621/86, 164515/86, 170789/86 and 168159/86, etc., diamines as described in Japanese patent application Nos. 173595/86, 164515,86 and 186560/86, etc., polyamines as described in Japanese patent application Nos. 165621/86 and 169789/86, polyamines as described in Japanese patent application No. 188619/86, nitroxy radicals as described in Japanese patent application No. 197760/86, alcohols as described in Japanese patent application Nos. 186561/86 and 197419/86, oximes as described in Japanese patent application No. 198987/86, and tertiary amines as described in Japanese patent application No. 265149/86 are preferably employed.

Other preservatives such as various metals as described in Japanese patent application (OPI) Nos. 44148/82 and 53749/82, salicylic acids as described in Japanese patent application (OPI) No. 180588/84, alkanolamines as described in Japanese patent application (OPI) No. 3532/79, polyethyleneimines as described in Japanese patent application (OPI) No. 94349/81, aromatic polyhydroxy compounds as described in U.S. Pat. No. 3,746,544, etc. may be incorporated into the color developing solution, if desired. Particularly, the addition of aromatic polyhydroxy compounds is preferred.

The color developing solution used in the present invention has a pH which ranges preferably from 9 to 12 and more preferably from 9 to 11.0. The color developing solution may also contain any of the compounds that are known to be usable as components of developing solutions.

In order to maintain the pH in the above-described range, various kinds of buffers are preferably employed. Specific examples of these buffers include sodium carbonate, potassium carbonate, sodium bicarbonate, potassium bicarbonate, trisodium phosphate, tripotassium phosphate, disodium phosphate, dipotassium phosphate, sodium borate, potassium borate, sodium tetraborate (borax), potassium tetraborate, sodium o-hydroxybenzoate (sodium salicylate), potassium o-hydroxybenzoate, sodium 5-sulfo-2-hydroxybenzoate (sodium 5-sulfosalicylate), and potassium 5-sulfo-2-hydroxybenzoate (potassium 5-sulfosalicylate). The present invention should not be construed as being limited to these comounds.

The amount of the buffer to be added to the color developing solution is preferably 0.1 mol or more and more preferably from 0.1 mol to 0.4 mol per liter thereof.

In addition, various chelating agents can be used in the color developing solution according to the present invention for the purpose of preventing calcium or magnesium precipitation or increasing the stability of the color developing solution.

Specific examples of the chelating agents used are set forth below, but the present invention should not be construed as being limited thereto.
Nitrilotriacetic acid
Diethyleneaminopentaacetic acid
Ethylenediaminetetraacetic acid
N,N,N-Trimethylenephosphonic acid
Ethylenediamine-N,N,N',N'-tetramethylenephosphonic acid
Trans-cyclohexanediaminetetraacetic acid
1,2-Diaminopropanetetraacetic acid
Glycol ether diaminetetraacetic acid
Ethylenediamine-o-hydroxyphenylacetic acid
2-Phosphnobutane-1,2,4-tricarboxylic acid
1-Hydroxyethane-1,1-diphosphonic acid
N,N'-Bis(2-hydroxybenzyl)ethylenediamine-N,N'-diacetic acid Two or more kinds of such chelating agents may be employed together, if desired.

The chelating agent is added to the color developing solution in an amount sufficient to block metal ions present therein. For example, a range of from about 0.1 g to about 10 g per liter of the color developing solution is employed.

The color developing solution may contain appropriate development accelerators, if desired.

The above-described compounds used in the present invention exhibit remarkable effects particularly in the case of using a color developing solution which does not substantially contain benzyl alcohol.

Examples of suitable development accelerators include thioether type compounds as described in Japanese Patent Publication Nos. 16088/62, 5987/62, 7826/63, 12380/69, and 9019/70 and U.S. Pat. No. 3,813,247; p-phenylenediamine type compounds as described in Japanese patent application (OPI) Nos. 49829/77 and 15554/75; quaternary ammonium salts as described in Japanese patent application (OPI) Nos. 137726/75, 156826/81, and 43429/77 and Japanese Patent Publication No. 30074/69; p-aminophenols as described in U.S. Pat. Nos. 2,610,122 and 4,119,462; amine type compounds as described in U.S. Pat. Nos. 2,494,903, 3,128,182, 4,230,796, 3,253,919, 2,482,546, 2,596,926, and 3,582,346 and Japanese Patent Publication No. 11431/66; polyalkylene oxides as described in Japanese Patent Publication Nos. 16088/62, 25201/67, 11431/66, and 23883/67 and U.S. Pat. Nos. 3,138,183 and 3,532,501; 1-phenyl-3-pyrazolidones; and imidazoles.

The color developing solution used in the present invention may contain appropriate antifoggants, if desired. Alkali metal halides such as sodium chloride, potassium bromide, and potassium iodide as well as organic antifoggants may be employed as antifoggants. Representative examples of organic antifoggants include nitrogen-containing heterocyclic compounds such as benzotriazole, 6-nitrobenzimidazole, 5-nitroisoindazole, 5-methylbenzotriazole, 5-nitrobenzotriazole, 5-chlorobenzotriazole, 2-thiazolylbenzimidazole, 2-thiazolylmethylbenzimidazole, indazole, hydroxyazaindolizine and adenine, etc.

It is preferred that the color developing solution according to the present invention contains fluorescent brightening agents. As fluorescent brightening agents, 4,4'-diamino-2,2'-disulfostilbene type compounds are preferred. The amount of the fluorescent brightening agent added is less than 5 g and preferably from 0.1 g to 4 g per liter of the color developing solution.

Furthermore, the color developing solution according to the present invention may contain various surface active agents such as alkylphosphonic acids, arylphosphonic acids, aliphatic carboxylic acids, and aromatic carboxylic acids, etc., if desired.

The processing temperature of the color development step used in the present invention is usually from 20° C. to 50° C. and preferably from 30° C. to 40° C. The processing time is usually from 20 sec. to 5 min. and preferably from 30 sec. to 2 min. Further, the amount of a replenisher for the color developing solution is usually from 20 ml to 600 ml, preferably from 50 ml to 300 ml, and more preferably from 100 ml to 200 ml per square meter of the color photographic light-sensitive material.

A silver removing step used in the present invention is described in detail below.

In the silver removing step according to the present invention, a bleach-fixing solution is employed. According to the present invention, the effects of the present invention become more remarkable when the processing time of silver removing step is shortened. More specifically, the processing time is preferably up to 6 min., more preferably from 30 sec. to 4 min., and furthermore preferably from 30 sec. to 60 sec.

Now, a bleach-fixing solution which can be employed in the present invention is described below.

Bleaching agents used in the bleach-fixing solution according to the present invention include organic complex salts of iron, cobalt, nickel, manganese and chromium, etc. Particularly, organic complex salts of iron (III), for example, complex salts of aminopolycarboxylic acids (e.g., ethylenediaminetetraacetic acid, diethylenetriaminepentaacetic acid, etc.), aminopolyphosphonic acids, phosphonocarboxylic acids and organic phosphonic acids, etc. or complex salts of organic acids (e.g., citric acid, tartaric acid, malic acid, etc.) are preferably used. Of these compounds, aminopolycarboxylic acid complex salts of iron (III) are particularly preferred in view of a rapid processing and prevention from environmental pollution.

Specific examples of useful aminopolycarboxylic acids suitable for forming organic complex salts of iron (III) are set forth below.
Ethylenediaminetetraacetic acid
Diethylenetriaminepentaacetic acid
1,3-Diaminopropanetetraacetic acid
Propylenediaminetetraacetic acid
Nitrilotriacetic acid
Cyclohexanediaminetetraacetic acid
Methyliminodiacetic acid
Iminodiacetic acid
Glycol ether diaminetetraacetic acid These compounds may be in the form of salt such as sodium, potassium, lithium or ammonium.

Of these compounds, iron (III) complex salt of ethylenediaminetetraacetic acid, diethylenetriaminepentaacetic acid, cyclohexanediaminetetraacetic acid, 1,3-diaminopropanetetraacetic acid or methyliminodiacetic acid are preferred because of their high bleaching ability.

The ferric ion complex salts may be used in the form of a complex salt per se or may be formed in situ in solution by using a ferric salt (e.g., ferric sulfate, ferric chloride, ferric nitrate, ferric ammonium sulfate or ferric phosphate, etc.) and a chelating agent (e.g., an aminopolycarboxylic acid, etc.). Further, a chelating agent may be used in an excess amount of being necessary for forming a ferric ion complex salt.

The amount of ferric iron complex in the bleach-fixing solution is from 0.01 mol to 1.0 mol, preferably from 0.05 mol to 0.50 mol per liter of the solution.

In the bleach-fixing solution, or a prebath thereof as bleach accelerating agents, various kinds of compounds can be used. Specific examples of suitable bleach accelerating agents include compounds having a mercapto group or a disulfide bond as described in U.S. Pat. No. 3,893,858, West German Pat. No. 1,290,812, Japanese patent application (OPI) No. 95630/78, Research Disclosure, No. 17129 (Jul. 1978), etc.; thiourea derivatives as described in Japanese Patent Publication No. 8506/70, Japanese patent application (OPI) Nos. 20832/77 and 32735/78, U.S. Pat. No. 3,706,561, etc.; and halides such as iodine ions, bromine ions, etc. These compounds are preferred in view of their large bleaching ability.

The bleach-fixing solution used in the present invention can contain rehalogenating agents such as bromides (e.g., potassium bromide, sodium bromide, ammonium bromide, etc.), chlorides (e.g., potassium chloride, sodium chloride, ammonium chloride, etc.) or iodides (e.g., ammonium iodide, etc.). Further, one or more kinds of inorganic acids, organic acids, alkali metal salts thereof or ammonium salts thereof which have a pH buffering ability (e.g., boric acid, borax, sodium metaborate, acetic acid, sodium acetate, sodium carbonate, potassium carbonate, phosphorous acid, phosphoric acid, sodium phosphate, citric acid, sodium citrate, tartaric acid, etc.), corrosion preventing agents (e.g., ammonium nitrate, guanidine, etc.), or the like may be added, if desired.

As fixing agents which can be employed in the bleach-fixing solution according to the present invention, known fixing agents such as thiosulfates (e.g., sodium thiosulfate, ammonium thiosulfate, etc.) are preferably employed. In addition, a special bleach-fixing solution comprising a combination of fixing agent and a large amount of a halide compound such as potassium iodide as described in Japanese patent application (OPI) No. 155354/80 can be used as well.

The amount of fixing agent to be used in the bleach-fixing solution is preferably from 0.3 mol to 2 mol, and more preferably from 0.5 mol to 1.0 mol per liter of the solution.

The pH of the bleach-fixing solution used in the present invention is preferably from 3.5 to 6.5, and more preferably from 4 to 5.5. In order to adjust pH, various organic or inorganic acids, organic or inorganic bases or buffering agents may be employed. Specific examples of acids include hydrochloric acid, sulfuric acid, nitric acid, phosphoric acid, acetic acid, propionic acid, citric acid, etc. Specific examples of bases include sodium hydroxide, potassium hydroxide, aqueous ammonia, various amines, etc, but are not to be limited thereto. When the pH of the bleach-fixing solution is higher than the above-described value, desilvering property and image stability become poor. On the contrary, when the pH is lower than the above described value, degradation of the solution and the formation of leuco dyes of cyan dyes tend to be accelerated.

Further, various kinds of fluorescent brightening agent, defoaming agents and surface active agents, polyvinyl pyrrolidone, organic solvents (e.g., methanol, etc.), etc. may be incorporated into the bleach-fixing solution.

The bleach-fixing solution or fixing solution used in the present invention can contain, as preservatives, compounds capable of releasing sulfite ions such as sulfites (e.g., sodium sulfite, potassium sulfite, ammonium sulfite, etc,), bisulfites (e.g., ammonium bisulfite, sodium bisulfite, potassium bisulfite, etc.), metabisulfites (e.g., potassium metabisulfite, sodium metabisulfite, ammonium metabisulfite, etc.), etc. The amount of such a compound to be added is preferably from about 0.02 mol to about 0.50 mol, and more preferably from 0.04 mol to 0.40 mol per liter of the solution calculated in terms of a sulfite ion.

While it is general to add sulfites as preservatives, other compounds such as ascorbic acid, a carbonylbisulfic acid adduct, a carbonyl compound, etc. may be added.

Further, buffers fluorescent brightening agent, chelating agents, deforming agents, antimolds, etc. may be added, if desired.

After a silver removing processing such as fixing or bleach-fixing, etc., the silver halide color photographic material according to the present invention is generally subjected to a water washing step and/or a stabilizing step.

An amount of water required for the water washing step may be set in a wide range depending on characteristics of photographic light-sensitive materials (due to elements used therein, for example, couplers, etc.), uses thereof, temperature of washing water, a number of water washing tanks (stages), a replenishment system such as countercurrent or orderly current, etc., or other various conditions. A relationship between a number of water washing tanks and an amount of water in a multistage countercurrent system can be determined bases on the method as described in *Journal of the Society of Motion Picture and Television Engineers*, Vol. 64, pages 248 to 253 (May, 1955). Ordinarily, a number of stages used in the multi-stage countercurrent system is preferably from 2 to 6, particularly from 2 to 4.

According to the multi-stage countercurrent system, the amount of water for washing can be significantly reduced. For example, it is possible to use 0.5 to 1 liter of less per m$^2$ of the photographic light-sensitive material. However, increase in staying time of water in a tank causes propagation of bacteria and some problems such as adhesion of floatage formed on the photographic materials, etc. occur. In the processing of the silver halide color photographic material according to the present invention, a method for reducing amounts of calcium and magnesium as described in Japanese patent application (OPI) No. 288838/87 can be particularly effectively employed in order to solve such problems. Further, sterilizers, for example, isothiazolone compounds and cyabendazoles as described in Japanese patent application (OPI) No. 8542/82, chlorine type sterilizers such as sodium chloroisocyanurate as described in Japanese patent application (OPI) No. 120145/86, etc., benzotriazoles as described in Japanese patent application (OPI) No. 267761/86, sterilizers as described in Hiroshi Horiguchi, *Bokin-Bobai No Kagaku, Biseibutsu No Mekkin-, Sakiin-, Bobai-Gijutsu*, edited by Eiseigijutsu Kai, *Bokin-Bobaizai Jiten*, edited by Nippon Bokin-Bobai Gakkai, etc. can be employed.

Moreover, surface active agents as agents for uniform drying, and chelating agents represented by EDTA as water softeners may be employed in washing water.

The pH of washing water used in the processing of the photographic light-sensitive material according to the present invention is usually from 4 to 9 and preferably from 5 to 8. The temperature of washing water and the time for the water washing step can be set in a wide range depending on characteristics of photographic light-sensitive materials, uses thereof, etc. It is selected usually in a range of 15° C. to 45° C. for 20 sec. to 10 min., preferably in a range of 25° C. to 40° C. for 30 sec. to 5 min.

Following the above described water washing step or without conducting the water washing step, the color photographic material can be directly treated with a stabilizing solution. To the stabilizing solution are added compounds having a function of stabilizing images, for example, aldehyde compounds represented by formalin, buffers for adjusting pH of layer to a value suitable for stabilization of dyes formed, or ammonium compounds, etc. Further, various sterilizers or antimolds as described above can be employed in the stabilizing solution in order to prevent the propagation of bacteria in the solution and impart antimold property to the photographic material after processing. Moreover, surface active agents, fluorescent whitening agents, hardeners, etc. may be added to the stabilizing solution.

The photographic light-sensitive material of the present invention can also be directly subjected to stabilizing processing without conducting the water washing step. In such a case, any of known methods as described in Japanese patent application (OPI) Nos. 8543/82, 14834/83, 184343/84, 220345/85, 238832/85, 239784/85, 239749/85, 4054/86 and 118749/86, etc.

Further, a chelating agent such as 1-hydroxyethylidene-1,1-diphosphonic acid, ethylenediaminetetramethylenephosphonic acid, etc., a magnesium compound, or a bismuth compound may be preferably employed.

The solutions used in the water washing step and/or stabilizing step can be utilized in preceding steps. For instance, overflow from the washing water in a multistage countercurrent system is introduced into a bleach-fixing bath which is a preceding bath and a concentrated solution is supplied to the bleach-fixing solution whereby an amount of discharge is reduced.

The method according to the present invention can be applied to any processing as far as a color developing solution is employed therein. For example, it can be utilized in processing of color paper, color reversal paper, direct positive color light-sensitive materials, color positive films, color negative films, color reversal films, etc. Particularly, it is preferably applied for color paper and color reversal paper.

In a silver halide emulsion of the photographic light-sensitive material according to the present invention, silver halide having any halogen composition such as silver iodobromide, silver bromide, silver chlorobromide, silver chloride, etc. can be employed. However, in the case of conducting a rapid processing or a processing with a low level of replenishment, a silver chlorobromide emulsion containing not less than 60 mol% of silver chloride and a silver chloride emulsion are preferred, and a silver halide emulsion having a silver chloride content of from 80 to 100 mol% is particularly preferred.

On the other hand, in the case wherein high sensitivity is required and it is necessary to control fog formation during the preparation, preservation and/or processing of the photographic light-sensitive material at a particularly low level, a silver chlorobromide emulsion containing not less than 50 mol% of silver bromide and a silver bromide emulsion each of which may contain up to 3 mol% of silver iodide are preferred, and a silver halide emulsion having a silver bromide content of not less than 70 mol% is more preferred. In the case of color photographic materials for photographing, silver iodobromide and silver chloroiodobromide are preferred. The silver iodide content therein is preferably from 3 to 15 mol%.

Silver halide grains in the silver halide emulsion which can be used in the present invention may have different layers in the inner portion and the surface portion, multi-phase structures containing junctions or may be uniform throughout the grains. However, silver halide grains having any structure are more preferred than those having a uniform phase. Particularly, those having a double structure are preferred. Further, a mixture of those silver halide grains having different structures may be employed.

Grain size distribution of silver halide grains used in the present invention may be either narrow or broad. It is preferred to employ a so-called mono-dispersed silver halide emulsion in which a coefficient of variation which is obtained by dividing a standard deviation derived from a grain size distribution curve of a silver halide emulsion by an average grain size is 20% or less and particularly 15% or less in the present invention.

Further, in order to achieve the desired gradation of the photographic light-sensitive material, two or more mono-dispersed silver halide emulsions which have substantially same spectral sensitivity but have different grain sizes from each other can be mixed in one emulsion layer or can be coated in the form of superimposed layers (regarding mono-dispersity, those having the coefficient of variation described above is preferred). Moreover, two or more poly-dispersed silver halide emulsions or combinations of a mono-dispersed emulsion and a poly-dispersed emulsion may be employed in a mixture or in the form of superimposed layers.

Silver halide grains which can be used in the present invention may have a regular crystal structure, for example, a cubic, octahedral, rhombic dodecahedral or tetradecahedral structure, etc., or a mixture thereof, an irregular crystal structure, for example, a spherical structure, etc., or a composite structure thereof.

Silver halide grains having a cubic or tetradecahedral structure are particularly preferred.

Further, tabular silver halide grains can be used. Particularly, a silver halide emulsion wherein tabular silver halide grains having a ratio of diameter/thickness of from 5 to 8, or of preferably not less than 8 are account for at least 50% of the total projected area of the silver halide grains present can be employed. In addition, mixtures of silver halide grains having different crystal structures may be used.

These silver halide emulsions may be those of surface latent image type in which latent images are formed mainly on the surface thereof, those of internal latent image type in which latent images are formed mainly in the interior thereof.

The photographic emulsions used in the present invention can be prepared according to the methods as described in Research Disclosure, Vol. 176, No. 17643, Items I, II and III (Dec., 1978).

The photographic emulsions used in the present invention are usually conducted with physical ripening, chemical ripening and spectral sensitization. Various kinds of additives which can be used in these steps are described in Research Disclosure, Vol. 176, No. 17643 (Dec., 1978) and ibid., Vol. 187, No. 18716 (Nov., 1979), and concerned items thereof are summarized in the table shown below.

Further, known photographic additives which can be used in the present invention are also described in the above mentioned Research Disclosures and concerned item thereof are summarized in the table below.

| Kind of Additives | RD 17643 | RD 18716 |
|---|---|---|
| 1. Chemical Sensitizers | Page 23 | Page 648, right column |
| 2. Sensitivity Increasing Agents | | Page 648, right column |
| 3. Spectral Sensitizers | Pages 23 to 24 | Page 648, right column |
| 4. Super Sensitizers | | Page 649, right column |
| 5. Whitening Agents | Page 24 | |
| 6. Antifoggants and Stabilizers | Pages 24 to 25 | Page 649, right column |
| 7. Couplers | Page 25 | |
| 8. Organic Solvents | Page 25 | |
| 9. Light-Absorbers, Filter Dyes | Pages 25 to 26 | Page 649, right column to page 650, left column |
| 10. Ultraviolet Ray Absorbers | | |
| 11. Antistaining Agents | Page 25, right column | Page 650, left column to right column |
| 12. Dye Image Stabilizers | Page 25 | Page 650, left column to right column |
| 13. Hardeners | Page 26 | Page 651, left column |
| 14. Binders | Page 26 | Page 651, left column |
| 15. Plasticizers and Lubricants | Page 27 | Page 650, right column |
| 16. Coating Aids and Surfactants | Pages 26 to 27 | Page 650, right column |
| 17. Antistatic Agents | Page 27 | Page 650, right column |

The present invention will be explained in greater detail with reference to the following examples, but the present invention should not be construed as being limited thereto.

EXAMPLE 1

A mixture of 10 g of Coupler (1) according to the present invention, 10 g of dibutyl phthalate and 20 ml of ethyl acetate was heated at 50° C., and the resulting solution was emulsified and dispersed in 80 g of an aqueous solution of gelatin containing 8 ml of a 10 wt% aqueous solution of sodium dodecylbenzenesulfonate.

The emulsified dispersion was mixed with 145 g of a red-sensitive silver chlorobromide emulsion (having a bromide content of 50 mol% and containing 7 g of silver), to the mixture was added sodium dodecylbenzenesulfonate as a coating aid, and the mixture was coated on a paper support, both surfaces of which were laminated with polyethylene. The coating amount of coupler was adjusted to 400 mg/m$^2$. On the layer thus-formed, a gelatin protective layer was coated at the gelatin coating amount of 1 g/m$^2$ to prepare a sample, which was designated Sample 201.

Samples (202) to (213) were prepared in the same manner as described above except using the equimolar amount of Couplers (2), (3), (4), (5), (6), (7), (9), (10), (16), (18), (22) and (25) in place of Coupler (1) above, respectively.

For comparison Samples (214) to (219) were prepared in the same manner as discribed above except using the equimolar amount of Comparative Couplers (101), (102), (103), (104), (105) and (106) in place of Coupler (1) above, respectively.

Comparative Couplers

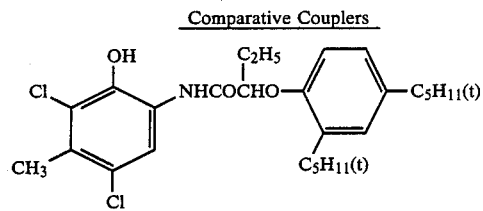
(101)

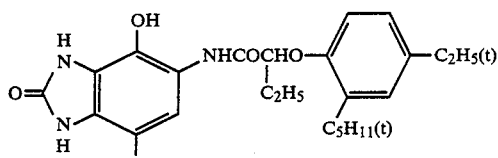
(102)

(coupler as described in U.S. Pat. No. 4,430,423)

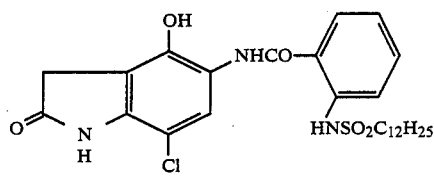
(103)

(coupler as described in U.S. Pat. No. 4,430,423)

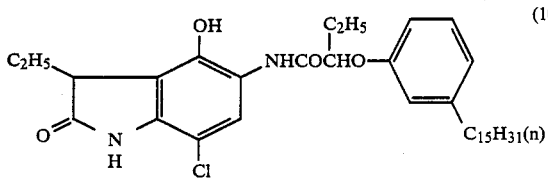
(104)

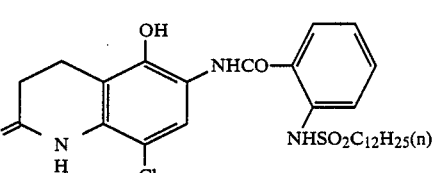
(105)

(coupler as described in U.S. Pat. No. 4,327,173)

-continued
Comparative Couplers

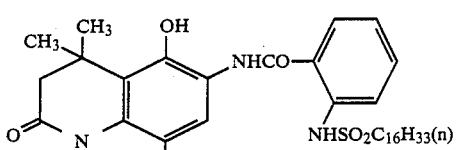
(106)

(coupler as described in U.S. Pat. No. 4,564,586)

Each sample thus-obtained was exposed to light using a continuous wedge for sensitometry and subjected to the development processing in the following manner.

| Color Development Processing (at 33° C.) | |
|---|---|
| Processing Step | Time |
| 1. Color development | 3 min 30 sec |
| 2. Bleach fixing | 1 min 30 sec |
| 3. Washing with water | 2 min 30 sec |

| Each of the processing solution used in the color development processing had the following composition. | |
|---|---|
| Color Developinq Solution | |
| Benzyl alcohol | 15.0 ml |
| Diethylene glycol | 8.0 ml |
| Ethylenediaminetetraacetic acid | 5.0 g |
| Sodium sulfite | 2.0 g |
| Anhydrous potassium carbonate | 30 g |
| Hydroxylamine sulfate | 3.0 g |
| Potassium bromide | 0.6 g |
| 4-Amino-N—ethyl-N—($\beta$-methanesulfonamido-ethyl)-m-toluidine sesquisulfate monohydrate | 5.0 g |
| Water to make | 1 l |
| | (pH 10.2) |
| Bleach-Fixing Solution | |
| Ethylenediaminetetraacetic acid | 4.0 g |
| Ferric salt of ethylenediaminetetraacetate | 40 g |
| Sodium sulfite | 5.0 g |
| Ammonium thiosulfate (70 wt %) | 150 ml |
| Water to make | 1 l |

Then, each film thus processed was subjected to examination with respect to fastness. More specifically, the samples were left for 6 days in a dark place at 100° C., the samples were left for 6 weeks in a dark place at 60° C. and 70% RH and the samples were irradiated for 6 days in a xenon test apparatus (100,000 luxes) and a density reduction rate of the sample in the area where the initial density was 1.0 was measured. Furthermore, with respect to yellow coloration of white background areas, the samples were left for 6 days in a dark at 100° C. and the samples were irradiated for 6 days in the xenon test apparatus and increase in blue density of unexposed areas was measured. The results thus-obtained are shown in Table 1 below.

TABLE 1

| | | Fastness of Color Image | | | Yellow Coloration of White Background | |
|---|---|---|---|---|---|---|
| | | 100° C. | 60° C. 70% RH | Light (Xenon) | | Light |
| Film Sample | Coupler | 6 Days (%) | 6 Weeks (%) | 6 Days (%) | 100° C. 6 Days | (Xenon) 6 Days |
| (201) | (1) (Present Invention) | 9 | 7 | 6 | +0.07 | +0.06 |
| (202) | (2) (Present Invention) | 10 | 9 | 5 | +0.06 | +0.07 |
| (203) | (3) (Present Invention) | 8 | 7 | 8 | +0.05 | +0.08 |
| (204) | (4) (Present Invention) | 8 | 7 | 7 | +0.08 | +0.05 |
| (205) | (5) (Present Invention) | 7 | 5 | 6 | +0.09 | +0.04 |
| (206) | (6) (Present Invention) | 11 | 9 | 8 | +0.07 | +0.06 |
| (207) | (7) (Present Invention) | 10 | 9 | 8 | +0.06 | +0.06 |
| (208) | (9) (Present Invention) | 10 | 8 | 6 | +0.07 | +0.09 |

TABLE 1-continued

| | | Fastness of Color Image | | | Yellow Coloration of White Background | |
|---|---|---|---|---|---|---|
| | | 100° C. 6 Days (%) | 60° C. 70% RH 6 Weeks (%) | Light (Xenon) 6 Days (%) | 100° C. 6 Days | Light (Xenon) 6 Days |
| Film Sample | Coupler | | | | | |
| (209) | (10) (Present Invention) | 9 | 7 | 4 | +0.09 | +0.08 |
| (210) | (16) (Present Invention) | 9 | 8 | 5 | +0.08 | +0.06 |
| (211) | (18) (Present Invention) | 11 | 9 | 8 | +0.10 | +0.09 |
| (212) | (22) (Present Invention) | 12 | 11 | 9 | +0.09 | +0.06 |
| (213) | (25) (Present Invention) | 12 | 10 | 7 | +0.08 | +0.06 |
| (214) | (101) (Comparison) | 55 | 54 | 20 | +0.08 | +0.07 |
| (215) | (102) (Comparison) | 13 | 6 | 5 | +0.20 | +0.25 |
| (216) | (103) (Comparison) | 15 | 10 | 6 | +0.30 | +0.24 |
| (217) | (104) (Comparison) | 8 | 12 | 4 | +0.23 | +0.20 |
| (218) | (105) (Comparison) | 8 | 8 | 18 | +0.21 | +0.25 |
| (219) | (106) (Comparison) | 7 | 5 | 8 | +0.17 | +0.29 |

It is apparent from the results shown in Table 1 that the color image formed from Coupler (101) in Comparative Sample (214) is very weak to heat and light, and although the color images formed from Couplers (102) to (106) in Comparative Samples (215) to (219) exhibit sufficient fastness, the coloration of white background areas is large.

On the contrary, it can be seen that the couplers according to the present invention not only have excellent fastness to heat and light, but also exhibit very little coloration of white background areas. The fact that the coloration of white background areas is little is a great advantage when the present invention is applied to a photographic light-sensitive material of a reflective support such as a color printing photographic materials.

EXAMPLE 2

On a paper support, both surfaces of which were laminated with polyethylene were coated the layers as shown below to prepare a multilayer photographic printing paper, which was designated Sample (A-1). The coating solutions were prepared as follows.

Preparation of the coating solution for the First Layer 10.2 g of Yellow coupler (Y-1), 9.1 g of Yellow coupler (Y-2), and 4.4 g of Dye image stabilizer (Cdp-1) were dissolved in 27.2 ml of ethyl acetate and 7.7 ml (8.0 g) of High boiling point solvent (Solv-1). This solution was emulsified and dispersed in 185 ml of a 10 wt% gelatin aqueous solution containing 8 ml of a 10 wt% aqueous solution of sodium dodecylbenzenesulfonate. Emulsions (EM1) and (EM2) described hereinafter were mixed with thus-obtained emulsified dispersion, and the gelatin concentration was adjusted whereby the composition became the following to obtain the coating solution for the First Layer.

The coating solutions for the Second to Seventh Layers were prepared in the same manner as in the above.

In all the coating solutions, 1-oxy-3,5-dichloro-s-triazine sodium salt was used as a gelatin hardener. Further, Viscosity imparting agent (Cpd-12) was used in the coating solutions.

Construction of Layers

The compositions of the layers are described below. The coated amounts are indicated in terms of g/m² provided that the coated amounts of the silver halide emulsions are indicated in terms of g silver/m².

Support:

Polyethylene laminated paper support in which the polyethylene on the First Layer side contained a white pigment (TiO₂) and a blueish dye

| First Layer: Blue-sensitive Layer | |
|---|---|
| Monodispersed silver chlorobromide emulsion (EM1) spectrally sensitized with Sensitizing dye (ExS-1) | 0.13 |
| Monodispersed silver chlorobromide emulsion (EM2) spectrally sensitized with Sensitizing dye (ExS-1) | 0.13 |
| Gelatin | 1.86 |
| Yellow coupler (Y-1) | 0.44 |
| Yellow coupler (Y-2) | 0.39 |
| Color image stabilizer (Cpd-1) | 0.19 |
| Solvent (Solv-1) | 0.35 |
| Second Layer: Color-mixing Preventing Layer | |
| Gelatin | 0.99 |
| Color mixing preventing agent (Cpd-3) | 0.08 |
| Third Layer: Green-sensitive Layer | |
| Monodispersed silver chlorobromide emulsion (EM3) spectrally sensitized with Sensitizing dyes (ExS-2, 3) | 0.05 |
| Monodispersed silver chlorobromide emulsion (EM4) spectrally sensitized with Sensitizing dyes (ExS-2, 3) | 0.11 |
| Gelatin | 1.80 |
| Magenta coupler (M-1) | 0.32 |
| Color image stabilizer (Cpd-2) | 0.24 |
| Solvent (Solv-2) | 0.12 |
| Solvent (Solv-3) | 0.25 |
| Color image stabilizer (Cod-8) | 0.03 |
| Color image stabilizer (Cod 9) | 0.02 |
| Fourth Layer: Ultraviolet Light Absorbing Layer | |
| Gelatin | 1.60 |
| Ultraviolet light absorbing agents (UV-1) | 0.62 |
| Color mixing preventing agent (Cpd-3) | 0.05 |
| Solvent (Solv-4) | 0.24 |
| Fifth Layer: Red-sensitive Layer | |
| Monodispersed silver chlorobromide emulsion (EM5) spectrally sensitized with Sensitizing dyes (ExS-4, 5) | 0.07 |
| Monodispersed silver chlorobromide emulsion (EM6) spectrally sensitized with Sensitizing dyes (ExS-4, 5) | 0.16 |
| Gelatin | 1.44 |
| Cyan coupler (V-1) | 0.32 |
| Color image stabilizer (Cod-10) | 0.17 |
| Polymer for dispersion (Cpd-11) | 0.16 |
| Solvent (Solv-2) | 0.37 |
| Sixth Layer: Ultraviolet Light Absorbing Layer | |
| Gelatin | 0.54 |
| Ultraviolet light absorbing agents (UV-1) | 0.21 |
| Solvent (Solv-4) | 0.08 |
| Stabilizer (Cpd-3) | 0.02 |

-continued

| Seventh Layer: Protective Layer | |
|---|---|
| Gelatin | 1.33 |
| Acryl-modified polyvinyl alcohol copolymer (modification degree: 17 mol %) | 0.17 |
| Liquid paraffin | 0.03 |

For preventing irradiation, Irradiation Preventing Dyes (Cpd-4, 5) were used.

To all the layers, Alkanol XC (Du pont), sodium alkylbenzenesulfonate, succinic acid ester, and Magefac F-120 (Dai Nippon Ink and Chemical Co., Ltd.) were used as an emulsifying dispersing agent and a coating aid.

For stabilizing silver halide, Silver halide stabilizers (Cpd-6, 7) were used.

The compounds used in this example are illustrated below except the cyan coupler which is shown as a specific example hereinbefore.

ExS-1
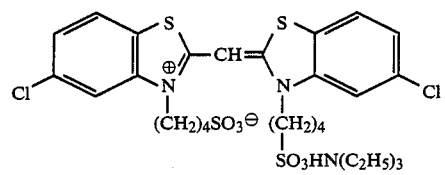

ExS-2
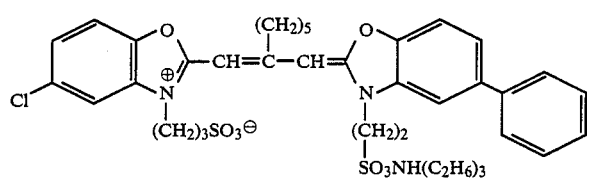

ExS-3
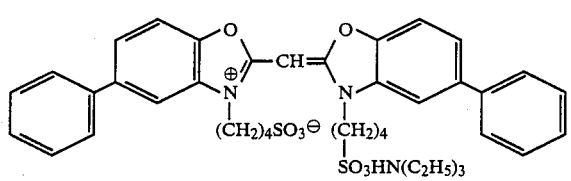

ExS-4
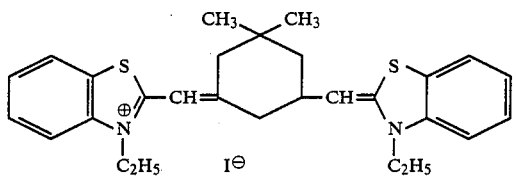

ExS-5
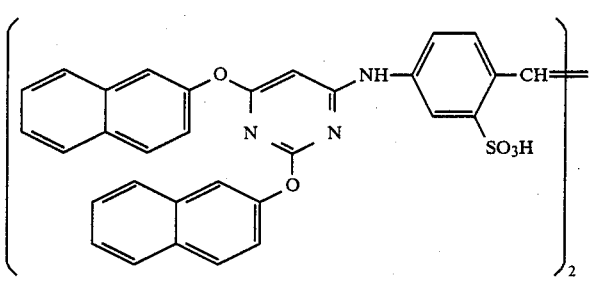

Y-1
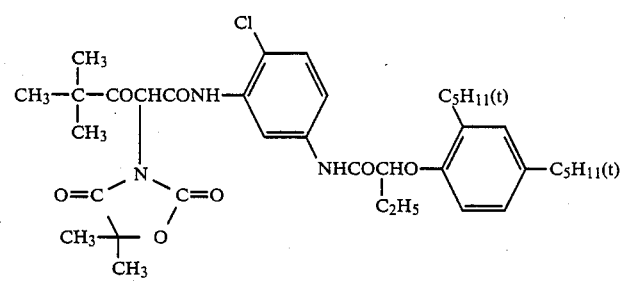

(Yellow Coupler)

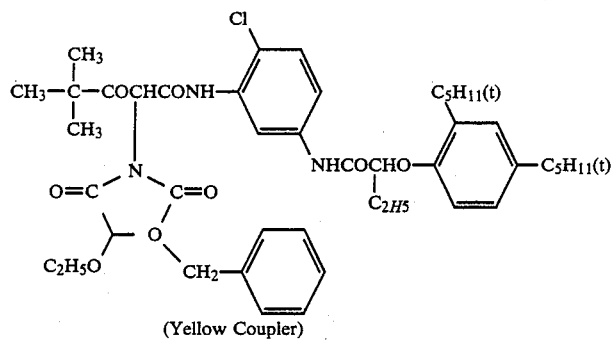
(Yellow Coupler) Y-2
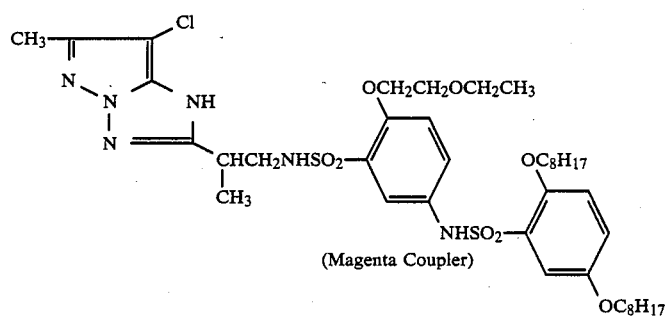
(Magenta Coupler) M-1
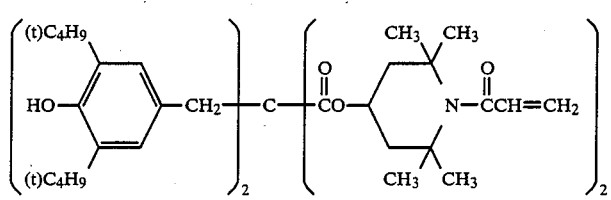
Cpd-1
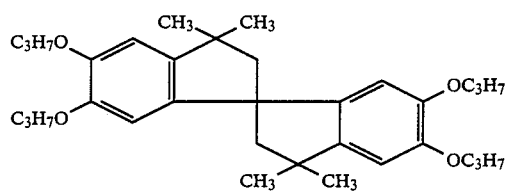
Cpd-2
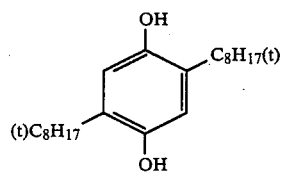
Cpd-3
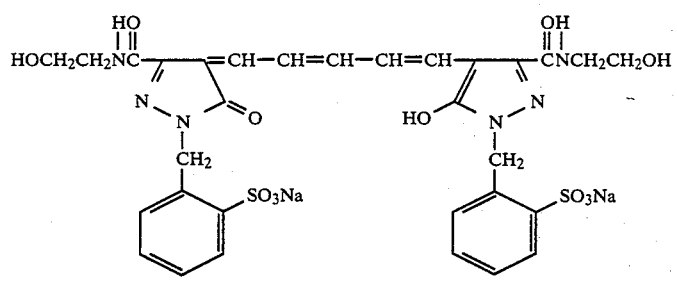
Cpd-4

-continued
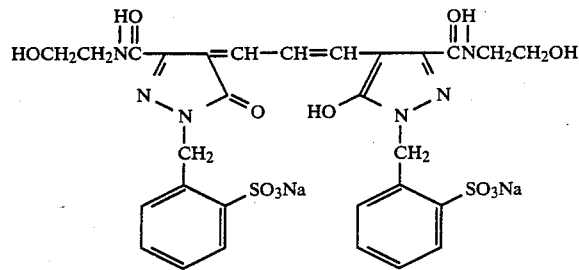
Cpd-5
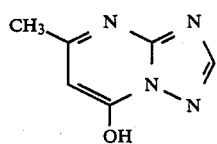
Cpd-6
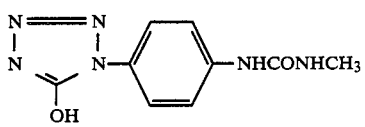
Cpd-7
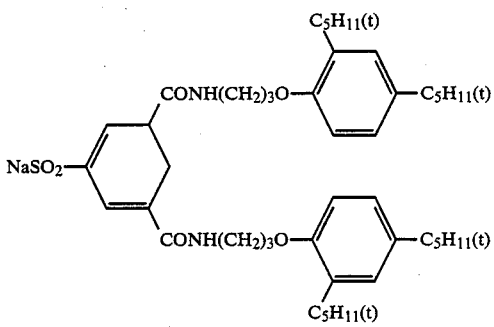
Cpd-8
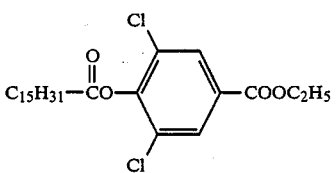
Cpd-9
A mixture of
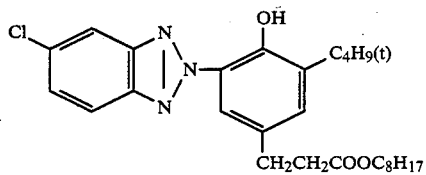 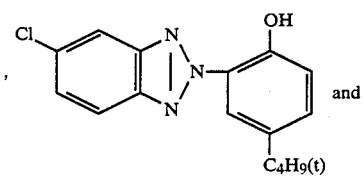 and
(Ultraviolet light absorbing agent)    UV-1
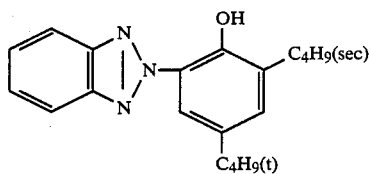
in a ratio of 2:9:8 by weight.

A mixture of

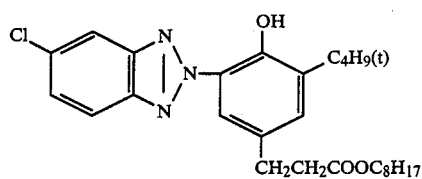

, 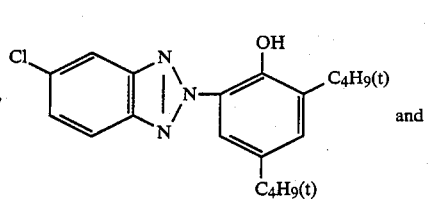 and

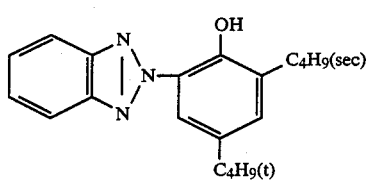

in a ratio of 5:8:9 by weight.

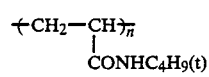   Cpd-11

Average molecular weight: 80,000

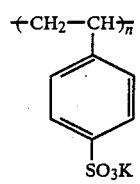   Cpd-12

| | |
|---|---|
| Dibutyl phthalate | Solv-1 |
| Tricresyl phosphate | Solv-2 |
| Trioctyl phosphate | Solv-3 |
| Trinonyl phosphate | Solv-4 |

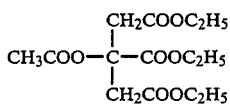   Solv-5

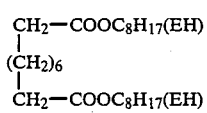   Solv-6

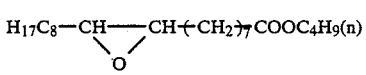   Solv-7

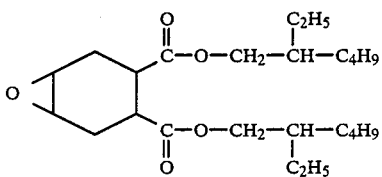   Solv-8

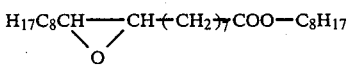   Solv-9

The silver halide emulsions used in this example are described below.

| | EM1 to EM6: Silver chlorobromide | | | |
|---|---|---|---|---|
| Emulsion | Crystal form | Grain size*1 (μm) | Bromide content (mol %) | Coefficient*2 of variation |
| EM1 | cubic | 1.0 | 80 | 0.08 |
| EM2 | cubic | 0.75 | 80 | 0.07 |
| EM3 | cubic | 0.5 | 83 | 0.09 |

-continued

| Emulsion | Crystal form | Grain size*1 (μm) | Bromide content (mol %) | Coefficient*2 of variation |
|---|---|---|---|---|
| EM1 to EM6: Silver chlorobromide | | | | |
| EM4 | cubic | 0.4 | 83 | 0.10 |
| EM5 | cubic | 0.5 | 73 | 0.09 |
| EM6 | cubic | 0.4 | 73 | 0.10 |

*1 edge length as a mean value calculated from projected areas
*2 a ratio (s/d̄) of a statistical standard deviation (s) to an average grain size (d̄)

Samples (A-2) to (A-19) were prepared in the same manner as described in the preparation of Sample (A-1) except that the cyan coupler in the Fifth layer (Redsensitive Layer) was changed to those shown in Table 2 below. The amounts of couplers were controlled to the same molar amount of coupler used in the Fifth layer of Sample (A-1). Further, a ratio of solvent (Solv-2) to coupler was adjusted 1.0 (volume/weight).

The thus-obtained samples were exposed to light through an optical wedge, and then processed according to the following Processing Method (I) or Processing Method (II).

Processing Method (I)

| Step | Temperature (°C.) | Time |
|---|---|---|
| Color Development | 38 | 1'40" |
| Bleach-Fixing | 30-34 | 1'00" |
| Rinse (1) | 30-34 | 20" |
| Rinse (2) | 30-34 | 20" |
| Rinse (3) | 30-34 | 20" |
| Drying | 70-80 | 50" |

Rinse steps were the countercurrent system from Rinse (3) to Rinse (1).

The compositions of the processing solutions used in Processing Methods (I) were as follows.

Color Developing Solution

| | |
|---|---|
| Water | 800 ml |
| Diethylenetriaminepentaacetic acid | 1.0 g |
| 1-Hydroxyethylidene-1,1-diphosphonic acid (60 wt %) | 2.0 g |
| Nitrilotriacetic acid | 2.0 g |
| Benzyl alcohol | 16 ml |
| Diethylene glycol | 10 ml |
| Sodium sulfite | 2.0 g |
| Potassium bromide | 0.5 g |
| Potassium carbonate | 30 g |
| N—Ethyl-N—(β-methanesulfonamidoethyl)-3-methyl-4-aminoaniline sulfate | 5.5 g |
| Hydroxylamine sulfate | 3.0 g |
| Fluorescent whitening agent (WHITEX 4B, Sumitomo Chemical Co., Ltd.) | 1.5 g |
| Water to make | 1,000 ml |
| pH at 25° C. | 10.25 |

Bleach-Fixing Solution

| | |
|---|---|
| Water | 400 ml |
| Ammonium thiosulfate (70 wt % soln.) | 200 ml |
| Sodium sulfite | 20 g |
| Ammonium iron (III) ethylenediaminetetraacetate | 60 g |
| Disodium ethylenediaminetetraacetate | 10 g |
| Water to make | 1,000 ml |
| pH at 25° C. | 6.50 |

Rinse Solution

| | |
|---|---|
| Benzotriazole | 1.0 g |
| Ethylenediamine-N,N,N',N'—tetramethylenephosphonic acid | 0.3 g |
| Water to make | 1,000 ml |
| pH at 25° C. | 7.50 |

Processing Method (II)

The same processing steps and the processing solutions as described in Processing Method (I) were employed except that benzyl alcohol was removed from the color developing solution used in Processing Method (I).

With respect to these samples, the difference in color forming property between using a color developing solution containing benzyl alcohol and using a color developing solution containing no benzyl alcohol was evaluated. More specifically, a reflective density of each sample was measured using a Fuji-Densitometer (MAD-8507 type) and the difference in density was determined. A difference (ΔD) between a red filter density of 2.00 obtained from Processing Method (I) and a red filter density obtained from Processing Method (II) at the exposure amount for providing the red filter density of 2.00 by Processing Method (I) and a red filter maximum density ($D^R$ max) were determined. The results obtained are shown in Table 2 below.

TABLE 2

| Sample No. | Coupler used in Fifth Layer | ΔD | $D^R_{max}$ Processing Method (I) | $D^R_{max}$ Processing Method (II) | Remark |
|---|---|---|---|---|---|
| A-1 | V-1 | −1.22 | 2.81 | 1.80 | Comparison |
| A-2 | V-2 | −1.25 | 2.72 | 1.42 | " |
| A-3 | V-5 | −0.85 | 2.76 | 2.13 | " |
| A-4 | V-8 | −1.04 | 2.83 | 1.82 | " |
| A-5 | V-10 | −0.80 | 2.68 | 1.78 | " |
| A-6 | (2) | −0.58 | 2.80 | 2.52 | Present Invention |
| A-7 | (3) | −0.52 | 2.86 | 2.66 | " |
| A-8 | (4) | −0.56 | 2.83 | 2.56 | " |
| A-9 | (8) | −0.61 | 2.83 | 2.48 | " |
| A-10 | (9) | −0.62 | 2.84 | 2.38 | " |
| A-11 | (10) | −0.58 | 2.84 | 2.44 | " |
| A-12 | (12) | −0.51 | 2.87 | 2.59 | " |
| A-13 | (19) | −0.53 | 2.84 | 2.50 | " |
| A-14 | (25) | −0.53 | 2.86 | 2.60 | " |
| A-15 | (3) and V-5 (1:1 in molar ratio) | −0.62 | 2.83 | 2.38 | Present Invention |
| A-16 | (3) and V-6 (1:1 in molar ratio) | −0.52 | 2.80 | 2.64 | " |
| A-17 | (3) and V-7 (1:1 in molar ratio) | −0.56 | 2.81 | 2.53 | " |

TABLE 2-continued

| Sample No. | Coupler used in Fifth Layer | ΔD | $D^R_{max}$ Processing Method (I) | Processing Method (II) | Remark |
|---|---|---|---|---|---|
| A-18 | (3) and V-8 (3:1 in molar ratio) | −0.56 | 2.84 | 2.50 | " |
| A-19 | (4) and V-1 (3:1 in molar ratio) | −0.63 | 2.83 | 2.37 | " |
| A-20 | (33) | −0.41 | 2.87 | 2.69 | " |
| A-21 | (34) | −0.40 | 2.86 | 2.70 | " |
| A-22 | (35) | −0.42 | 2.86 | 2.68 | " |
| A-23 | (37) | −0.41 | 2.85 | 2.67 | " |
| A-24 | (40) | −0.38 | 2.86 | 2.71 | " |
| A-25 | (41) | −0.47 | 2.85 | 2.69 | " |
| A-26 | (50) | −0.46 | 2.85 | 2.69 | " |
| A-27 | (57) | −0.41 | 2.87 | 2.68 | " |
| A-28 | (58) | −0.41 | 2.87 | 2.73 | " |

From the results shown in Table 2 it is apparent that Samples (A-1) to (A-5) for comparison provide only low color density when processed without benzyl alcohol (Processing Method (II)) and exhibit a large difference in color density as compared with the case using benzyl alcohol. On the contrary, in Samples (A-6) to (A-19) according to the present invention, the differences between the processing using benzyl alcohol and the processing using no benzyl alcohol become remarkably little.

Further, similar results to those described above were obtained when Solv-2 in the Fifth layer was replaced with each of Solv-5 to Solv-9 shown above.

EXAMPLE 3

Samples (A-1) to (A-19) as described in Example 2 were exposed to light through an optical wedge, and then subjected to color development processing according to Processing Method (I) as described in Example 2 or using running solutions of Processing Method (I) (Processing Method ((III)).

With these samples, color densities thus-obtained were measured. More specifically, a difference (ΔD) between a cyan density of 2.00 obtained from Processing Method (I) and a cyan density obtained from Processing Method (III) at the exposure amount for providing the cyan density of 2.00 by Processing Method (I) was determined and a degree of decrease in density was evaluated. The results obtained are shown in Table 3 below.

TABLE 3

| Sample No. | ΔD (I-III) | Remark |
|---|---|---|
| A-1 | 0.15 | Comparison |
| A-2 | 0.08 | Comparison |
| A-3 | 0.11 | Comparison |
| A-4 | 0.00 | Comparison |
| A-5 | 0.00 | Comparison |
| A-6 | 0.02 | Present Invention |
| A-7 | 0.02 | Present Invention |
| A-8 | 0.03 | Present Invention |
| A-9 | 0.03 | Present Invention |
| A-10 | 0.01 | Present Invention |
| A-11 | 0.02 | Present Invention |
| A-12 | 0.03 | Present Invention |
| A-13 | 0.01 | Present Invention |
| A-14 | 0.03 | Present Invention |
| A-15 | 0.04 | Present Invention |
| A-16 | 0.02 | Present Invention |
| A-17 | 0.01 | Present Invention |
| A-18 | 0.00 | Present Invention |
| A-19 | 0.01 | Present Invention |

From the results shown in Table 3, it can be seen that in Samples (A-6) to (A-19) using the coupler according to the present invention, the decrease in density is small even when processed with exhausted processing solutions due to running and these samples exhibit stable performance against the variation of processing solutions.

EXAMPLE 4

On a paper support, both surfaces of which were laminated with polyethylene were coated First Layer to Twelfth Layer as shown below in order to prepare a multilayer color photographic light-sensitive material. The polyethylene on the First Layer side contained titanium white as a white pigment and a slight amount of ultramarine as a bluish dye.

Construction of Layers

The components and the coated amounts thereof in terms of g/m² are shown below. The coated amounts of silver halide are indicated in terms of g silver /m2.

| First Layer: Gelatin Layer | |
|---|---|
| Gelatin | 1.30 |
| Second Layer: Antihalation Layer | |
| Black colloidal silver | 0.10 |
| Gelatin | 0.70 |
| Third Layer: Low-Speed Red-Sensitive Layer | |
| Silver chloroiodobromide emulsion (silver chloride: 1 mol %; silver iodide: 4 mol %; mean grain size: 0.3 μm; size distribution: 10%; cubic, core iodide type core/shell grain) spectrally sensitized with Red Sensitizing Dyes (ExS-1, 2 and 3) | 0.06 |
| Silver iodobromide emulsion (silver iodide: 5 mol %; mean grain size: 0.45 μm; size distribution: 20%; tabular (aspect ratio: 5) grain) spectrally sensitized with Red Sensitizing Dyes (ExS-1, 2 and 3) | 0.10 |
| Gelatin | 1.00 |
| Cyan coupler (ExC-1) | 0.14 |
| Cyan coupler (ExC-2) | 0.07 |
| Fading preventing agent (Cpd-2, 3, 4 and 9 in equal amounts) | 0.12 |
| Coupler dispersant (Cpd-5) | 0.03 |
| Coupler solvent (Solv-1, 2 and 3) | 0.06 |
| Fourth Layer: High-Speed Red-Sensitive Layer | |
| Silver iodobromide emulsion (silver iodide: 6 mol %; mean grain size: 0.75 μm; size distribution: 25%; tabular (aspect ratio: 8), core iodide grain) spectrally sensitized with Red Sensitizing Dyes (ExS-1, 2 and 3) | 0.15 |
| Gelatin | 1.00 |
| Cyan coupler (ExC-1) | 0.20 |
| Cyan coupler (ExC-2) | 0.10 |
| Fading preventing agent (Cpd-2, 3, 4 and 9 in equal amounts) | 0.15 |

| | |
|---|---|
| Coupler dispersant (Cpd-5) | 0.03 |
| Coupler solvent (Solv-1, 2 and 3) | 0.10 |
| Fifth Layer: intermediate Layer | |
| Magenta colloidal silver | 0.02 |
| Gelatin | 1.00 |
| Color mixing preventing agent (Cpd-6 and 7) | 0.08 |
| Color mixing preventing agent solvent (Solv-4 and 5) | 0.16 |
| Polymer Latex (Cpd-8) | 0.10 |
| Sixth Layer: Low-Speed Green-Sensitive Layer | |
| Silver chloroiodobromide emulsion (silver chloride: 1 mol %; silver iodide: 2.5 mol %; mean grain size: 0.28 μm; size distribution: 12%; cubic core iodide type core/shell grain) spectrally sensitized with Green Sensitizing Dye (ExS-3) | 0.04 |
| Silver iodobromide emulsion (silver iodide: 2.8 mol %; mean grain size: 0.45 μm; size distribution: 12%; tabular (aspect ratio: 5) grain) spectrally sensitized with Green Sensitizing Dye (ExS-3) | 0.06 |
| Gelatin | 0.80 |
| Magenta coupler (ExM-1) | 0.10 |
| Fading preventing agent (Cpd-9) | 0.10 |
| Stain preventing agent (Cpd-10) | 0.01 |
| Stain preventing agent (Cpd-11) | 0.001 |
| Stain preventing agent (Cpd-12) | 0.01 |
| Coupler dispersant (Cpd-5) | 0.05 |
| Coupler solvent (Solv-4 and 6) | 0.15 |
| Seventh Layer: High-Speed Green-Sensitive Layer | |
| Silver iodobromide emulsion (silver iodide: 3.5 mol %; mean grain size: 0.9 μm; size distribution: 23%; tabular (aspect ratio: 9), uniform iodide type grain) spectrally sensitized with Green Sensitizing Dye (ExS-3) | 0.10 |
| Gelatin | 0.80 |
| Magenta coupler (ExM-1) | 0.10 |
| Fading preventing agent (Cpd-9) | 0.10 |
| Stain preventing agent (Cpd-10) | 0.01 |
| Stain preventing agent (Cpd-11) | 0.001 |
| Stain preventing agent (Cpd-12) | 0.01 |
| Coupler dispersant (Cpd-5) | 0.05 |
| Coupler solvent (Solv-4 and 6) | 0.15 |
| Eighth Layer: Yellow Filter Layer | |
| Yellow colloidal silver | 0.20 |
| Gelatin | 1.00 |
| Color mixing preventing agent (Cpd-7) | 0.06 |
| Color mixing preventing agent solvent (Solv-4 and 5) | 0.15 |
| Polymer Latex (Cpd-8) | 0.10 |
| Ninth Layer: Low-Speed Blue-Sensitive Layer | |
| Silver chloroiodobromide emulsion (silver chloride: 2 mol %; silver iodide: 2.5 mol %; mean grain size: 0.35 μm; size distribution: 8%; cubic, core iodide type core/shell grain) spectrally sensitized with Blue Sensitizing Dyes (ExS-5 and 6) | 0.07 |
| Silver iodobromide emulsion (silver iodide: 2.5 mol %; mean grain size: 0.45 μm; size distribution: 16%; tabular (aspect ratio: 6) grain) spectrally sensitized with Blue Sensitizing Dyes (ExS-5 and 6) | 0.10 |
| Gelatin | 0.50 |
| Yellow coupler (ExY-1) | 0.20 |
| Stain preventing agent (Cpd-11) | 0.001 |
| Fading preventing agent (Cpd-6) | 0.10 |
| Coupler dispersant (Cpd-5) | 0.05 |
| Coupler solvent (Solv-2) | 0.05 |
| Tenth Layer: High-Speed Blue-Sensitive Layer | |
| Silver iodobromide emulsion (silver iodide: 2.5 mol %; mean grain size: 1.2 μm; size distribution: 21%; tabular (aspect ratio: 14) grain) spectrally sensitized with Blue Sensitizing Dyes (ExS-5 and 6) | 0.25 |
| Gelatin | 1.00 |
| Yellow coupler (ExY-1) | 0.40 |
| Stain preventing agent (Cpd-11) | 0.002 |
| Fading preventing agent (Cpd-6) | 0.10 |
| Coupler dispersant (Cpd-5) | 0.05 |
| Coupler solvent (Solv-2) | 0.10 |
| Eleventh Layer: Ultraviolet Light Absorbing Layer | |
| Gelatin | 1.50 |
| Ultraviolet light absorbing agent (Cpd-1, 3 and 13) | 1.00 |
| Color mixing preventing agent (Cpd-6 and 14) | 0.06 |
| Dispersant (Cpd-5) | |
| Ultraviolet light absorbing agent solvent (Solv-1 and 2) | 0.15 |
| Anti-irradiation dye (Cpd-15 and 16) | 0.02 |
| Anti-irradiation dye (Cpd-17 and 18) | 0.02 |
| Twelfth Layer: Protective Layer | |
| Fine silver chlorobromide grains (silver chloride: 97 mol %; mean grain size, 0.2 μm) | 0.07 |
| Modified poval | 0.02 |
| Gelatin | 1.50 |
| Gelatin hardener (H-1) | 0.17 |

Each of the layers contained Alkanol XC (Du pont) and sodium alkylbenzenesulfonate as emulsifying dispersing aids, and a succinic acid ester and Magfac F-120 (Dai Nippon Ink and Chemical Co. Ltd.) as coating aids. In the layers containing silver halide or colloidal silver, Stabilizer (Cpd-19, 20 and 21) were employed.

The compounds used in this example are illustrated below.

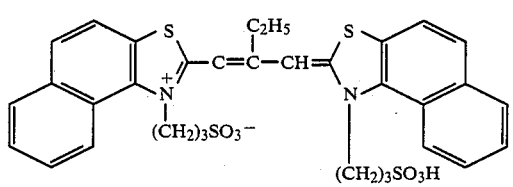

ExS-1

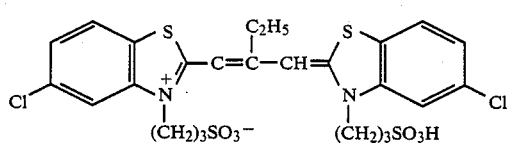

ExS-2

-continued
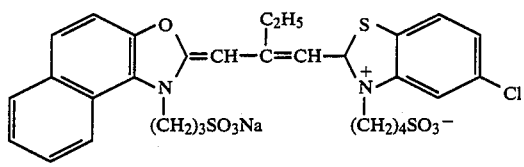 ExS-3
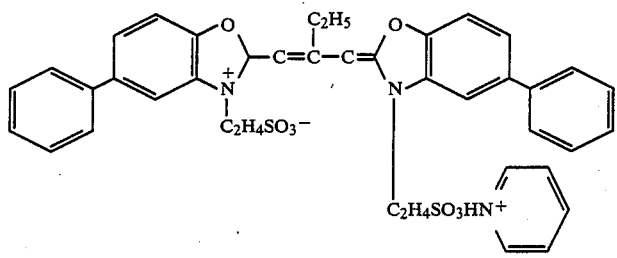 ExS-4
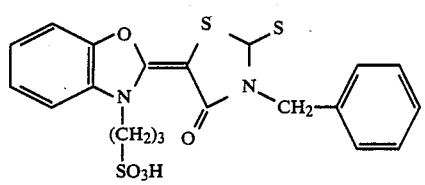 ExS-5
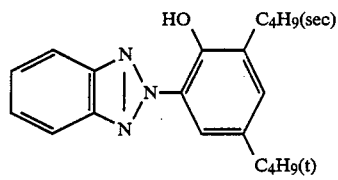 Cpd-1
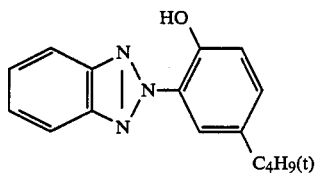 Cpd-2
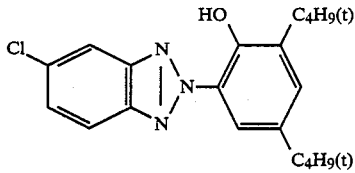 Cpd-3
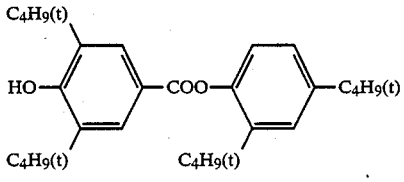 Cpd-4
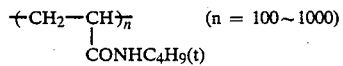 Cpd-5
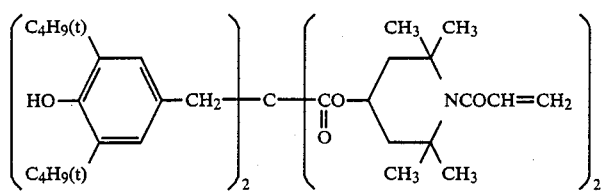 Cpd-6

-continued
Cpd-7
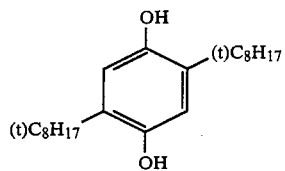
Cpd-8
Polyethyl acrylate
Cpd-9
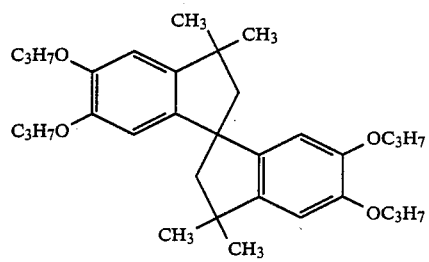
Cpd-10
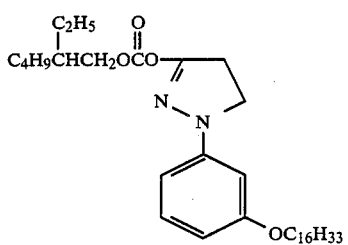
Cpd-11
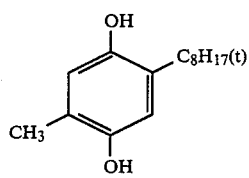
Cpd-12
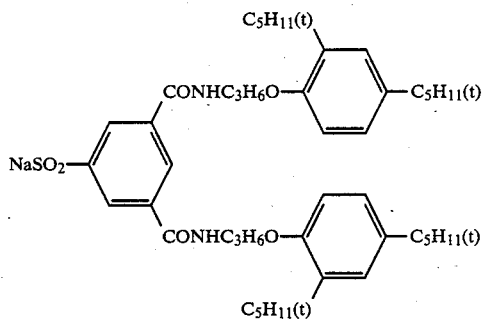
Cpd-13
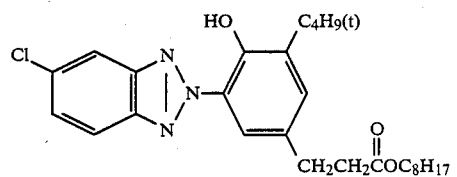
Cpd-14
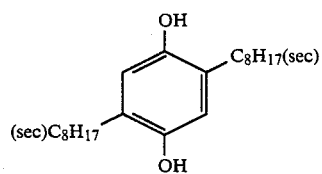

-continued
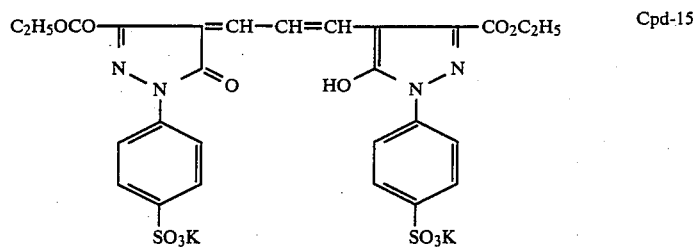 Cpd-15
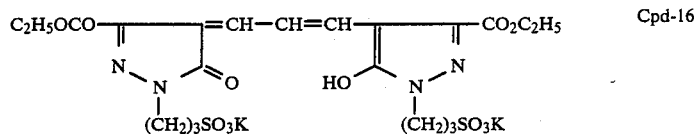 Cpd-16
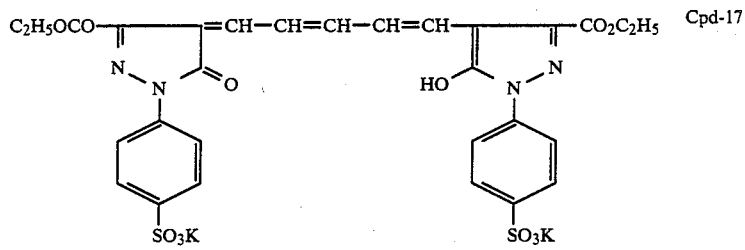 Cpd-17
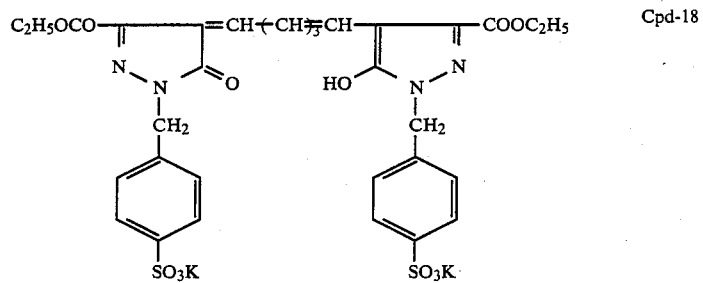 Cpd-18
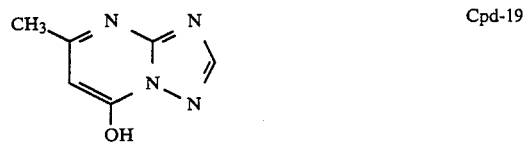 Cpd-19
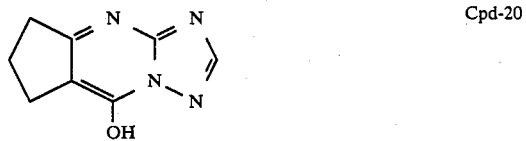 Cpd-20
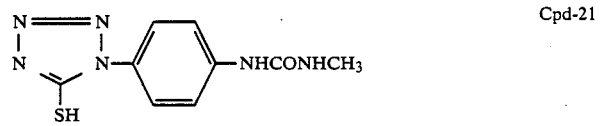 Cpd-21
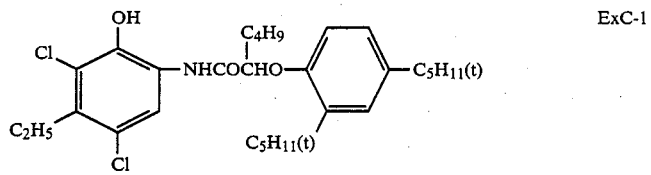 ExC-1

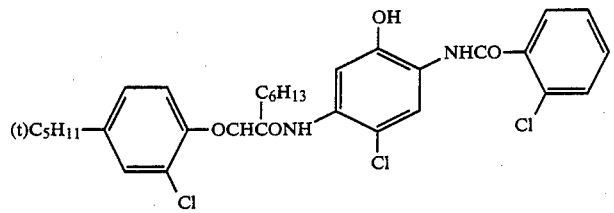
ExC-2

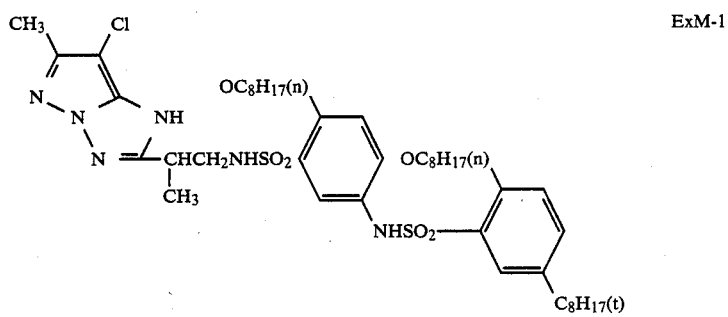
ExM-1

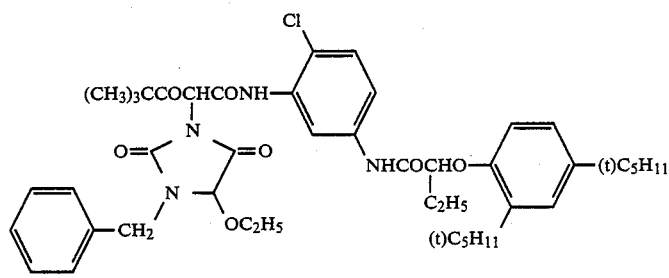
ExY-1

| | |
|---|---|
| Di(2-ethylhexyl)phthalate | Solv-1 |
| Trinonyl phosphate | Solv-2 |
| Di(3-methylhexyl)phthalate | Solv-3 |
| Tricresyl phosphate | Solv-4 |
| Dibutyl phthalate | Solv-5 |
| Trioctyl phosphate | Solv-6 |
| 1,2-Bis(vinylsulfonylacetamido)ethane | H-1 |

The sample thus-prepared was designated Sample (B-1) and used as a comparative sample.

Samples (B-2) and (B-3) were prepared in the same manner as described for Sample (B-1) except using the equimolar amounts of Couplers (2) and (3) according to the present invention in place of Cyan Couplers (ExC-1) and (ExC-2) used in the third layer and the fourth layer of Sample (B-1) respectively.

The samples thus-prepared were exposed to light through an optical wedge, and then processed according to the following processing method.

| Processing Steps | Temperature | Time |
|---|---|---|
| First Development (Black and white development) | 38° C. | 75 sec |
| Washing with Water | 38° C. | 90 sec |
| Reversal Exposure | 100 lux or more | 60 sec or more |
| Color Development | 38° C. | 135 sec |
| Washing with Water | 38° C. | 45 sec |
| Bleach-Fixing | 38° C. | 120 sec |

| -continued | | |
|---|---|---|
| Processing Steps | Temperature | Time |
| Washing with Water | 38° C. | 135 sec |

The processing solutions used had the following compositions.

| First Developing Solution | |
|---|---|
| Pentasodium nitrilo-N,N,N—trimethylene-phosphonate | 0.6 g |
| Pentasodium diethylenetriaminepentaacetate | 4.0 g |
| Potassium sulfite | 30.0 g |
| Potassium thiocyanate | 1.2 g |
| Potassium carbonate | 35.0 g |
| Potassium hydroquinonemonosulfonate | 25.0 g |
| Diethylene glycol | 15.0 ml |
| 1-Phenyl-4-hydroxymethyl-4-methyl-3-pyrazolidone | 2.0 g |
| Potassium bromide | 0.5 g |
| Potassium iodide | 5.0 mg |
| Water to make | 1 l |
| | (pH 9.70) |
| Color Developing Solution | |

-continued

| | |
|---|---|
| Benzyl alcohol | 15.0 ml |
| Diethylene glycol | 12.0 ml |
| 3,6-Dithia-1,8-octanediol | 0.2 g |
| Nitrilo-N,N,N—trimethylenephosphonate | 0.5 g |
| Pentasodium diethylenetriaminepentaacetate | 2.0 g |
| Sodium sulfite | 2.0 g |
| Potassium carbonate | 25.0 g |
| Hydroxylamine sulfate | 3.0 g |
| N—Ethyl-N—(β-methanesulfonamidoethyl)-3-methyl-4-aminoaniline sulfate | 5.0 g |
| Potassium bromide | 0.5 g |
| Potassium iodide | 1.0 mg |
| Water to make | 1 l |
| | (pH 10.40) |
| Bleach-Fixing Solution | |
| 2-Mercapto-1,3,4-triazole | 1.0 g |
| Disodium ethylenediaminetetraacetate/dihydrate | 5.0 g |
| Ammonium ethylenediaminetetraacetate/Fe(III)/monohydrate | 80.0 g |
| Sodium sulfite | 15.0 g |
| Ammonium thiosulfate (700 g/l-solution) | 160.0 ml |
| Glacial acetic acid | 5.0 ml |
| Water to make | 1 l |
| | (pH 6.50) |

Then, each film thus processed was subjected to examination with respect to fastness. More specifically, the samples were left for 6 days in a dark place at 100° C., the samples were left for 6 weeks in a dark place at 60° C. and 70% RH and the samples were irradiated for 6 days in a xenon test apparatus (100,000 luxes) and a density reduction rate of the sample in the area where the initial density was 1.0 was measured. Furthermore, with respect to yellow coloration of white background areas, the samples were left for 6 days in a dark at 100° C. and the samples were irradiated for 6 days in the xenon test apparatus and increase in blue density of unexposed areas was measured. The results thus-obtained are shown in Table 4 below.

TABLE 4

| Film Sample | Coupler | Fastness of Color Image | | | Yellow Coloration of White Background | |
|---|---|---|---|---|---|---|
| | | 100° C. 6 Days (%) | 60° C. 70% RH 6 Weeks (%) | Light (Xenon) 6 Days (%) | 100° C. 6 Days | Light (Xenon) 6 Days |
| (B-1) | ExC-1 and 2 (Comparison) | 30 | 22 | 18 | +0.07 | +0.05 |
| (B-2) | (2) (Present Invention) | 8 | 10 | 5 | +0.08 | +0.05 |
| (B-3) | (3) (Present Invention) | 7 | 7 | 2 | +0.06 | +0.04 |

From the results shown in Table 4, it is apparent that the couplers according to the present invention are extremely fast to heat and light in comparison with the comparative coupler.

EXAMPLE 5

On a paper support, both surfaces of which were laminated with polyethylene were coated the layers as shown below to prepare a multilayer silver halide photographic material, which was designated Sample A. The coating solutions were prepared as follows.

Preparation of the coating solution for the First Layer 19.1 g of Yellow coupler (ExY-1), and 4.4 g of Dye image stabilizer (Cdp-1) were dissolved in 27.2 ml of ethyl acetate and 7.7 ml (8.0 g) of High boiling point solvent (Solv-1). This solution was emulsified and dispersed in 185 ml of a 10 wt % gelatin aqueous solution containing 8 ml of a 10 wt % aqueous solution of sodium dodecylbenzenesulfonate. Emulsions (EM7) and (EM8) described hereinafter were mixed with thus-obtained emulsified dispersion, and the gelatin concentration was adjusted whereby the composition became the following to obtain the coating solution for the First Layer.

The coating solutions for the Second to Seventh Layers were prepared in the same manner as described in the coating solution for the First Layer.

In all the coating solutions, 1-oxy-3,5-dichloro-s-triazine sodium salt was used as a gelatin hardener. Further, Viscosity imparting agent (Cpd-2) was used in the coating solutions.

Construction of Layers

The compositions of the layers are described below. The coated amounts are indicated in terms of g/m$^2$ provided that the coated amounts of the silver halide emulsions are indicated in terms of g silver/m$^2$. Support:

Polyethylene laminated paper support in which the polyethylene on the First Layer side contained a white pigment (TiO$_2$) and a blueish dye

| First Layer: Blue-sensitive Layer | |
|---|---|
| Monodispersed silver chlorobromide emulsion (EM7) spectrally sensitized with Sensitizing dye (ExS-1) | 0.15 |
| Monodispersed silver chlorobromide emulsion (EM8) spectrally sensitized with Sensitizing dye (ExS-1) | 0.15 |
| Gelatin | 1.86 |
| Yellow coupler (ExY-1) | 0.82 |
| Color image stabilizer (Cpd-1) | 0.19 |
| Solvent (Solv-1) | 0.35 |
| Second Layer: Color-mixing Preventing Layer | |
| Gelatin | 0.99 |
| Color mixing preventing agent (Cpd-3) | 0.08 |
| Third Layer: Green-sensitive Layer | |
| Monodispersed silver chlorobromide emulsion (EM9) spectrally sensitized with Sensitizing dyes (ExS-2, 3) | 0.12 |
| Monodispersed silver chlorobromide emulsion (EM10) spectrally sensitized with Sensitizing dyes (ExS-2, 3) | 0.24 |
| Gelatin | 1.24 |
| Magenta coupler (ExM-1) | 0.39 |
| Color image stabilizer (Cpd-4) | 0.25 |
| Color image stabilizer (Cpd-5) | 0.12 |
| Solvent (Solv-2) | 0.25 |
| Fourth Layer: Ultraviolet Light Absorbing Layer | |
| Gelatin | 0.16 |
| Ultraviolet light absorbing agent (Cpd-6/Cpd-7/Cpd-8 = 3/2/6 by weight ratio) | 0.70 |
| Color mixing preventing agent (Cpd-9) | 0.05 |
| Solvent (Solv-3) | 0.42 |
| Fifth Layer: Red-sensitive Layer | |
| Monodispersed silver chlorobromide emulsion (EM11) spectrally sensitized with Sensitizing dyes (ExS-4, 5) | 0.07 |
| Monodispersed silver chlorobromide emulsion (EM12) spectrally sensitized with Sensitizing dyes (ExS-4, 5) | 0.16 |
| Gelatin | 0.92 |
| Cyan coupler (ExC-1) | 0.15 |
| Cyan coupler (ExC-2) | 0.18 |
| Color image stabilizer (Cpd-7/Cpd-8 Cpd-10 = 3/4/2 by weight ratio) | 0.17 |
| Polymer for dispersion (Cpd-11) | 0.14 |
| Solvent (Solv-1) | 0.20 |
| Sixth Layer: Ultraviolet Light Absorbing Layer | |
| Gelatin | 0.54 |
| Ultraviolet light absorbing agent (Cpd-6/Cpd-8/Cpd-10 = 1/5/3 by weight | 0.21 |

| | | -continued | |
|---|---|---|---|
| ratio) | | | |
| Solvent (Solv-4) | | | 0.08 |
| Seventh Layer: Protective Layer | | | |
| Gelatin | | | 1.33 |
| Acryl-modified polyvinyl alcohol copolymer (modification degree: 17 mol %) | | | 0.17 |
| Liquid paraffin | | | 0.03 |

For preventing irradiation, Irradiation preventing dyes (Cpd-12, 13) were used.

To all the layers, Alkanol XC (Du Pont Co.), sodium alkylbenzenesulfonate, succinic acid ester, and Megafac F-120 (Dai Nippon Ink and Chemical Co., Ltd.) were used as an emulsifying dispersing agent and a coating aid.

For stabilizing silver halide, Silver halide stabilizers (Cpd-14, 15) were used.

The emulsions used are specifically shown below.

| Emulsion | Crystal form | Grain size ($\mu$m) | Bromide content (mol %) | Coefficient of variation |
|---|---|---|---|---|
| EM7 | cubic | 1.1 | 1.0 | 0.10 |
| EM8 | cubic | 0.8 | 1.0 | 0.10 |
| EM9 | cubic | 0.45 | 1.5 | 0.09 |
| EM10 | cubic | 0.34 | 1.5 | 0.09 |
| EM11 | cubic | 0.45 | 1.5 | 0.09 |
| EM12 | cubic | 0.34 | 1.6 | 0.10 |

Coefficient of variation = standard derivation/average grain size

The compounds used are illustrated below.

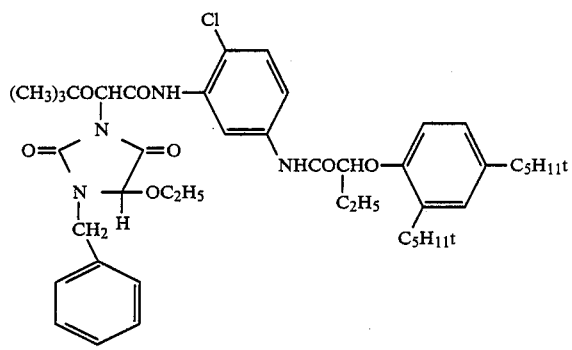

ExY-1

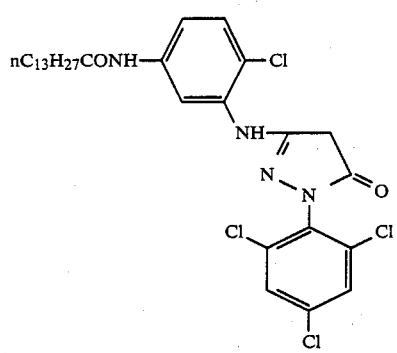

ExM-1

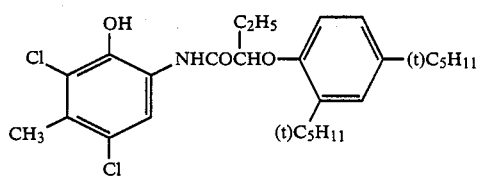

ExC-1

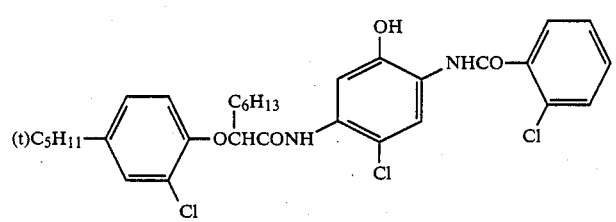

ExC-2

-continued
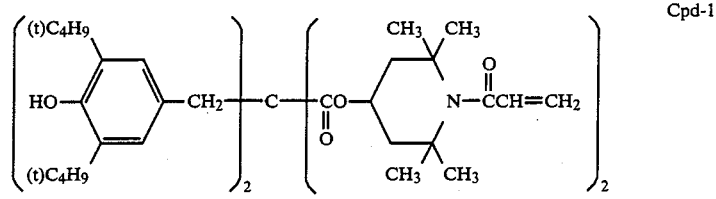 Cpd-1
 Cpd-2
 Cpd-3
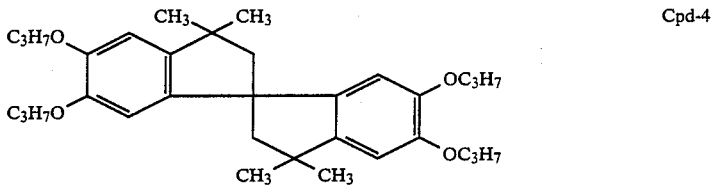 Cpd-4
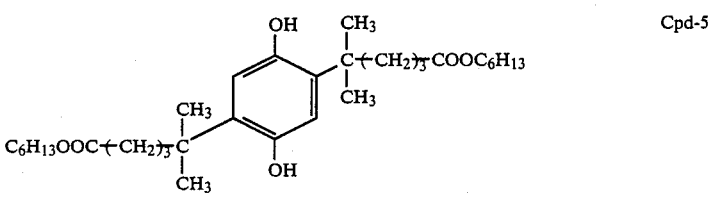 Cpd-5
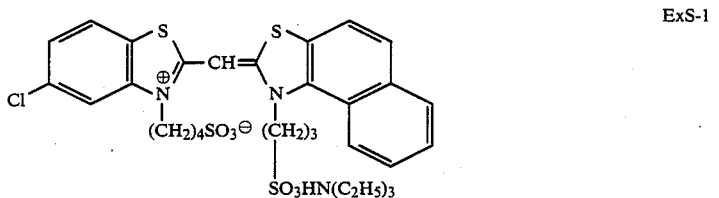 ExS-1
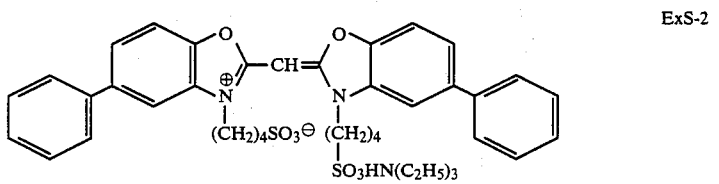 ExS-2
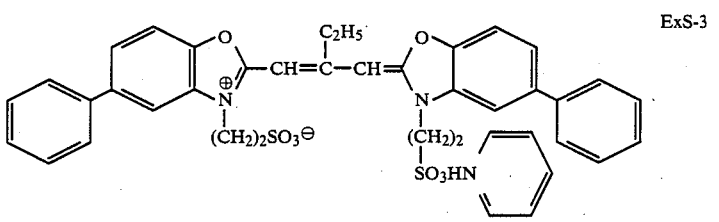 ExS-3

-continued
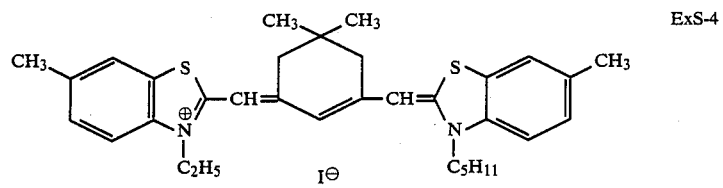 ExS-4
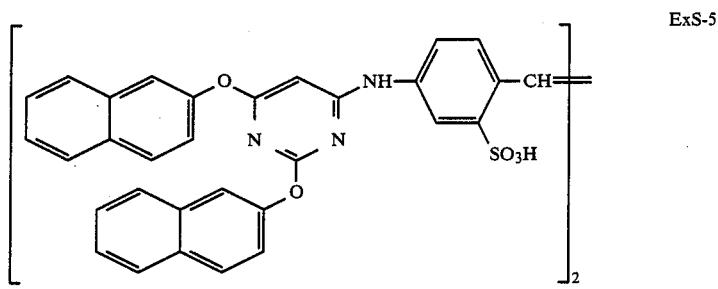 ExS-5
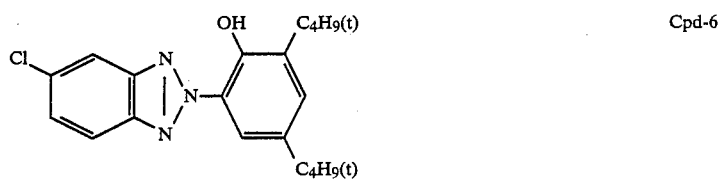 Cpd-6
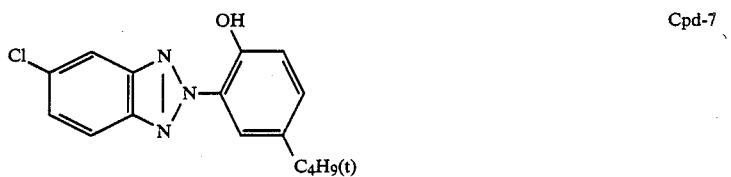 Cpd-7
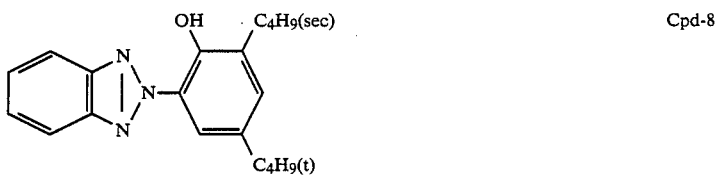 Cpd-8
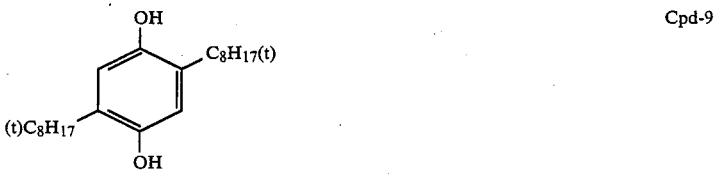 Cpd-9
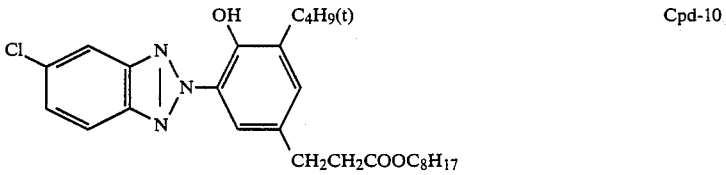 Cpd-10
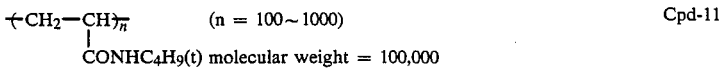 Cpd-11

-continued

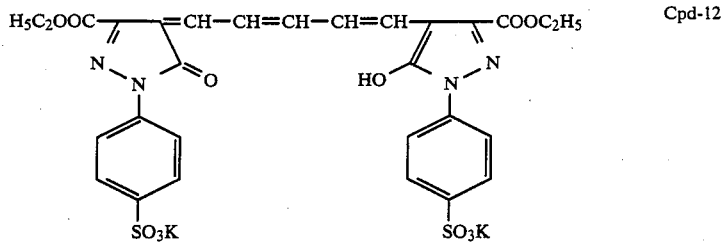
Cpd-12

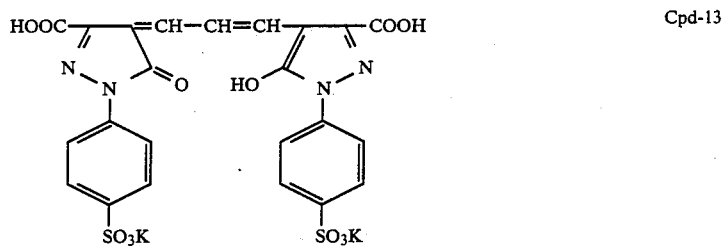
Cpd-13

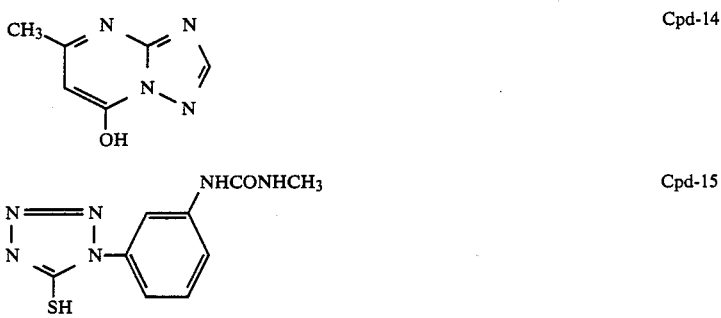

Cpd-14

Cpd-15

| | |
|---|---|
| Dibutyl phthalate | Solv-1 |
| Trioctyl phosphate | Solv-2 |
| Trinonyl phosphate | Solv-3 |
| Tricresyl phosphate | Solv-4 |

Samples B to O were prepared in the same manner as described for Sample A above except changing the cyan couplers used in the fifth layer to those shown in Table 5 below.

The photographic light-sensitive materials thus-prepared were imagewise exposed to light and then subjected to development processing according to the following processing steps.

| Processing Steps | Temperature | Time |
|---|---|---|
| Color Development | 35° C. | 45 sec |
| Bleach-Fixing | 30 to 35° C. | 45 sec |
| Rinse (1) | 30 to 35° C. | 20 sec |
| Rinse (2) | 30 to 35° C. | 20 sec |
| Rinse (3) | 30 to 35° C. | 20 sec |
| Rinse (4) | 30 to 35° C. | 30 sec |
| Drying | 70 to 80° C. | 60 sec |

Rinse steps were conducted using a four-tank countercurrent system from Rinse (4) to Rinse (1).

The composition of each processing solution used was as follows:

| Color Developing Solution | |
|---|---|
| Water | 800 ml |
| Ethylenediamine N,N,N',N'—tetramethylene phosphonic acid | 1.5 g |
| Triethylenediamine (1,4-diazabicyclo[2,2,2]octane | 5.0 g |
| Sodium chloride | 1.4 g |

| -continued | |
|---|---|
| Potassium carbonate | 25.0 g |
| N—Ethyl-N—($\beta$-methanesulfonamidoethyl)-3-methyl-4-aminoaniline sulfate | 5.0 g |
| N,N—Diethylhydroxyamine | 4.2 g |
| Fluorescent brightening agent (UVITEX-CK manufactured by Ciba-Geigy Co.) | 2.0 g |
| Water to make | 1000 ml |
| pH (25° C.) | 10.10 |
| Bleach-Fixing Solution | |
| Water | 1000 ml |
| Ammonium thiosulfate (70 wt %) | 100 ml |
| Sodium sulfite | 18 g |
| Ammonium ethylenediaminetetraacetato iron (III) | 55 g |
| Disodium ethylenediaminetetraacetate | 3 g |
| Ammonium bromide | 40 g |
| Glacial acetic acid | 8 g |
| Water to make | 1000 ml |
| pH (25° C.) | 6.0 |
| Rinse Solution | |

Iron exchange water (contents of calcium and magnesium each having not more than 3 ppm).

Cyan reflective density at the $D_{max}$ area of each sample just after processing was measured, then the samples were immersed in a processing agent (CN-16, N-2 manufactured by Fuji Photo Film Co., Ltd.) at 30° C. for 4 minutes and thereafter cyan reflective density of each sample was again measured. The results thus obtained are shown in Table 5 using a color forming rate which is defined as follows.

TABLE 5

Color forming rate = Cyan density before re-processing/
Cyan density after re-processing × 100

| Sample | Cyan Coupler | Color Forming Rate (%) | Remark |
|---|---|---|---|
| A | V-1/V-8 (1:1 in molar ratio) | 80 | Comparison |
| B | (2) | 87 | Present Invention |
| C | (3) | 88 | Present Invention |
| D | (4) | 90 | Present Invention |
| E | (9) | 91 | Present Invention |
| F | (25) | 90 | Present Invention |
| G | (33) | 94 | Present Invention |
| H | (34) | 95 | Present Invention |
| I | (35) | 95 | Present Invention |
| J | (37) | 94 | Present Invention |
| K | (40) | 95 | Present Invention |
| L | (41) | 94 | Present Invention |
| M | (50) | 96 | Present Invention |
| N | (57) | 96 | Present Invention |
| O | (58) | 95 | Present Invention |

From the results shown in Table 5 it can be seen that the formation of leuco form of cyan dye is remarkably restrained in the case of using the cyan coupler according to the present invention.

EXAMPLE 6

On a paper support, both surfaces of which were laminated with polyethylene subjected to corona discharge treatment, a first layer (the undermost layer) to a seventh layer (the uppermost layer) were coated as shown below to prepare a photographic light-sensitive material. The coating solution of each layer was prepared in the manner as described below. The couplers, dye image stabilizers, etc. used in the coating solutions are also described below.

The coating solution for the first layer was prepared in the following manner.

A mixture of 200 g of Yellow Coupler, 93.3 g of Color Fading Preventing Agent (r), 10 g of Solvent (p) having a high boiling point, 5 g of Solvent (q) having a high boiling point and 600 ml of ethyl acetate as an auxiliary solvent was dissolved by heating at 60° C. The solution was mixed with 3,300 ml of a 5 wt % aqueous solution of gelatin containing 330 ml of a 5 wt % aqueous solution of Alkanol B (alkylnaphthalenesulfonate manufactured by du Pont Co.) and emulsified using a colloid mill to prepare a coupler dispersion. From the dispersion ethyl acetate was distilled off under a reduced pressure and then the dispersion was added to 1,400 g of silver halide emulsion (containing 96.7 g of silver and 170 g of gelatin) containing a sensitizing dye for a blue-sensitive emulsion layer and 1-methyl-2-mercapto-5-acetylamino-1,3,4-triazole. Further, 2,600 g of a 10% aqueous solution of gelatin was added thereto to prepare the coating solution.

Coating solutions for the second layer to the seventh layer were prepared in a similar manner as described for the coating solution for the first layer.

Construction of Layers

The Compositions of the layers are described below. The coated amounts are indicated in terms of mg/m² provided that the coated amounts of the silver halide emulsions are indicated in terms of silver coated amount.

| | | |
|---|---|---|
| Support | Paper support, both surfaces of which were laminated with polyethylene | |
| First layer (Blue-sensitive layer) | Silver chlorobromide emulsion (silver bromide: 80 mol %) | 290 |
| | Yellow coupler | 600 |
| | Color fading preventing agent (r) | 280 |
| | Solvent (p) | 30 |
| | Solvent (q) | 15 |
| | Gelatin | 1,800 |
| Second Layer (Color mixing preventing layer) | Silver bromide emulsion (non-after ripening, particle size: 0.05 μ) | 10 |
| | Color mixing preventing agent (s) | 55 |
| | Solvent (p) | 30 |
| | Solvent (q) | 15 |
| | Gelatin | 800 |
| Third Layer (Green-sensitive layer) | Silver chlorobromide emulsion (silver bromide: 70 mol %) | 305 |
| | Magenta coupler | 670 |
| | Color fading preventing agent (t) | 150 |
| | Color fading preventing agent (u) | 10 |
| | Solvent (p) | 200 |
| | Solvent (q) | 10 |
| | Gelatin | 1,400 |
| Fourth Layer (Color mixing preventing layer) | Color mixing preventing agent (s) | 65 |
| | Ultraviolet light absorbing agent (n) | 450 |
| | Ultraviolet light absorbing agent (o) | 230 |
| | Solvent (p) | 50 |
| | Solvent (q) | 50 |
| | Gelatin | 1,700 |
| Fifth Layer (Red-sensitive layer) | Silver chlorobromide emulsion (silver bromide: 70 mol %) | 210 |
| | Cyan coupler | 320 |
| | Color fading preventing agent (r) | 250 |
| | Solvent (p) | 160 |
| | Solvent (q) | 100 |
| | Gelatin | 1,800 |
| Sixth Layer (Ultraviolet light absorbing layer) | Ultraviolet light absorbing agent (n) | 260 |
| | Ultraviolet light absorbing agent (o) | 70 |
| | Solvent (p) | 300 |
| | Solvent (q) | 100 |
| | Gelatin | 1,000 |
| Seventh Layer (Protective layer) | Gelatin | 620 |

(n): 2-(2-Hydroxy-3,5-di-tert-amylphenyl)benzotriazole
(o): 2-(2-Hydroxy-3,5-di-tert-butylphenyl)benzotriazole
(p): Di-(2-ethylhexyl)phthalate
(q): Dibutyl phthalate
(r): 2,5-Di-tert-amylphenyl-3,5-di-tert-butyl-hydroxybenzoate
(s): 2,5-Di-tert-octylhydroquinone
(t): 1,4-Di-tert-amyl-2,5-di-octyloxybenzene
(u): 2,2'-Methylenebis(4-methyl-6-tert-butyl-phenol)

Further, the following spectral sensitizing dyes were employed in the emulsion layers, respectively.
Blue-Sensitive Emulsion Layer:

Anhydro-5-methoxy-5'-methyl-3,3'-disulfopropyl-
selenacyanine hydroxide

Green-Sensitive Emulsion Layer:

Anhydro-9-ethyl-5,5'-diphenyl-3,3'-disulfoethyloxacar-
bocyanine hydroxide

Red-Sensitive Emulsion Layer:

3,3'-Diethyl-5-methoxy-9,9'-(2,2-dimethyl-1,3-
propane)thiadicarbocyanine iodide As a stabilizer for each emulsion layer, 1-methyl-2-mercapto-5-acetylamino-1,3,4-triazole was employed.

The following irradiation preventing dyes were employed.

4-[3-Carboxy-5-hydroxy-4-{3-[3-carboxy-5-oxo-1-(4-sulfonatophenyl)-2-pyrazolin-4-ylidene]-1-propenyl}-1-pyrazolyl]benzenesulfonate dipotassium salt N,N'-(4,8-Dihydroxy-9,10-dioxo-3,7-disulfonatoanthracene-1,5-diyl)bis(aminomethanesulfonate) tetrasodium salt.

Moreover, as a hardening agent, 1,2-bis(vinylsulfonyl)ethane was employed.

The couplers employed were as follows:

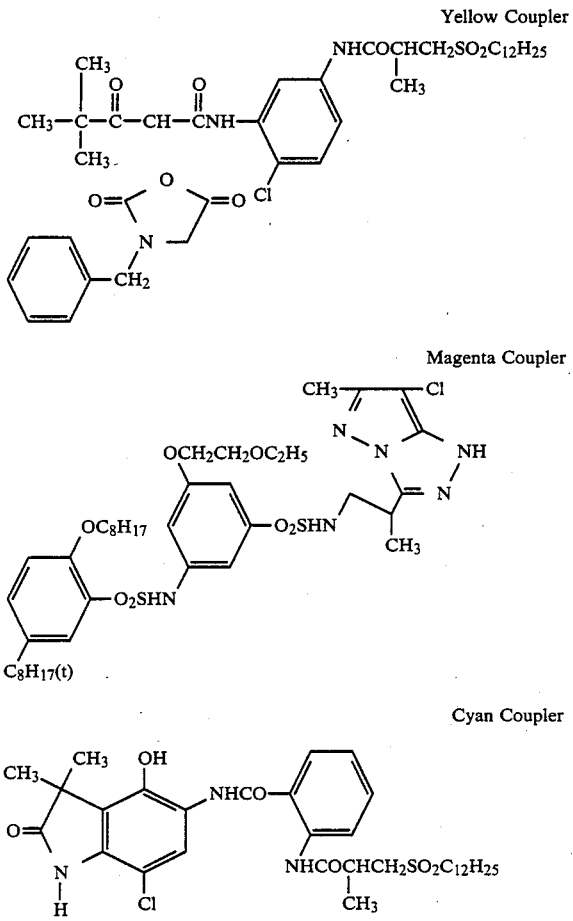

Other photographic light-sensitive materials were prepared in the same manner as described above except using Couplers (3), (4), (9), (25), (35), (50), (56) and (58) according to the present invention in place of the cyan coupler used in the fifth layer, respectively. These samples were subjected to development processing in the same manner as described in Example 2 to obtain similar results to those described in Example 2.

As explained in detail hereinbefore, the photographic light-sensitive material using the cyan dye forming coupler according to the present invention has excellent color forming property, forms a good color image particularly in processing without using benzyl alcohol in a color developing solution, and exhibits only a little change in color density formed even when an exhausted processing solution is used. Further, a print obtained therefrom exhibites only a little degradation of image such as yellow coloration of white background areas when it is left under the condition of exposure to light and heat, and has both excellent heat stability, humidity and heat stability and light stability which has hitherto not been achieved, and thus the print has excellent image stability even preserved for a long period of time.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having coated thereon at least one silver halide emulsion layer, the silver halide color photographic material containing a photographic cyan dye forming coupler represented by the following general formula (I):

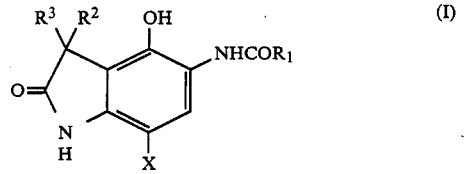

wherein $R_1$ represents an aliphatic group, an aromatic group, heterocyclic group or a substituted amino group; $R_2$ and $R_3$, which may be the same or different, each represents an aliphatic group, an aromatic group or a heterocyclic group, or $R_2$ and $R_3$ may combine with each other to form a ring; and X represents a group capable of being released upon an oxidative coupling with a developing agent.

2. A silver halide color photographic material as claimed in claim 1, wherein a substituent for the aliphatic group, aromatic group, heterocyclic group or substituted amino group is selected from an alkyl group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, a sulfonamido group, an acylamino group, a diacylamino group, a sulfonyl group, a hydroxy group, a cyano group, a nitro group and a halogen atom.

3. A silver halide color photographic material as claimed in claim 1, wherein the group represented by X is a hydrogen atom, a halogen atom, an alkoxy group, an aryloxy group, an acyloxy group, a sulfonyloxy group, an amido group, an alkoxycarbonyloxy group, an aryloxycarbonyloxy group, an aliphatic or aromatic thio group, an imido group or an aromatic azo group.

4. A silver halide color photographic material as claimed in claim 3, wherein X is a hydrogen atom, a halogen atom, an aryloxy group, an arylthio group, an alkoxy group or a sulfonamido group.

5. A silver halide color photographic material as claimed in claim 4, wherein X is a hydrogen atom, a fluorine atom, a chlorine atom or an aryloxy group.

6. A silver halide color photographic material as claimed in claim 4, wherein X is a chlorine atom or a substituted phenoxy group.

7. A silver halide color photographic material as claimed in claim 1, wherein $R_1$ represents an alkyl group having from 3 to 22 carbon atoms or an aryl group.

8. A silver halide color photographic material as claimed in claim 7, wherein $R_1$ represents a substituted phenyl group.

9. A silver halide color photographic material as claimed in claim 8, wherein $R_1$ is a m-sulfonamidophenyl group, or an o-carbonamidophenyl group.

10. A silver halide color photographic material as claimed in claim 1, wherein $R_2$ and $R_3$ each represents an alkyl group having from 1 to 16 carbon atoms.

11. A silver halide color photographic material as claimed in claim 10, wherein $R_2$ and $R_3$ each represents a methyl group.

12. A silver halide color photographic material as claimed in claim 1, wherein $R_2$ and $R_3$ each represents an alkylene group having from 4 to 11 carbon atoms for forming a ring by combining $R_2$ with $R_3$.

13. A silver halide color photographic material as claimed in claim 12, wherein $R_2$ and $R_3$ each represents a pentamethylene group.

14. A silver halide color photographic material as claimed in claim 1, wherein the cyan dye forming coupler represented by the general formula (I) is used in the same layer or a different layer therefrom together with a cyan coupler represented by the following general formula (V):

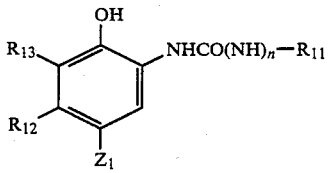

wherein $R_{11}$ represents a substituted or unsubstituted aliphatic group, a substituted or unsubstituted aryl group or a substituted or unsubstituted heterocyclic group; $R_{12}$ represents a substituted or unsubstituted aliphatic group, a substituted or unsubstituted aryl group or a substituted or unsubstituted acylamino group; $R_{13}$ represents a hydrogen atom, a halogen atom, a substituted or unsubstituted aliphatic group, a substituted or unsubstituted aryl group, a substituted or unsubstituted alkoxy group, a substituted or unsubstituted aryloxy group or a substituted or unsubstituted acylamino group, or $R_{12}$ and $R_{13}$ may be combined with each other to form a nitrogen-containing 5-membered to 7-membered ring; $Z_1$ has the same meaning as X defined in the general formula (I); and n represents 0 or 1.

15. A silver halide color photographic material as claimed in claim 1, wherein the cyan dye forming coupler represented by the general formula (I) is present in a silver halide emulsion layer.

16. A silver halide color photographic material as claimed in claim 15, wherein the silver halide emulsion layer is a red-sensitive silver halide emulsion layer.

17. A silver halide color photographic material as claimed in claim 16, wherein the color photographic material further comprises a green-sensitive silver halide emulsion layer containing a magenta coupler and a blue-sensitive silver halide emulsion layer containing a yellow coupler.

18. A silver halide color photographic material as claimed in claim 17, wherein the yellow coupler is a benzoylacetanilide or pivaloylacetanilide yellow coupler.

19. A silver halide color photographic material as claimed in claim 18, wherein the yellow coupler is represented by the following general formula (VI) or (VII):

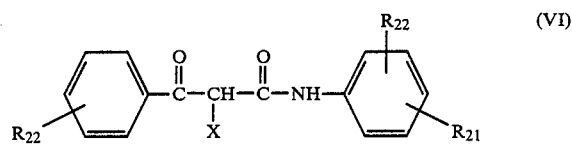

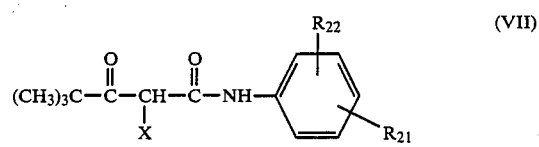

wherein X has the same meaning as defined in the general formula (I); $R_{21}$ represents a diffusion resistant group having from 8 to 32 carbon atoms in total; and $R_{22}$ represents a hydrogen atom, one or more of halogen atoms, lower alkyl groups, lower alkoxy groups or diffusion resistant groups having from 8 to 32 carbon atoms in total, when two or more $R_{22}$'s are present, they may be the same or different.

20. A silver halide color photographic material as claimed in claim 17, wherein the magenta coupler is a 3-anilino-5-pyrazolone, 3-acylamino-5-pyrazolone or pyrazoloazole magenta coupler.

21. A silver halide color photographic material as claimed in claim 20, wherein the magenta coupler is represented by the following general formula (VIII), (IX) or (X):

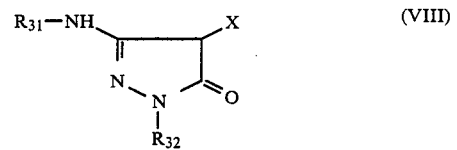

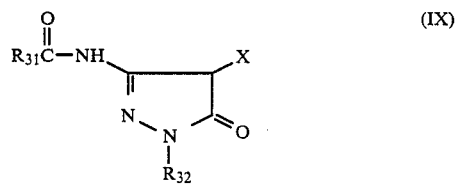

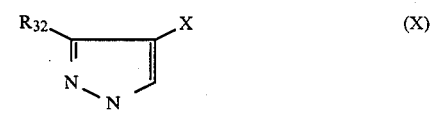

wherein $R_{31}$ represents a diffusion resistant group having from 8 to 32 carbon atoms in total; $R_{32}$ represents a halogen atom, a substituted or unsubstituted lower alkyl group or lower alkoxy group or a substituted or unsubstituted phenyl group or phenoxy group; and Z represents a non-metallic atomic group necessary to form a 5-membered azole ring containing two to four nitrogen atoms, which azole ring may have one or more substituents.

22. A silver halide color photographic material as claimed in claim 1, wherein the cyan dye forming coupler represented by the general formula (I) is used together with a high boiling organic solvent having a boiling point of about 160° C. or above at a normal pressure.

23. A silver halide color photographic material as claimed in claim 1, wherein the cyan dye forming coupler represented by the general formula (I) is used in the same layer or a different layer therefrom together with an ultraviolet light absorbing agent.

24. A silver halide color photographic material as claimed in claim 23, wherein the ultraviolet light absorbing agent is represented by the following general formula (XI):

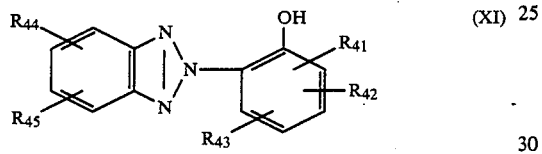

wherein $R_{41}$, $R_{42}$, $R_{43}$, $R_{44}$, and $R_{45}$, which may be the same or different, each represents a hydrogen atom or a substituent for the aliphatic group or aromatic group represented by $R_1$ in the general formula (I), or $R_{44}$ and $R_{45}$ may combine with each other to form a 5-membered or 6-membered aromatic ring composed of carbon atoms.

25. A silver halide color photographic material as claimed in claim 1, wherein the color photographic material further contains a hydroquinone color mixing preventing agent.

26. A silver halide color photographic material as claimed in claim 25, wherein the color mixing preventing agent is represented by the following general formula (XII):

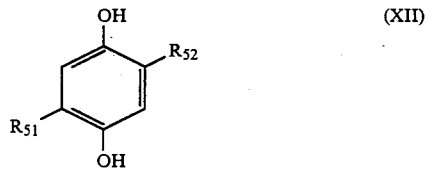

wherein $R_{51}$ and $R_{52}$, which may be the same or different, each represents a hydrogen atom or a substituted or unsubstituted alkyl group, and at least one of $R_{51}$ and $R_{52}$ is an alkyl group.

27. A silver halide color photographic material as claimed in claim 25, wherein the color mixing preventing agent is represented by the following general formula (XIII):

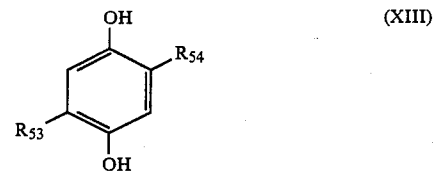

wherein $R_{53}$ represents a substituted or unsubstituted alkyl group, alkylthio group, amido group or alkoxy group; and $R_{54}$ represents a sulfo group or a sulfoalkyl group.

28. A silver halide color photographic material as claimed in claim 25, wherein the color mixing preventing agent is represented by the following general formula (XIV):

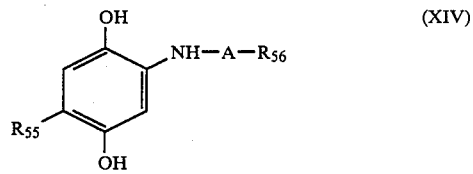

wherein $R_{55}$ represents a hydrogen atom, a halogen atom, a substituted or unsubstituted alkyl group; A represents

or $-SO_2-$; and $R_{56}$ represents a substituted or unsubstituted alkyl group or aryl group.

29. A method of forming a color image comprising imagewise exposing the silver halide color photographic material as claimed in claim 1 to light, developing the color photographic material with a color developing solution and then bleach-fixing.

30. The method of forming a color image as claimed in claim 29, wherein the color developing solution is an alkaline aqueous solution containing an aromatic primary amine color developing agent.

31. The method of forming a color image as claimed in claim 30, wherein the color developing solution substantially does not contain benzyl alcohol.

32. A silver halide color photographic material as claimed in claim 26, wherein said substituted or unsubstituted alkyl group contains from 1 to 20 carbon atoms.

* * * * *